(12) United States Patent
DeCorte et al.

(10) Patent No.: US 10,351,566 B2
(45) Date of Patent: *Jul. 16, 2019

(54) THERAPEUTIC COMPOUNDS FOR PAIN AND SYNTHESIS THEREOF

(71) Applicant: JANSSEN PHARMACEUTICA NV, Beerse (BE)

(72) Inventors: Bart DeCorte, Raritan, NJ (US); Jacob Cornelis Russcher, Nijmegen (NL); Menno Cornelis Franciscus Monnee, Nijmegen (NL)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/043,813

(22) Filed: Jul. 24, 2018

(65) Prior Publication Data

US 2018/0327405 A1 Nov. 15, 2018

Related U.S. Application Data

(63) Continuation of application No. 15/254,952, filed on Sep. 1, 2016, now Pat. No. 10,040,796.

(60) Provisional application No. 62/214,727, filed on Sep. 4, 2015, provisional application No. 62/214,734, filed on Sep. 4, 2015.

(51) Int. Cl.
| | | |
|---|---|---|
| *C07D 471/18* | (2006.01) | |
| *C07D 451/06* | (2006.01) | |
| *C07D 451/12* | (2006.01) | |
| *C07D 451/00* | (2006.01) | |
| *C07D 451/04* | (2006.01) | |
| *C07D 451/10* | (2006.01) | |

(52) U.S. Cl.
CPC ......... *C07D 471/18* (2013.01); *C07D 451/00* (2013.01); *C07D 451/04* (2013.01); *C07D 451/06* (2013.01); *C07D 451/10* (2013.01); *C07D 451/12* (2013.01)

(58) Field of Classification Search
CPC ............................ C07D 471/18; C07D 451/00
USPC ........................................................ 514/292
See application file for complete search history.

(56) References Cited

U.S. PATENT DOCUMENTS

| | | | | |
|---|---|---|---|---|
| 9,994,572 B2* | 6/2018 | DeCorte | .............. | C07D 471/18 |
| 10,040,795 B2* | 8/2018 | DeCorte | .............. | C07D 471/18 |
| 10,040,796 B2* | 8/2018 | DeCorte | .............. | C07D 471/18 |

| | | |
|---|---|---|
| 2017/0066760 A1 | 3/2017 | DeCorte |
| 2017/0066767 A1 | 3/2017 | DeCorte |
| 2017/0066769 A1 | 3/2017 | DeCorte |
| 2017/0066770 A1 | 3/2017 | DeCorte |

OTHER PUBLICATIONS

International Search Report, dated Dec. 23, 2016 for PCT/US2016/049893 filing date Sep. 1, 2016 (WO2017/040778, published Mar. 9, 2017).
International Search Report, dated Dec. 23, 2016 for PCT/US2016/049871 filing date Sep. 1, 2016 (WO2017/040764, published Mar. 9, 2017). I
International Search Report, dated Dec. 23, 2016 for PCT/US2016/049877 filing date Sep. 1, 2016 (WO2017/040767, published Mar. 9, 2017).
International Search Report, dated Dec. 20, 2016 for PCT/US2016/049881 filing date Sep. 1, 2016 (WO2017/040770, published Mar. 9, 2017).
International Search Report, dated Dec. 23, 2016 for PCT/US2016/049885 filing date Sep. 1, 2016 (WO2017/040772, published Mar. 9, 2017).

* cited by examiner

*Primary Examiner* — Rita J Desai
(74) *Attorney, Agent, or Firm* — Mark R. Warfield

(57) ABSTRACT

The invention provides compounds of Formula 1:

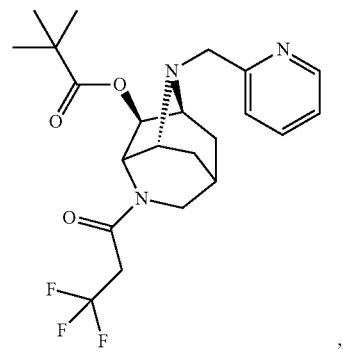

and stereoisomers, pharmaceutically acceptable salts and derivatives thereof; and methods of making and using such compounds. The invention includes pharmaceutical compositions containing such compounds, and the use of such compounds in methods of treating conditions, diseases, or disorders.

22 Claims, 25 Drawing Sheets

THERAPEUTIC COMPOUNDS FOR PAIN AND SYNTHESIS THEREOF

RELATED APPLICATIONS

This patent application is a continuation of U.S. patent application Ser. No. 15/254,952, filed Sep. 1, 2016 (now U.S. Pat. No. 10,040,796, issued Aug. 7, 2018), which claims the benefit of U.S. Provisional Application Ser. No. 62/214,727, filed Sep. 4, 2015, and U.S. Provisional Application Ser. No. 62/214,734, filed Sep. 4, 2015, each of which is incorporated by reference herein in its entirety.

FIELD OF THE INVENTION

The invention provides new pharmaceutically active chemical compounds, which can be used for treating conditions and disorders in animals, mammals, and humans.

BACKGROUND

New chemical compounds having pharmaceutical activity can be indicated for the treatment of previously untreatable conditions, better treatment of conditions than can be achieved with conventional pharmaceutical compounds, and treatment of conditions that were previously treatable with conventional pharmaceutical compounds, but now are no longer effectively treatable. For example, such compounds can be useful in the case of bacterial or viral infectious agents that have evolved to become drug resistant.

SUMMARY OF THE INVENTION

The invention provides a compound of Formula 1:

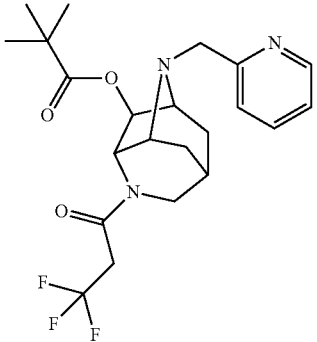 [SMILES: CC(C)(C)C(=O)OC1C2C3CC(CC1N3Cc1ccccn1)CN2C(=O)CC(F)(F)F]

or a stereoisomer, pharmaceutically acceptable salt, or mixture thereof.

In certain embodiments, Formula 1 is

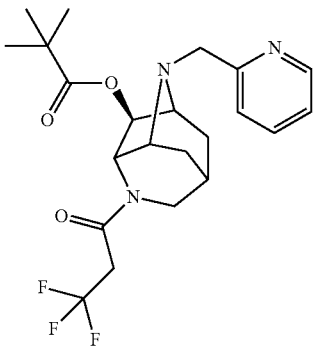 [SMILES: CC(C)(C)C(=O)O[C@@H]1C2C3CC(CC1N3Cc1ccccn1)CN2C(=O)CC(F)(F)F]

((2S*,3S*,3aS*,6R*,7aR*)-1-(pyridin-2-ylmethyl)-4-(3,3,3-trifluoropropanoyl)octahydro-1H-2,6-methanopyrrolo[3,2-b]pyridin-3-yl pivalate).

In certain embodiments, the invention includes a pharmaceutical composition containing a compound of Formula 1 and/or a derivative thereof. In one embodiment, the invention includes a pharmaceutical composition comprising a compound of Formula 1 and/or derivative thereof and a pharmaceutically acceptable carrier or diluent. In another embodiment, the invention provides a method for treating a subject (a human or an animal) suffering from a condition, disease, or disorder, comprising administering to the subject an effective amount of a compound of Formula 1 and/or derivative thereof. In one embodiment, the compound is administered to effect localized delivery to the subject. In another embodiment, the compound is administered to effect systemic delivery to the subject. In a further embodiment, a compound of Formula 1, and/or derivative thereof is used as a medicament, or used in the manufacture of a medicament. In some embodiments, the condition or disorder is neuropathic pain or chronic pain.

In other embodiments, the method includes making the compound of Formula 1. In one such embodiment, the method of making the compound of Formula 1 includes reacting a compound of Formula 2:

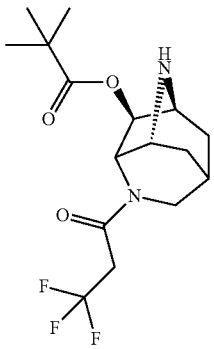 [SMILES: CC(C)(C)C(=O)O[C@@H]1C2[C@H]3CC(C[C@@H]1N3)CN2C(=O)CC(F)(F)F]

(2S*,3S*,3aS*,6R*,7aR*)-4-(3,3,3-trifluoropropanoyl)octahydro-1H-2,6-methanopyrrolo[3,2-b]pyridin-3-yl pivalate with 2-pyridinecarboxaldehyde in the presence of a reducing agent. In some embodiments the 2-pyridinecarboxaldehyde was added before the reducing agent. In certain embodiments the reducing agent is sodium triacetoxyborohydride. In some embodiments the compound of Formula 1 is chirally separated.

In some embodiments, the method can also include making the compound of Formula 2. In an embodiment, the method of making the compound of Formula 2 includes reacting a compound of Formula 3:

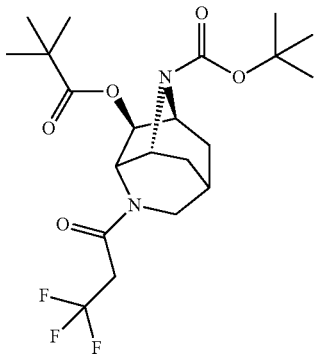 [SMILES: CC(C)(C)OC(=O)N1[C@@H]2CC3C[C@H]1[C@H](OC(=O)C(C)(C)C)C2N(C(=O)CC(F)(F)F)C3]

(2S*,3S*,3aS*,6R*,7aR*)-tert-butyl 3-(pivaloyloxy)-4-(3,3,3-trifluoropropanoyl)octahydro-1H-2,6-methanopyrrolo[3,2-b]pyridine-1-carboxylate with an acid. In certain embodiments, the acid is trifluoroacetic acid.

In some embodiments, the method can also include making the compound of Formula 3. In an embodiment, the method of making the compound of Formula 3 includes reacting a compound of Formula 4:

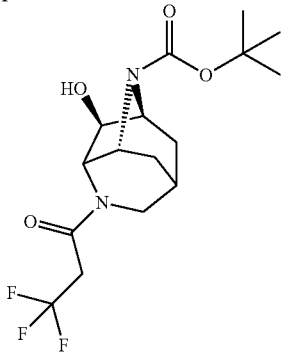

(2S*,3S*,3aS*,6R*,7aR*)-tert-butyl 3-hydroxy-4-(3,3,3-trifluoropropanoyl)octahydro-1H-2,6-methanopyrrolo[3,2-b]pyridine-1-carboxylate with dimethylaminopyridine (DMAP).

In some embodiments, the method can also include making the compound of Formula 4. In an embodiment, the method of making the compound of Formula 4 includes reacting a compound of Formula 5:

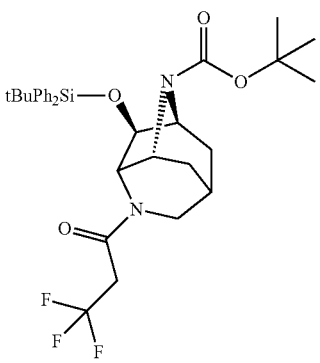

(2S*,3S*,3aS*,6R*,7aR*)-tert-butyl 3-((tertbutyldiphenylsilyl)oxy)-4-(3,3,3 trifluoropropanoyl)octahydro-1H-2,6-methanopyrrolo[3,2-b]pyridine-1-carboxylate with tert-butyldiphenylchlorosilane. In some embodiments the reaction further comprises pyridine.

In some embodiments, the method can also include making the compound of Formula 5. In an embodiment, the method of making the compound of Formula 5 includes reacting a compound of Formula 6.b:

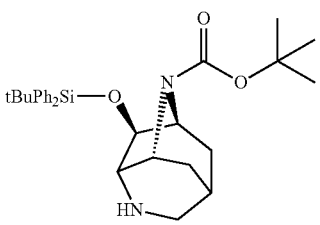

(2S*,3R*,3aS*,6R*,7aR*)-tert-butyl 3-((tertbutyldiphenylsilyl)oxy)octahydro-1H-2,6-methanopyrrolo[3,2-b]pyridine-1-carboxylate with 3,3,3-trifluoropropanoic acid. In some embodiments, the reaction further comprises N—N-Diisopropylethylamine. In certain embodiments, the reaction further comprises (1-[Bis(dimethylamino)methylene]-1H-1,2,3-triazolo[4,5-b]pyridinium 3-oxid hexafluorophosphate) sodium triacetoxyborohydride. In some embodiments, the method includes chirally separating a compound of Formula 7:

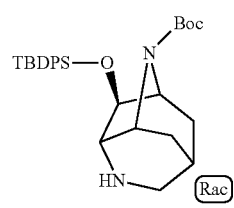

rac-(2S*,3R*,3aS*,6R*,7aR*)-tert-butyl 3-((tertbutyldiphenylsilyl)oxy)octahydro-1H-2,6-methanopyrrolo[3,2-b]pyridine-1-carboxylate.

In other embodiments, the method includes making the compound of Formula 7. In one such embodiment, the method of making the compound of Formula 7 includes reacting a compound of Formula 8:

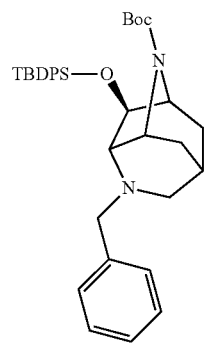

rac-(2R,3R,6S,7aS)-tert-butyl 4-benzyl-3-((tert-butyldiphenylsilyl)oxy)octahydro-1H-2,6-methanopyrrolo[3,2-b]pyridine-1-carboxylate with hydrogen. The reaction may be performed in the presence of a catalyst. In a preferred embodiment, the catalyst includes palladium. For example, the catalyst can be palladium on carbon.

In other embodiments, the method includes making the compound of Formula 8. In one such embodiment, the method of making the compound of Formula 8 includes reacting a compound of Formula 9:

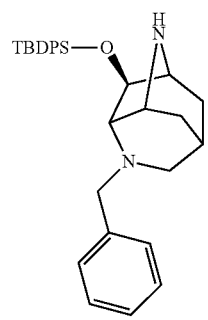

rac-(2R,3R,6S,7aS)-4-benzyl-3-((tert-butyldiphenylsilyl)oxy)octahydro-1H-2,6-methanopyrrolo[3,2-b]pyridine with di-tert-butyl dicarbonate (Boc₂O) to add a tert-butyloxycarbonyl (Boc) protecting group. In a preferred embodiment the reaction further comprises triethylamine (Et₃N).

In other embodiments, the method also includes making the compound of Formula 9. In one such embodiment, the method of making the compound of Formula 9 includes reacting a compound of Formula 10:

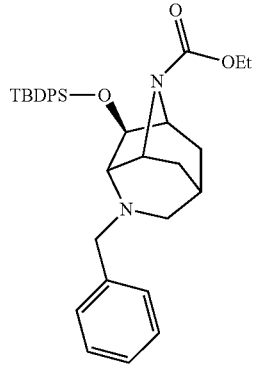

(2R,3R,6S,7aS)-ethyl 4-benzyl-3-((tert-butyldiphenylsilyl)oxy)octahydro-1H-2,6-methanopyrrolo[3,2-b]pyridine-1-carboxylate with iodotrimethylsilane.

In other embodiments, the method also includes making the compound of Formula 10. In one such embodiment, the method of making the compound of Formula 10 includes reacting a compound of Formula 11:

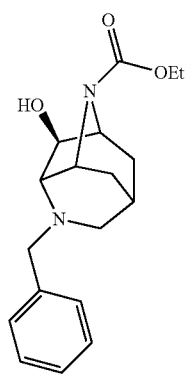 [SMILES: CCOC(=O)N1C2CC3CC1[C@H](O)C2N(Cc1ccccc1)C3]

(2R,3S,6S,7aS)-ethyl-4-benzyl-3-hydroxyoctahydro-1H-2,6-methanopyrrolo[3,2-b]pyridine-1-carboxylate with TBDPS. In a preferred embodiment the reaction further comprises imidazole.

In other embodiments, the method also includes making the compound of Formula 11. In one such embodiment, the method of making the compound of Formula 11 includes reacting a compound of Formula 12:

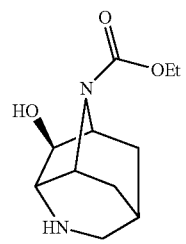 [SMILES: CCOC(=O)N1C2CC3CNC2[C@@H](O)C1C3]

(2R,3S,6S,7aS)-ethyl 3-hydroxyoctahydro-1H-2,6-methanopyrrolo[3,2-b]pyridine-1-carboxylate with benzaldehyde. In a preferred embodiment the reaction further comprises sodium triacetoxyborohydride (STAB).

In other embodiments, the method also includes making the compound of Formula 12. In one such embodiment, the method of making the compound of Formula 12 includes cyclizing a compound of Formula 12.a:

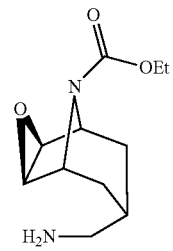 [SMILES: CCOC(=O)N1C2CC(CN)CC1[C@@H]1O[C@H]21]

(1R,2R,4S,5S,7s)-ethyl 7-(aminomethyl)-3-oxa-9-azatricyclo[3.3.1.0²,⁴]nonane-9-carboxylate in a solvent. The solvent can be ethanol (EtOH).

In other embodiments, the method also includes making the compound of Formula 12.a. In one such embodiment, the method of making the compound of Formula 12.a includes reacting a compound of Formula 13:

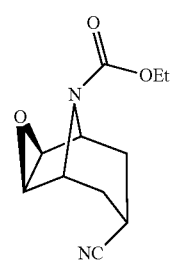 [SMILES: CCOC(=O)N1C2CC(C#N)CC1[C@@H]1O[C@H]21]

(1R,2R,4S,5S,7s)-ethyl 7-cyano-3-oxa-9-azatricyclo[3.3.1.0²,⁴]nonane-9-carboxylate with hydrogen. The reaction may be performed in the presence of a catalyst. In one embodiment, the catalyst includes nickel. For example, the catalyst can be Raney-nickel.

In other embodiments, the method also includes making the compound of Formula 13. In one such embodiment, the method of making the compound of Formula 13 includes reacting a compound of Formula 14:

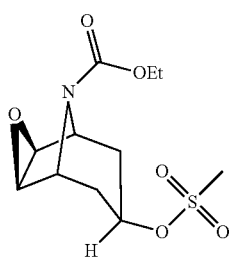 [SMILES: CCOC(=O)N1C2CC(OS(C)(=O)=O)CC1[C@@H]1O[C@H]21]

(1R,2R,4S,5S,7r)-ethyl 7-((methylsulfonyl)oxy)-3-oxa-9-azatricyclo[3.3.1.0²,⁴]nonane-9-carboxylate with potassium cyanide. In other embodiments the reaction further comprises 18-crown-6 (1,4,7,10,13,16-hexaoxacyclooctadecane).

In other embodiments, the method also includes making the compound of Formula 14. In one such embodiment, the method of making the compound of Formula 14 includes reacting a compound of Formula 15:

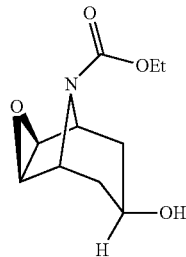 [SMILES: CCOC(=O)N1C2CC(O)CC1[C@@H]1O[C@H]21]

(1R,2R,4S,5S,7r)-ethyl 7-hydroxy-3-oxa-9-azatricyclo[3.3.1.02,4]nonane-9-carboxylate with mesyl chloride. In a preferred embodiment the reaction further comprises triethylamine (ET₃N).

In other embodiments, the method also includes making the compound of Formula 15. In one such embodiment, the method of making the compound of Formula 15 includes reacting a compound of Formula 16:

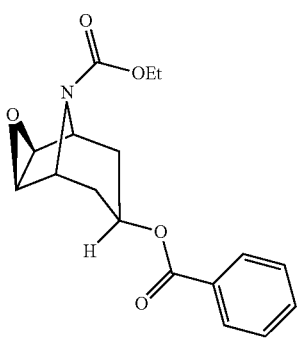 [SMILES: CCOC(=O)N1C2CC(OC(=O)c3ccccc3)CC1[C@@H]1O[C@H]21]

(1R,2R,4S,5S,7r)-ethyl 7-(benzoyloxy)-3-oxa-9-azatricyclo[3.3.1.02,4]nonane-9-carboxylate with a reducing agent. The reducing agent can be sodium borohydride.

In other embodiments, the method also includes making the compound of Formula 16. In one such embodiment, the method of making the compound of Formula 16 includes reacting a compound of Formula 17:

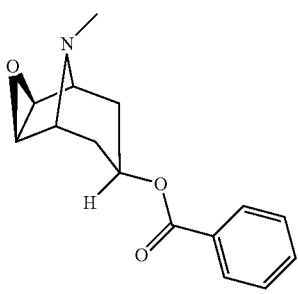 [SMILES: CN1C2CC(OC(=O)c3ccccc3)CC1[C@@H]1O[C@H]21]

(1R,2R,4S,5S,7r)-9-methyl-3-oxa-9-azatricyclo[3.3.1.02,4]nonan-7-yl benzoate with ethyl chloroformate. In a preferred embodiment the reaction further comprises a base. The base can be potassium carbonate.

In other embodiments, the method also includes making the compound of Formula 17. In one such embodiment, the method of making the compound of Formula 17 includes reacting a compound of Formula 18:

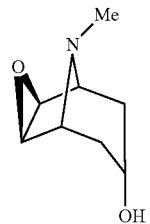 [SMILES: CN1C2CC(O)CC1[C@@H]1O[C@H]21]

(1R,2R,4S,5S)-9-methyl-3-oxa-9-azatricyclo[3.3.1.02,4]nonan-7-ol) with benzoic acid in the presence of an activating agent. The activating agent can be diethylazodicaroxylate (DEAD) with triphenylphosphine (PPh₃) or diisopropyl azodicarboxylate (DIAD) with PPh₃.

In other embodiments, the method also includes making the compound of Formula 18. In one such embodiment, the method of making the compound of Formula 18 includes reacting a compound of Formula 19:

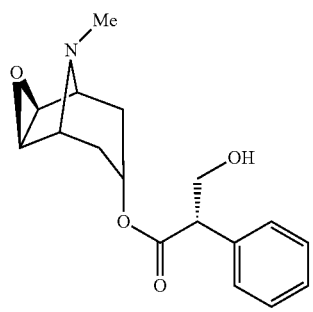 [SMILES: CN1C2CC(OC(=O)[C@H](CO)c3ccccc3)CC1[C@@H]1O[C@H]21]

(2S)-(1R,2R,4S,5S)-9-methyl-3-oxa-9-azatricyclo[3.3.1.02,4]nonan-7-yl-3-hydroxy-2-phenylpropanoate hydrobromide trihydrate (scopolamine) with a reducing agent. The reducing agent can be sodium borohydride. In a preferred embodiment the reaction further comprises HCl in isopropyl alcohol.

In some embodiments, the compounds described herein are used in the treatment or prevention of neuropathic pain in a subject in need. In other embodiments the compounds described herein are useful in the treatment or prevention of chronic pain in a subject in need.

BRIEF DESCRIPTION OF THE DRAWINGS

The preceding Summary, as well as the following Detailed Description of the invention, can be better understood when read in conjunction with the appended Figures. For the purpose of illustrating the invention, the Figures demonstrate embodiments of the present invention. However, it should be understood that the invention is not limited to the precise arrangements, examples, and instrumentalities shown.

FIG. 3A shows the results of a $^{1H}$NMR analysis of the compound of Formula 16. FIG. 3B shows the results of a MS analysis of the compound of Formula 16.

FIG. 8A shows the results of a MS analysis of the compound of Formula 11. FIG. 8B shows the results of a $^{1H}$NMR analysis of the compound of Formula 11.

FIG. 9A shows the results of a LCMS analysis of the compound of Formula 10. FIG. 9B shows the results of a $^{1H}$NMR analysis of the compound of Formula 10.

FIG. 11A shows the results of a $^{1H}$NMR analysis of the compound of Formula 8.

FIG. 11B shows the results of a LCMS analysis of the compound of Formula 8.

FIG. 12A shows the results of a LCMS analysis of the compound of Formula 7. FIG. 12B shows the results of a $^{1H}$NMR analysis of the compound of Formula 7.

DETAILED DESCRIPTION

Figure 1:
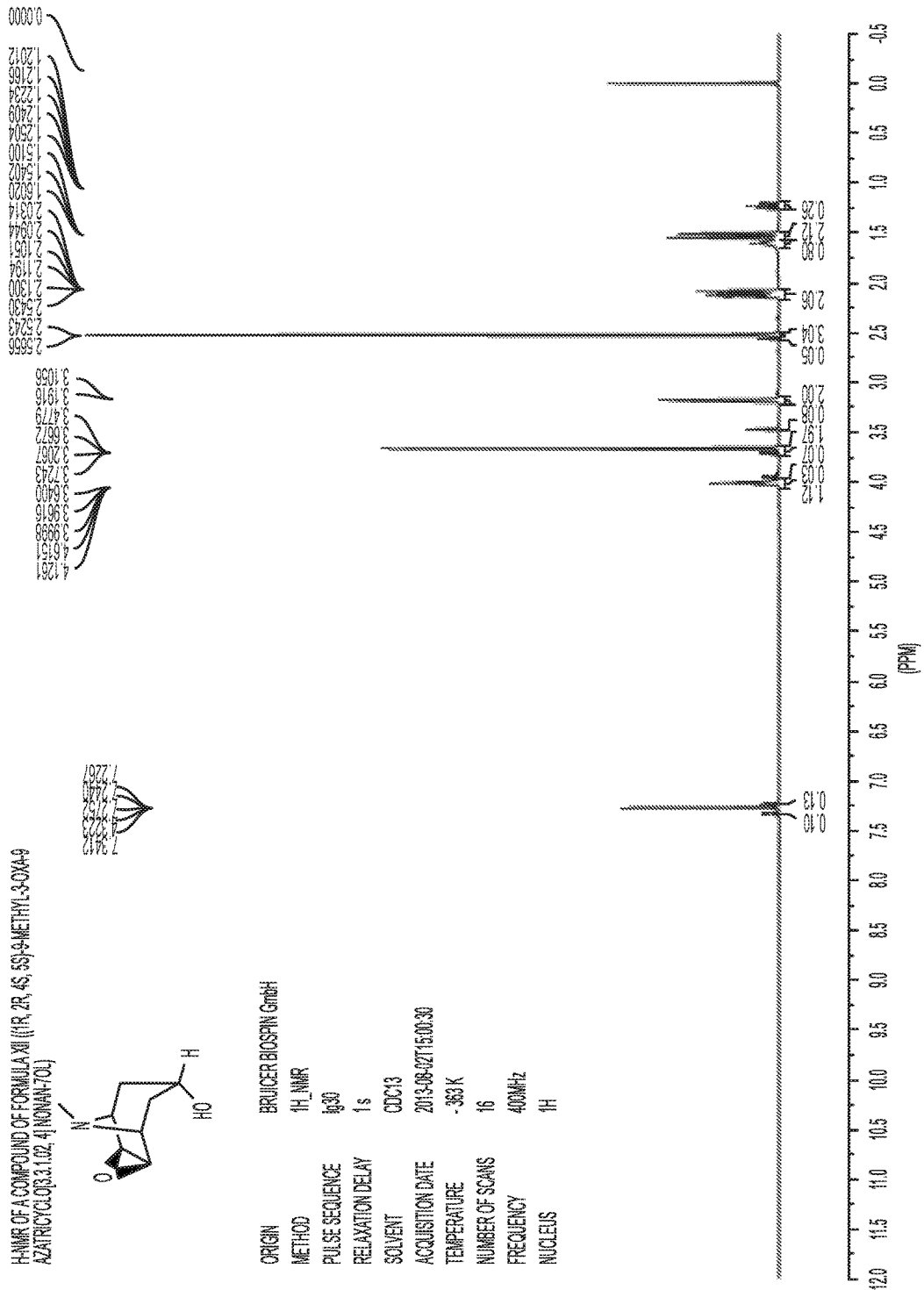
FIG. 1 shows the results of a $^{1H}$NMR (CDCl₃) analysis of the compound of Formula 18, according to one embodiment of the invention.

Embodiments of the invention are discussed in detail below. In describing these embodiments, specific terminology is employed for the sake of clarity. However, the invention is not intended to be limited to the specific terminology selected. A person skilled in the relevant art will recognize that other equivalent parts can be employed and other methods developed without limitation to specific examples.

Certain Definitions

The term "alkyl" refers to branched or unbranched hydrocarbon chains, in for example, hydrocarbon chains having from 1 to 12 carbon atoms in the chain. In some embodiments, an alkyl group is a $C_1$-$C_6$ alkyl group. In some embodiments, an alkyl group is a $C_1$-$C_4$ alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_1$-$C_6$ haloalkyl group. In some embodiments, a haloalkyl group is a $C_1$-$C_4$ haloalkyl group. One exemplary substitutent is fluoro. Preferred substituted alkyl groups of the invention include trihalogenated alkyl groups such as trifluoromethyl groups. Haloalkyl includes and is not limited to $CF_3$, $CH_2F$, —$CHF_2$, —$CH_2Cl$, —$CH_2$—$CF_3$, and the like.

"Cycloalkyl" refers to monocyclic, non-aromatic hydrocarbon groups having from 3 to 7 carbon atoms. Examples of cycloalkyl groups include, for example, cyclopropyl, cyclobutyl, cyclopentyl, cyclohexyl, and the like.

The term "alkoxy" includes a straight chain or branched alkyl group with a terminal oxygen linking the alkyl group to the rest of the molecule. In some embodiments, an alkoxy group is a $C_1$-$C_6$ alkoxy group. In some embodiments, an alkoxy group is a $C_1$-$C_4$ alkoxy group. Alkoxy includes methoxy, ethoxy, propoxy, isopropoxy, butoxy, t-butoxy, pentoxy and so on.

The term "heterocycle" represents" a mono- or bi-cyclic hydrocarbon ring structure optionally containing heteroatoms selected from O, S, and N. Heterocyclyl rings can have 2 to 10 carbon atoms in the ring.

The term "halogen" represents chlorine, fluorine, bromine, or iodine. The term "halo" represents chloro, fluoro, bromo, or iodo.

A wavy line "⸻" indicates the point of attachment to the rest of the molecule.

"Benzyl" and —$CH_2$-phenyl are used interchangeably.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition.

Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

"Compounds of the present invention," and equivalent expressions, are meant to embrace compounds of the Formula as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive or radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the invention, radioactive or not, are intended to be encompassed within the scope of the invention. In one aspect, provided herein are deuterated or tritiated analogs of compounds described.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci-and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)-or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

As used herein, the term "localized delivery" denotes delivery of a pharmaceutical or therapeutic agent to a specific, limited region of the body.

As used herein, the term "systemic delivery" denotes delivery of a pharmaceutical or therapeutic agent throughout the body, for example, through administration to the circulatory system.

As used herein, the term "mass spectrometry (MS)" denotes an analytic technique that ionizes a chemical compound to generate charged molecules or molecule fragments and measures their abundance as a function of mass-to-charge (m/z) ratio (the mass spectrum). From the mass spectrum, conclusions as to the structure of the chemical compound can be drawn.

As used herein, the term "liquid chromatography-mass spectrometry (LCMS)" denotes an analytic technique that combines the physical separation capability of liquid chromatography with the analytic capability of mass spectrometry. In the liquid chromatography step, the sample is introduced into a column packed with a stationary phase, separating the chemical compounds of the sample by their retention time (Rt) in the column. The chemical compound or compounds associated with a retention time interval are then directed to a mass spectrometer, to obtain a mass spectrum that allows conclusions as to the structure of this chemical compound or compounds to be drawn.

As used herein, the term "thin-layer chromatography (TLC)" denotes an analytic technique that separates chemical compounds in a sample by the different rates in which they are drawn up a plate coated with a stationary phase material.

As used herein, the term "nuclear magnetic resonance spectroscopy (NMR)" denotes an analytic technique that measures the intensity of a resonance response of a set of nuclei to a radio frequency pulse to allow information as to the electronic environment of the nuclei to be obtained. From this, conclusions can be drawn as to the chemical structure of the compound in which the nuclei reside. A nuclear magnetic resonance spectroscopy technique that uses hydrogen nuclei (protons) is termed proton nuclear magnetic resonance spectroscopy ($^{1H}$NMR).

The term "ester" is used herein as is conventional in the field of organic chemistry. For example, the term "ester" can denote a carbonyl group with a bonded oxygen and alkyl or an oxygen with a bonded carbonyl and alkyl.

As used herein, the term "metabolic syndrome" denotes a medical or biological disorder of energy utilization and storage in an animal or human, which can be characterized by abdominal obesity, elevated blood pressure, elevated fasting plasma glucose, high serum triglycerides, and/or low high-density cholesterol levels.

As used herein, the term "polymerase chain reaction" denotes a biomedical technique for generating many copies of a particular DNA sequence.

As used herein, the term "triturate" denotes a method of purifying a material in which the crude material is washed with a solvent. The solvent can be selected, so that the desired product is insoluble and the impurities are soluble, in which case, the purified product is left in solid form and the impurities are removed with the solvent. Conversely, the solvent can be selected, so that the desired product is soluble and the impurities are insoluble, in which case, the purified product is in solution and the impurities are removed as solids. The solvent can then be removed, for example, through evaporation, to obtain the purified product.

As used herein, the term "Boc-protection" denotes functionalization of a chemical compound with a tert-butyloxycarbonyl (Boc) group as a protecting group. This allows the chemical compound as a whole to be treated with reagents that would otherwise undesirably attack the unprotected group. The protected group can thereafter be deprotected to yield the desired original group.

Exemplary Compounds

The present invention, provides a molecule having the structure of a compound of the structure of Formula 1:

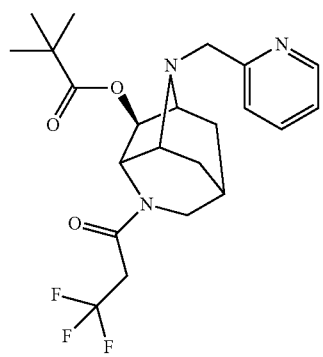 [SMILES: CC(C)(C)C(=O)O[C@@H]1C2C3CC(CC1N3Cc1ccccn1)CN2C(=O)CC(F)(F)F]

(2S,3S,6R,7aR)-1-(pyridin-2-ylmethyl)-4-(3,3,3-trifluoropropanoyl)octahydro-1H-2,6-methanopyrrolo[3,2-b]pyridin-3-yl pivalate, and stereoisomers thereof. This compound can be prepared by the reaction sequences described in the Schemes set forth in Example 1.

Pharmaceutical Compositions and Administration

The compounds of the present invention are useful as pharmaceutical agents and can be incorporated into pharmaceutical compositions comprising a therapeutically effective amount of a compound of the invention, as defined herein, and a pharmaceutically acceptable carrier or diluent.

The compounds of the invention can also be used in the manufacture of derivative compounds that are useful as pharmaceutical agents, and which can likewise be incorporated into pharmaceutical compositions prepared with a therapeutically effective amount of such a derivative compound and a pharmaceutically acceptable carrier or diluent.

The compounds of the invention, and such derivatives thereof, can be useful in the treatment of conditions, diseases, and disorders in humans and animals. Such compounds can be formulated as pharmaceutical compositions and administered to a subject in need of treatment, for example a mammal, such as a human patient, in a variety of forms adapted to the chosen route of administration. For example compounds of the invention may be formulated for administration, orally, nasally, intraperitoneally, or parenterally, by intravenous, intramuscular, topical, or subcutaneous routes, or by injection into tissue.

Thus, compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with an inert powdered carrier and inhaled by the subject or insufflated. Such compositions and preparations should contain at least 0.1% of a compound of the present invention. The percentage of the compound of the invention present in such compositions and preparations may, of course, be varied and may conveniently be between about 2% to about 60% of the weight of a given unit dosage form. The amount of the compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or for otherwise modifying the physical form of the solid unit dosage form. For instance, tablets, pills, or capsules may be coated with gelatin, wax, shellac, or sugar, and the like. A syrup or elixir may contain the active compound, sucrose or fructose as a sweetening agent, methyl and propylparabens as preservatives, a dye, and flavoring such as cherry or orange flavor. Of course, any material used in preparing any unit dosage form should be pharmaceutically acceptable and substantially non-toxic in the amounts employed. In addition, the compounds may be incorporated into sustained-release preparations and devices. For example, the compounds may be incorporated into time release capsules, time release tablets, time release pills, and time release polymers or nanoparticles.

The compounds may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof, and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, preferably followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of the therapeutic compounds of the invention in such formulations can vary widely depending on the nature of the formulation and intended route of administration. For example, the concentration of the compounds in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Effective dosages and routes of administration of agents of the invention are conventional. The exact amount (effective dose) of the agent will vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The compounds are conveniently administered in unit dosage form; for example, containing about 0.05 to about 10000 mg, about 0.5 to about 10000 mg, about 5 to about 1000 mg, or about 50 to about 500 mg of active ingredient per unit dosage form.

The compounds can be administered to achieve peak plasma concentrations of, for example, from about 0.25 to about 200 μM, about 0.5 to about 75 μM, about 1 to about 50 μM, about 2 to about 30 μM, or about 5 to about 25 μM. Exemplary desirable plasma concentrations include at least 0.25, 0.5, 1, 5, 10, 25, 50, 75, 100 or 200 μM. For example, plasma levels may be from about 1 to about 100 micromolar or from about 10 to about 25 micromolar. This may be achieved, for example, by the intravenous injection of a 0.05 to 5% solution of the compounds, optionally in saline, or orally administered as a bolus containing about 1 to about 100 mg of the compounds. Desirable blood levels may be maintained by continuous or intermittent infusion.

The compounds may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

All documents, references, and information, including, but not limited to, journal articles, patent applications, and patents, that are mentioned, cited, or referred to in this application are hereby incorporated by reference in their entirety as if each had been individually incorporated.

EXAMPLE 1

Synthesis of a Compound of Formula I

A compound of Formula 1 was synthesized, from the compound of Formula 19 (Scopolamine [51-34-3]) ((2S)-(1R,2R,4S,5S)-9-methyl-3-oxa-9-azatricyclo[3.3.1.02,4] nonan-7-yl-3-hydroxy-2-phenylpropanoate hydrobromide trihydrate) by the steps described below in Schemes 1 through 18.

A first step is illustrated in Scheme 1.

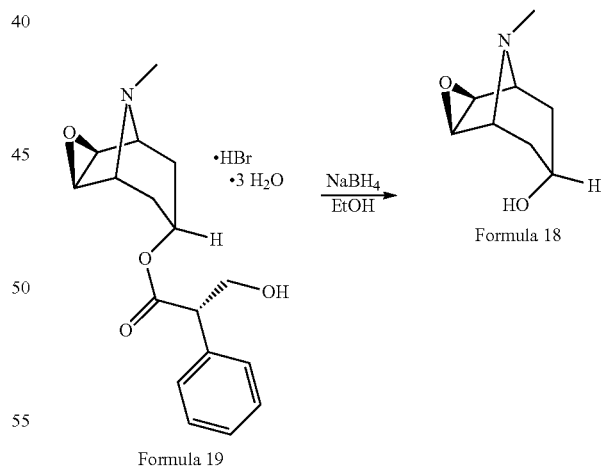

Inside a 10 liter four necked round bottom flask, sodium borohydride (172 g, 4558 mmol) was added portion wise over about 2 hours to a mechanically stirred suspension of a compound of Formula 19 (333 g, 760 mmol) in 3 liters of absolute ethanol in an ice bath. During this time, gas formation occurred and the suspension was stirred while being warmed to ambient temperature overnight. While being heated, at approximately 10° C., sudden additional gas formation and foaming occurred.

The milky suspension was then concentrated to about half of its original volume (i.e. from about 3 L to 1.5 L) with additional precipitate observed, which yielded the batch. 5 M HCl in isopropyl alcohol (IPA) (5318 mmol, 1.064 L) was then diluted with 2 L of technical diethyl ether (Et$_2$O). The obtained hydrochloric acid (HCl) solution was then added drop wise to the ice-chilled batch, while being stirred. The white suspension was allowed to be mechanically stirred overnight to allow for full hydrolysis of the borate salts.

The reaction mixture was filtered and the resulting solid was rinsed twice with 500 mL portions of Et$_2$O. The dried solid (which contained some Et$_2$O) was dissolved in a minimum amount of 10% aqueous potassium carbonate (K$_2$CO$_3$) solution (~1.5 L) until just a clear solution was obtained. 200 mL of brine and ~50 g solid NaCl was added to the solution. The aqueous phase was then thoroughly extracted with chloroform/methanol (MeOH)/[7N NH$_3$ in MeOH](85:14:1). This procedure was performed 5 times with 1.0 L portions of this solvent mixture each.

The combined organic extracts were dried (sodium sulphate (Na$_2$SO$_4$)), filtered and the solvent was removed under reduced pressure to give 102.2 g (659 mmol) of a compound of Formula 18 ((1R,2R,4S,5S)-9-methyl-3-oxa-9-azatricyclo[3.3.1.02,4]nonan-7-431) as a slightly tan oil at 87% yield. $^{1H}$NMR (CDCl$_3$) (FIG. 1) showed structural agreement with the compound of Formula 18 with minor amounts of impurities. $^{1H}$NMR (400 MHz, Chloroform-d) δ 4.03-4.00 (m, 1H), 3.67 (s, 2H), 3.20-3.18 (m, 2H), 2.52 (s, 3H), 2.14-2.08 (m, 2H), 1.69-1.37 (m, 3H).

The next step proceeded as illustrated by Scheme 2.

(EtOAc), extracted with 1 L of saturated sodium bicarbonate (NaHCO$_3$), and subsequently with aqueous 2 M HCl (1×1 L, 2×0.5 L). The combined acidic aqueous fractions were washed once more with 1 L of EtOAc. Approximately 400 g of potassium carbonate (K$_2$CO$_3$) was added portion wise to the acidic aqueous layer, while being stirred, until no more gas formation was observed. The pH of the resulting solution was slightly basic and slightly turbid and yellow.

Figure 2:
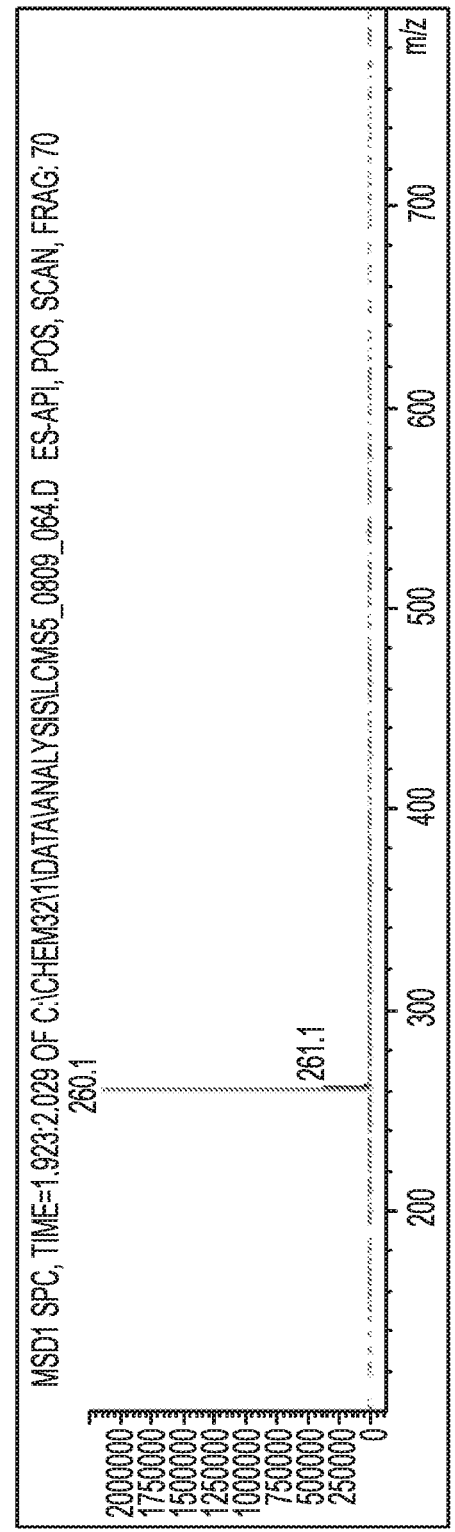
FIG. 2 shows the results of a MS analysis of the compound of Formula 17, according to one embodiment of the invention.

The aqueous phase was then extracted with a dichloromethane (DCM)/MeOH 9:1 (3×, 1 L each) solution and the combined organic fractions were dried with sodium sulfate (Na$_2$SO$_4$), filtered and concentrated to afford 118.3 g (447 mmol) of a compound of Formula 17 ((1R,2R,4S,5S, 7r)-9-methyl-3-oxa-9-azatricyclo[3.3.1.02,4]nonan-7-yl benzoate), which was then confirmed by MS (FIG. 2) to have 98% purity at 67.9% yield. $^{1H}$NMR (400 MHz, Chloroform-d) δ 8.07-7.93 (m, 2H), 7.59-7.48 (m, 1H), 7.44-7.40 (m, 2H), 5.39-5.30 (m, 1H), 3.63 (s, 2H), 3.42-3.25 (m, 2H), 2.57 (s, 3H), 2.10-2.04 (m, 2H), 1.92-1.86 (m, 2H).

The next step proceeded as illustrated in Scheme 3.

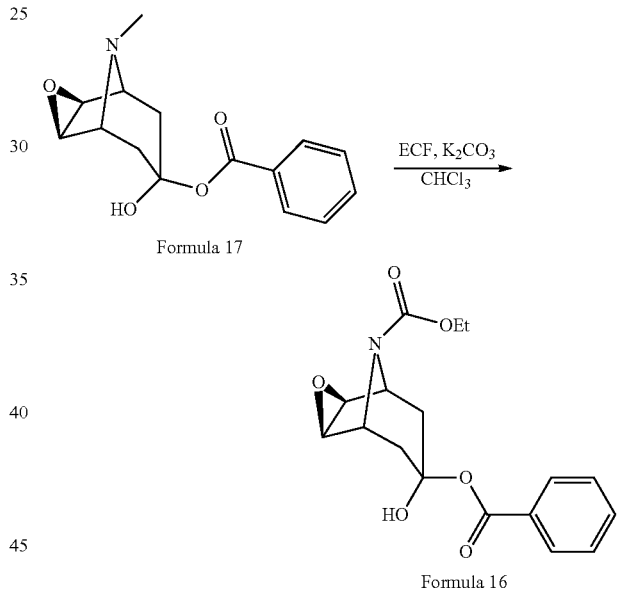

Scheme 3

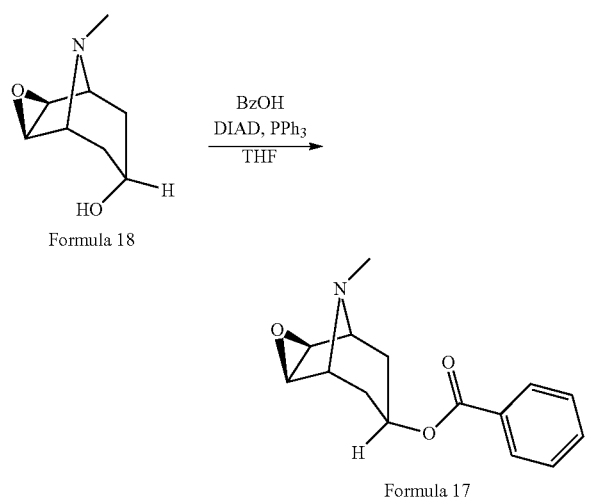

Scheme 2

To a solution of the compound of Formula 18 (102.2 g, 659 mmol), benzoic acid (BzOH) (97 g, 790 mmol) and triphenylphosphine (PPh$_3$) (207 g, 790 mmol) in 1000 mL of dry tetrahydrofuran (THF) a solution of diisopropyl azodicaboxylate (DIAD) (160 g, 790 mmol, 154 mL) in 100 mL of dry THF was added drop wise over a period of 4 hours. During the addition the solution was kept between −35 and −25° C. using acetone/dry ice. The clear, colorless solution was then removed from the ice bath and stirred at room temperature overnight.

Samples were taken and analyzed, and the analysis showed the reaction went to completion. The reaction mixture was concentrated, dissolved in 1 L of ethyl acetate To a solution of the compound of Formula 17 (201.9 g, 779 mmol) in chloroform (350 mL) under a nitrogen atmosphere (not a stream), K$_2$CO$_3$ (452 g, 3270 mmol) and ethyl chloroformate (279 g, 2569 mmol, 247 mL) were added to form a light yellow suspension which was then stirred under reflux overnight.

A sample was then taken and analyzed to show that the reaction had reached a 74% conversion to the product, a compound of Formula 16 (1R,2R,4S,5S,7r)-ethyl 7-(benzoyloxy)-3-oxa-9-azatricyclo[3.3.1.02,4]nonane-9-carboxylate). The mixture was further stirred at reflux temperature for another 24 hours.

Another sample was then taken and analyzed which showed that the reaction had reached a 75% conversion to product. In order to drive the reaction toward completion, additional K$_2$CO$_3$ (53.8 g, 389 mmol) and ethyl chloroformate (85 g, 779 mmol, 74.8 mL) were added to the reaction solution and the mixture was stirred at reflux temperature overnight.

After being stirred and refluxed overnight, another sample was taken which was analyzed to show that the reaction had reached 81% conversion to the compound of Formula 16.

The reaction mixture was then diluted with 500 mL of DCM and the organic layer was washed with 750 mL of a half saturated aqueous NaHCO$_3$ solution, 750 mL of 0.4 M aqueous HCl, and 750 mL of brine. The mixture next dried over Na$_2$SO$_4$, then filtered and concentrated under reduced pressure which then afforded a yellow oil. 300 mL of Heptane was added and the mixture was vigorously stirred overnight.

Figure 3A:
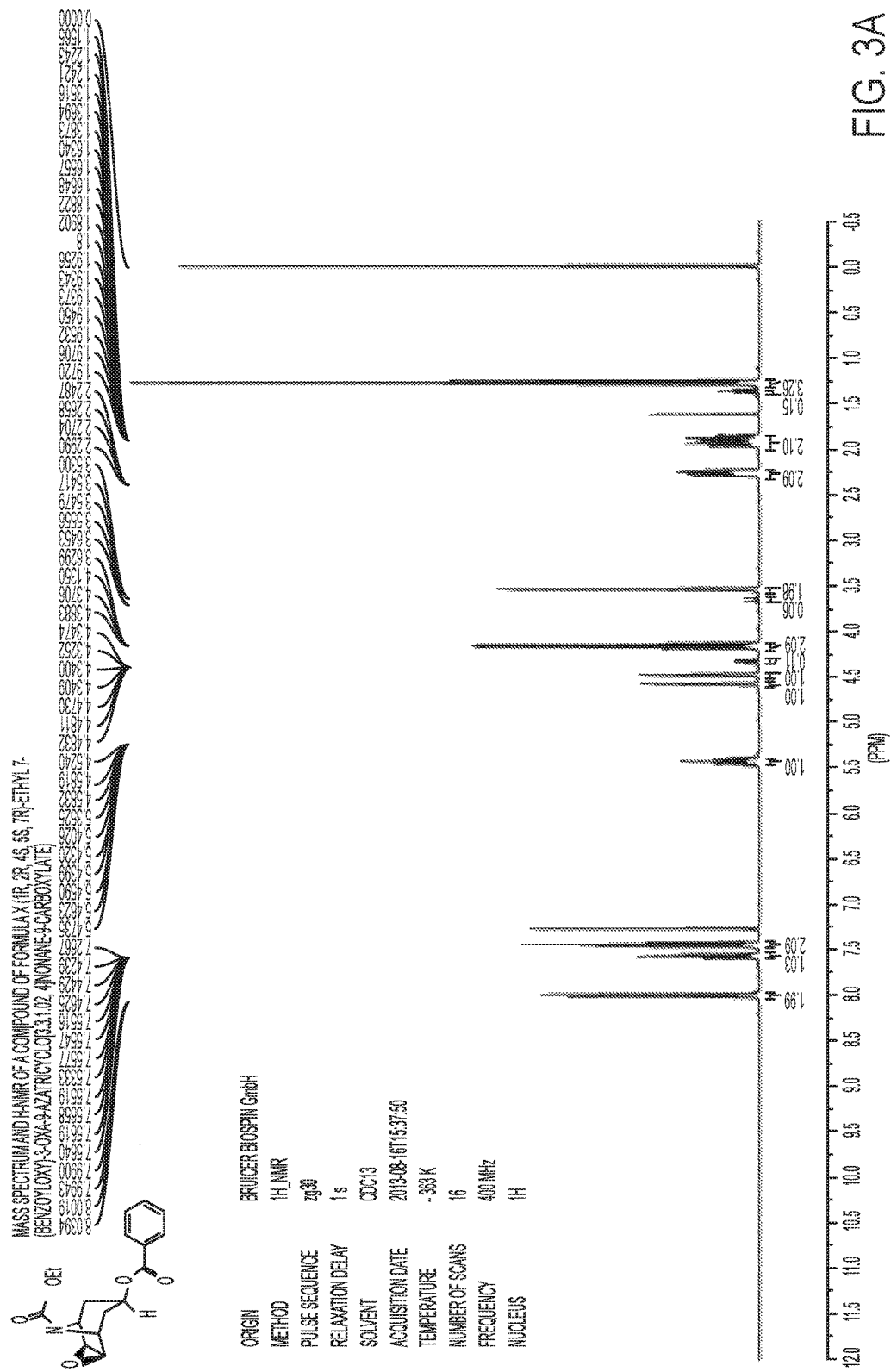
FIGS. 3A and 3B show the results of a structural analysis of the compound of Formula 16.
Figure 3B:
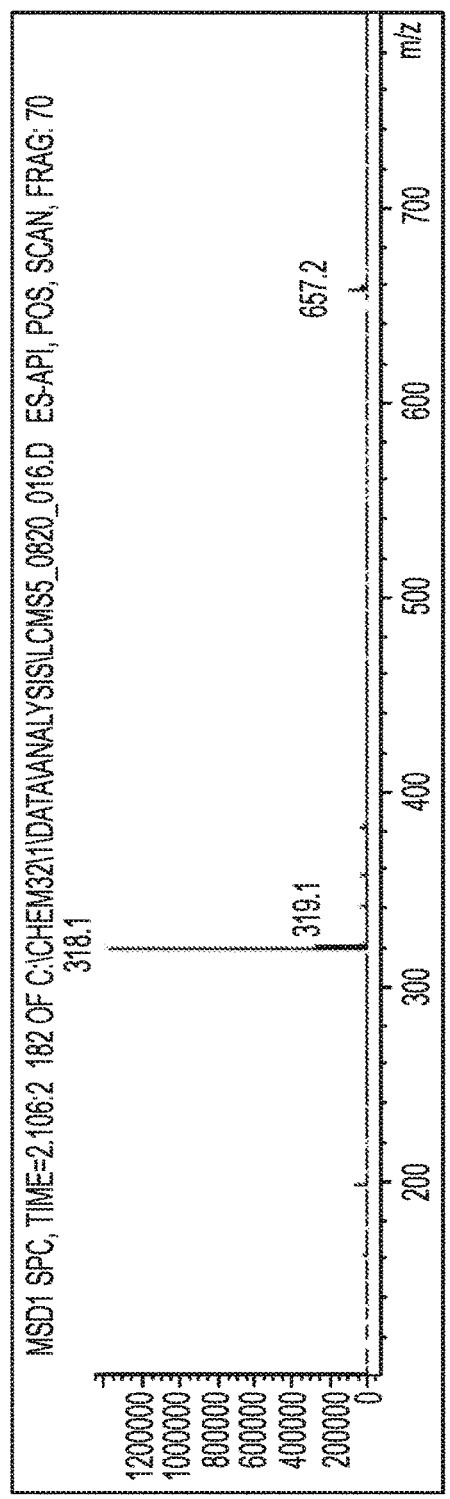

A white suspension had formed which contained big white lumps which were crushed with a spatula. The suspension was filtered over a glass filter, rinsed with approximately 250 mL of heptane and approximately 200 mL of pentane. The suspension was then dried using a vacuum oven for 3 hours yielding the compound of Formula 16 as a white solid (219.6 g, 692 mmol, 89% yield). LCMS of the product showed a percent yield greater than 95%, with a mass and structure agreement with the desired product as shown in the MS (FIG. 3B) and $^{1H}$NMR (FIG. 3A)). $^{1H}$NMR (400 MHz, Chloroform-d) δ 8.01-7.97 (m, 2H), 7.61-7.53 (m, 1H), 7.48-7.42 (m, 2H), 5.48-5.39 (m, 1H), 4.58 (m, 1H), 4.48 (m, 1H), 4.16 (q, J=7.1 Hz, 2H), 3.56-3.53 (m, 2H), 2.34-2.21 (m, 2H), 1.98-1.86 (m, 2H), 1.27 (t, J=7.1 Hz, 3H).

The next step proceeded as illustrated in Scheme 4.

Scheme 4

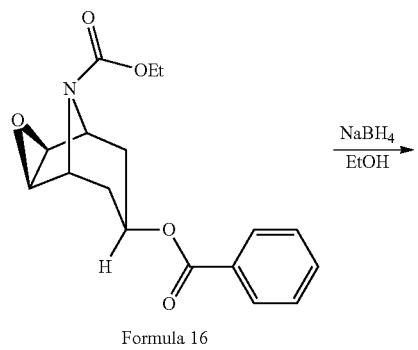

Formula 16

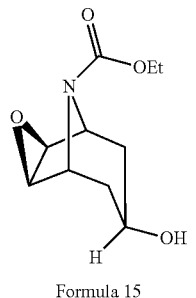

Formula 15

In a 6 L three necked flask, sodium borohydride (157 g, 4152 mmol) was added to a suspension of the compound of Formula 16 (219.6 g, 692 mmol) in 1.5 L of absolute ethanol at room temperature. The reaction was exothermic, and had an internal temperature greater than 60° C. over a period of approximately 4 hours, during the reaction extreme gas/foam formation was observed. The suspension was magnetically stirred at 50° C. overnight.

A sample was then taken and analyzed by TLC to show that the reaction had gone to completion. The resulting product was a white solid which stopped the magnetic stirrer during the night. The mixture was concentrated under reduced pressure and the white solid residue was partitioned between 1 L of chloroform and 3.5 L of half-saturated aqueous NaHCO$_3$ solution. The layers were next separated and the aqueous layer was extracted with additional chloroform (2×, 1 L each). The combined organic layers were washed with 1 L of brine, dried over Na$_2$SO$_4$, and filtered and concentrated under reduced pressure to afford approximately 220 g of the product as a white solid which was stirred in 0.6 L of heptane overnight with a magnetic stirrer.

The mixture was then filtered off, the product had formed spheres which were crushed and had 500 mL of heptane added to them. The mixture was stirred vigorously overnight with a magnetic stirrer.

After stirring the mixture overnight, the off-white suspension still contained spheres which then were crushed with a spatula. The suspension was filtered and the residue was rinsed with approximately 300 mL heptane and dried by vacuum which yielded approximately 148 g of the product.

Figure 4:
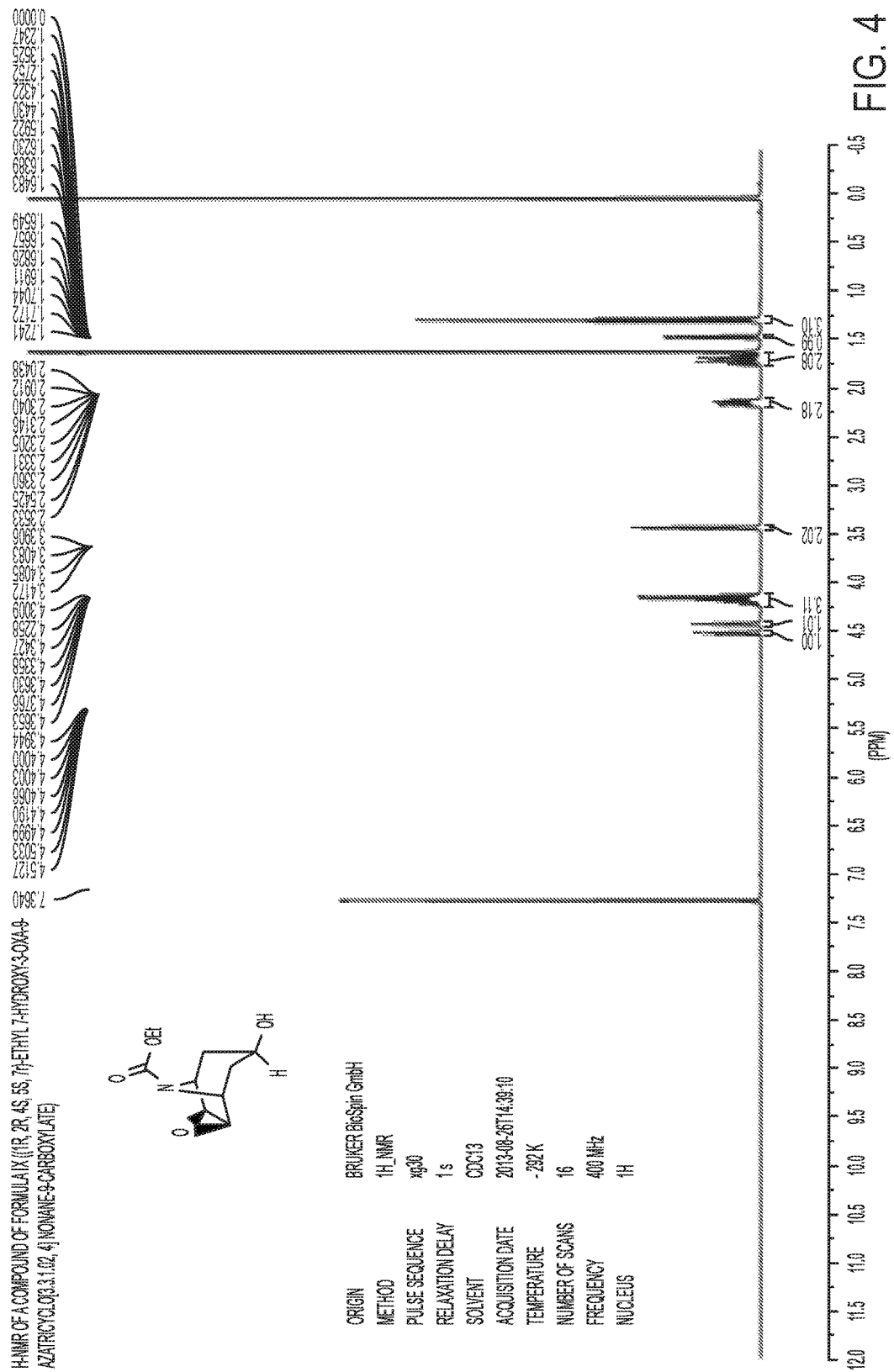
FIG. 4 shows the results of a $^{1H}$NMR analysis of the compound of Formula 15.

A sample was taken and analysed by $^{1H}$NMR to show the structure was in agreement with the compound of Formula 15 (1R,2R,4S,5S,7r)-ethyl 7-hydroxy-3-oxa-9-azatricyclo [3.3.1.02,4]nonane-9-carboxylate), (FIG. 4).

The residue was then stirred in approximately 300 mL of Et$_2$O for 1 hour. The white suspension was filtered; and the residue was rinsed again with approximately 300 mL of Et$_2$O and then dried by vacuum (under N$_2$-flow) to yield the compound of Formula 15 (122 g, 572 mmol, 82% yield). $^{1H}$NMR (400 MHz, Chloroform-d) δ 4.50 (m, 1H), 4.41 (m, 1H), 4.23-4.09 (m, 3H), 3.42-3.39 (m, 2H), 2.15-2.08 (m, 2H), 1.73-1.62 (m, 2H), 1.44 (d, J=5.9 Hz, 1H), 1.26 (t, J=7.1 Hz, 3H).

The next step proceeded as illustrated in Scheme 5.

Scheme 5

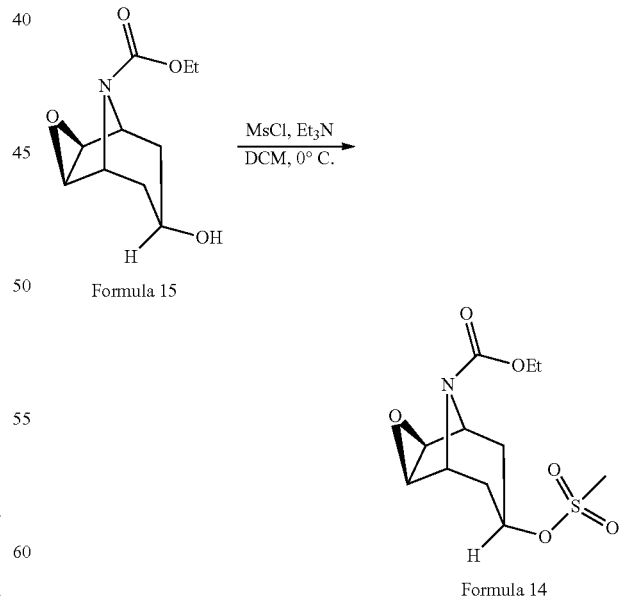

Formula 15

Formula 14

Triethylamine (22.78 g, 225 mmol, 31.4 mL) and mesyl-Cl (23.64 g, 206 mmol, 16.08 mL) was added drop wise to a solution of the compound of Formula 15 (40 g, 188 mmol) in DCM (500 mL) at 0° C. Once the addition was complete, the ice bath was removed and the slightly milky suspension was stirred while warming to room temperature.

After 1 hour a sample was taken and analyzed by TLC which showed full conversion had occurred. The reaction mixture was then washed twice with 500 mL of water. The DCM layer appeared milky and was dried over $Na_2SO_4$ (which made the layer clearer), and then filtered and concentrated under reduced pressure to afford a thick oil. The oil was stripped twice with toluene to afford 54.2 g of a light tan solid which contained 21 w % toluene.

Figure 5:
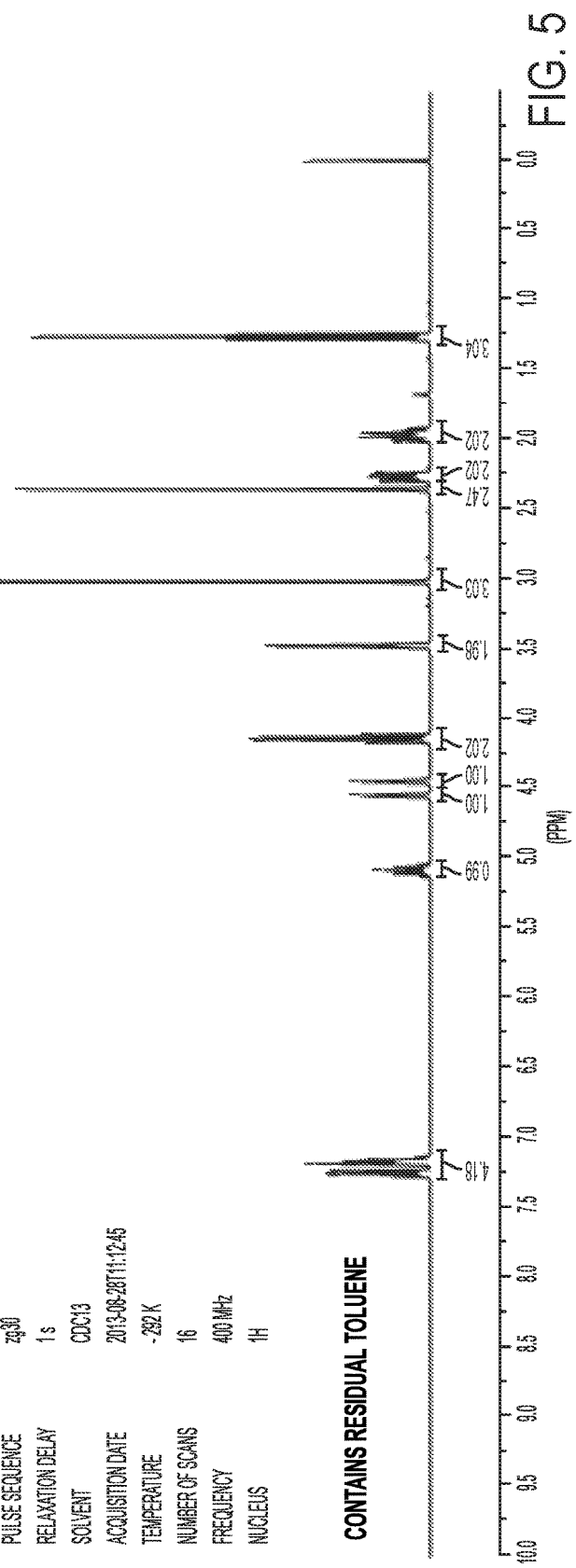
FIG. 5 shows the results of a $^{1H}$NMR analysis of the compound of Formula 14.

The solid was further dried under vacuum at 50° C. until the weight remained constant at 43.2 g (148 mmol; 78.9% yield) yielding a compound of Formula 14 ((1R,2R,4S,5S,7O-ethyl 7-((methylsulfonyl)oxy)-3-oxa-9-azatricyclo[3.3.1.02,4]nonane-9-carboxylate). A sample was taken and the structure was confirmed by $^{1H}$NMR (FIG. 5). $^{1H}$NMR (400 MHz, Chloroform-d) δ 5.11-5.02 (m, 1H), 4.54-4.53 (m, 1H), 4.44-4.43 (m, 1H), 4.13 (q, J=7.1 Hz, 2H), 3.47-3.45 (m, 2H), 3.00 (s, 3H), 2.28-2.23 (m, 2H), 2.00-1.90 (m, 2H), 1.25 (t, J=7.1 Hz, 3H).

The next step proceeded as illustrated in Scheme 6.

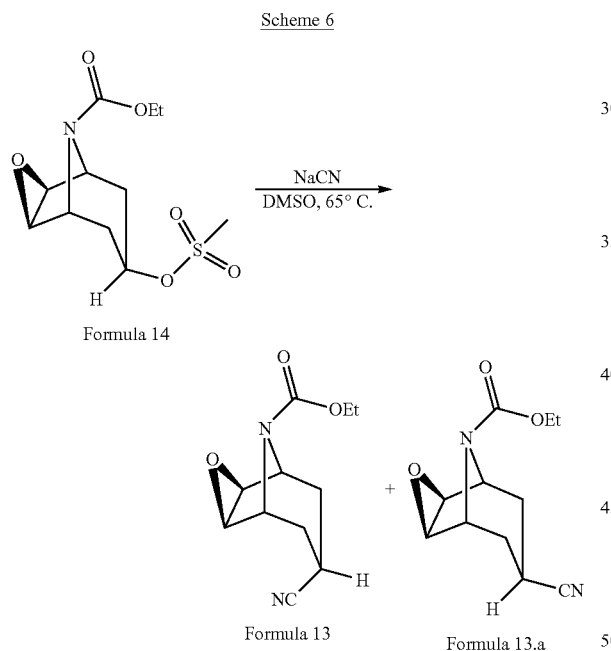

Scheme 6

Potassium cyanide (12.14 g, 186 mmol) and 18-crown-6 (1,4,7,10,13,16-hexaoxacyclooctadecane) (0.493 g, 1.864 mmol) were added to a solution of the compound of Formula 14 (19.89 g, 62.1 mmol, 91%) in 300 mL of dry Dimethyl sulfoxide to form a pale yellow solution which was stirred at 65° C. for two and a half days, or approximately 65 hours, to yield a light brown solution.

A sample was taken and analyzed by TLC (heptane/DME 1:1, molybdate staining required), which showed a clean conversion to the desired product (no exo-epimeric sideproduct observed). However, at this time, it was found that the reaction had not run to completion as starting material was also observed. The stirring was continued for a total of 118 hours, after which the brown solution was allowed to cool to room temperature, and combined with an additional batch before being partitioned between 2 L of EtOAc and 2 L of water.

Figure 6:
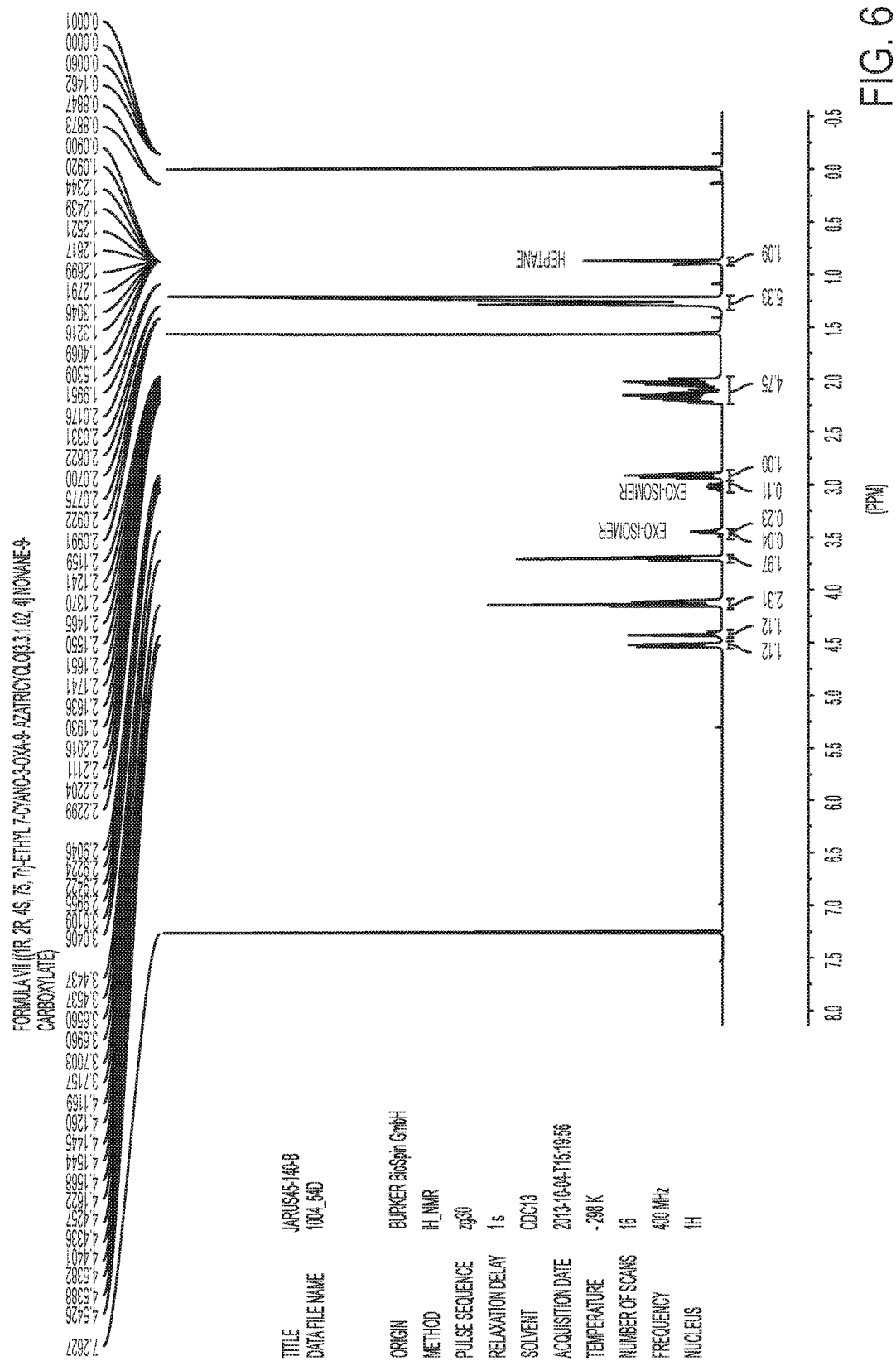
FIG. 6 shows the results of a $^{1H}$NMR analysis of the compound of Formula 13.

The layers were separated and the organic layer was washed twice with 1 L of brine, dried over $Na_2SO_4$, and filtered and concentrated under reduced pressure to afford the crude product, a compound of Formula 13 ((1R,2R,4S,5S,7s)-ethyl 7-cyano-3-oxa-9-azatricyclo[3.3.1.02,4]nonane-9-carboxylate). The product was purified by gravity column chromatography (750 g silica, heptane/[5->50% EtOAc]) to afford 15.1 g of a white solid, or a compound of Formula 13. A sample was taken and analyzed by $^{1H}$NMR (FIG. 6) which demonstrated the product was in agreement with the structure of Formula 13, although the product did contain 10 w % of the exo-sideproduct (which was not problematic for the follow-up reactions) and 7.5 w % of heptane. The combined yield from all experiments was 7.55 g, or 45% yield, after correction for solvent and side product content. $^{1H}$NMR (400 MHz, Chloroform-d) δ 4.53-4.52 (m, 1H), 4.43-4.41 (m, 1H), 4.12 (q, J=7.1 Hz, 2H), 3.70-3.68 (m, 2H), 2.93-2.89 (m, 1H), 2.22-2.12 (m, 2H), 2.04-1.98 (m, 2H), 1.24 (t, J=7.1 Hz, 3H).

The next step proceeded as illustrated in Scheme 7.

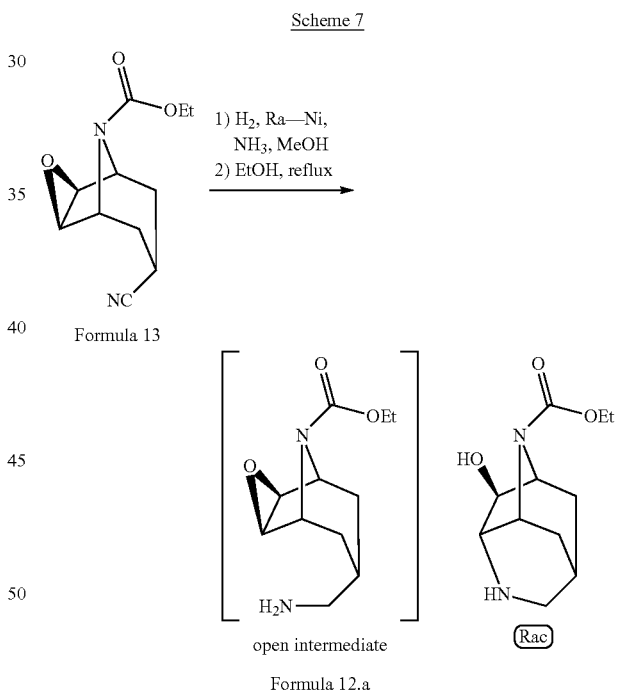

Scheme 7

A 50% slurry of Raney-nickel in water was added to a solution of the compound of Formula 13 (18.20 g, 82 mmol) in 350 mL of MeOH/200 mL of ammonia (7N in MeOH). The solution was kept under a nitrogen atmosphere and the Raney-nickel slurry was added until a dark black suspension was obtained while being stirred vigorously.

The reaction vessel was evacuated and refilled with $H_2$ balloons, which was repeated twice, and then stirred at 45° C. under a $H_2$ atmosphere created by the balloons. After 3 hours, a sample was taken and analyzed by TLC using heptane/dimethoxyethane (DME) 1:1, which demonstrated the reaction was complete. The reaction mixture was filtered over a short pad of celite which was pre-rinsed with MeOH. The residue was also rinsed with additional MeOH.

The filtrate was then concentrated under reduced pressure to give a light yellow oil. This crude product consisted mainly of the open amines of a compound of Formula 12.a (1R,2R,4S,5S,7s)-ethyl 7-(aminomethyl)-3-oxa-9-azatricyclo[3.3.1.02,4]nonane-9-carboxylate and to a lesser extent the (desired) cyclized amine a compound of Formula 12 (rac-(2R,3S,6S,7aS)-ethyl 3-hydroxyoctahydro-1H-2,6-methanopyrrolo[3,2-b]pyridine-1-carboxylate).

To drive cyclization of the main endo-isomer to completion, the intermediate was dissolved in 500 mL of absolute ethanol, which created a light yellow solution, which was then stirred and refluxed overnight.

Figure 7:
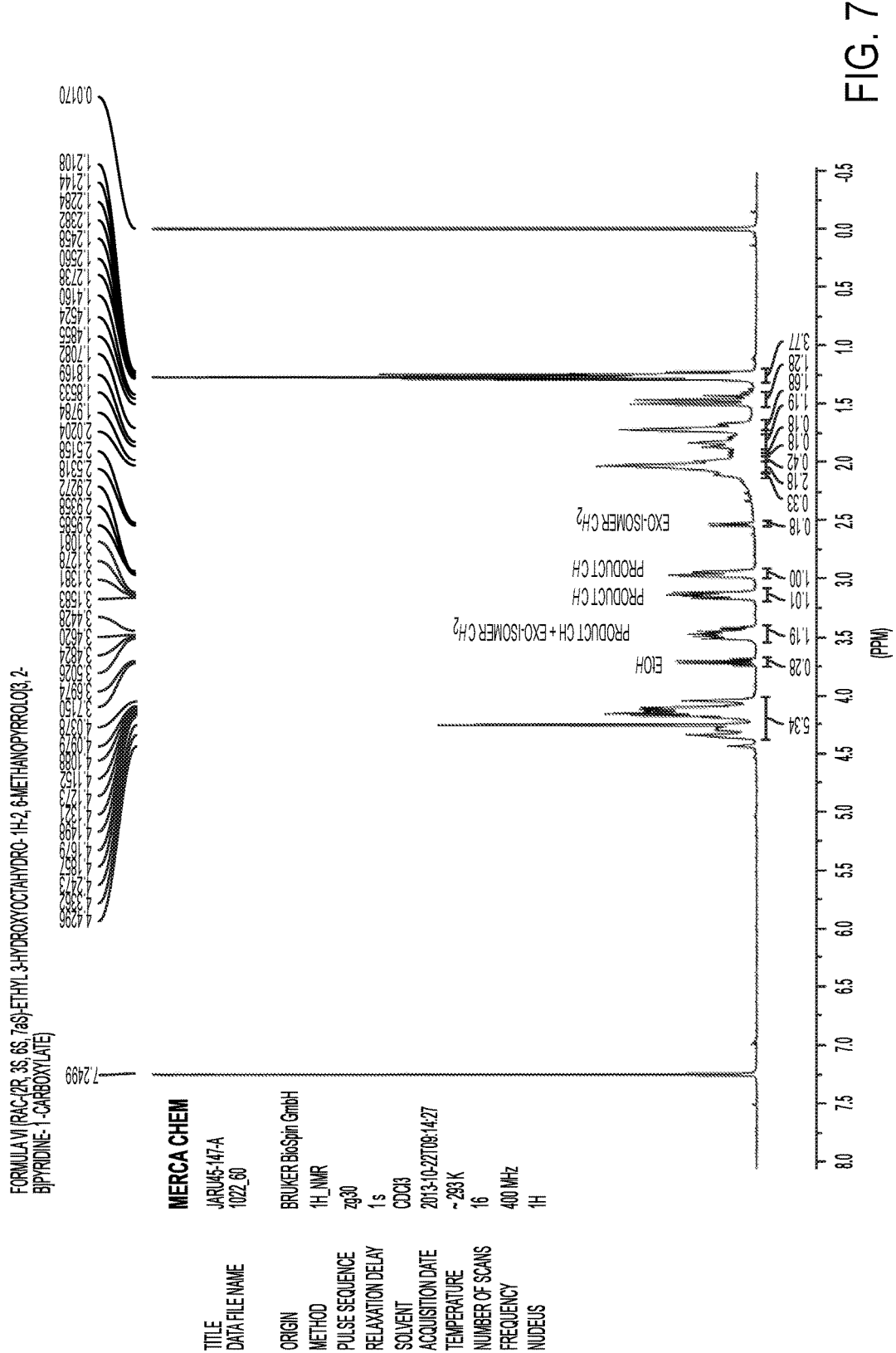
FIG. 7 shows the results of a $^{1H}$NMR analysis of the compound of Formula 12.

A sample was taken, concentrated under reduced pressure, dissolved in CDCl$_3$, and analyzed by $^{1H}$NMR (FIG. 7) which showed the intermediate, open endo-isomer, had cyclized. It was further shown that approximately 9% of the product was open exo-amine, and some solvent remained. $^{1H}$NMR (400 MHz, Chloroform-d) δ 4.46-4.01 (m, 5H), 3.50-3.44 (m, 1H), 3.16-3.11 (m, 1H), 3.96-2.93 (m, 1H), 2.10-1.66 (m, 5H), 1.47 (d, J=13.3 Hz, 1H), 1.26 (t, J=7.1 Hz, 3H).

The main batch, a yellow solution, was concentrated under reduced pressure and the residue was redissolved in 500 mL of CHCl$_3$ and dried over Na$_2$SO$_4$. The solution was filtered and concentrated to give 21.7 g of a compound of Formula 12 as a thick yellow oil which contained solvent and the open exo-amine which was used in the next step.

The next step proceeded as illustrated in Scheme 8.

Scheme 8

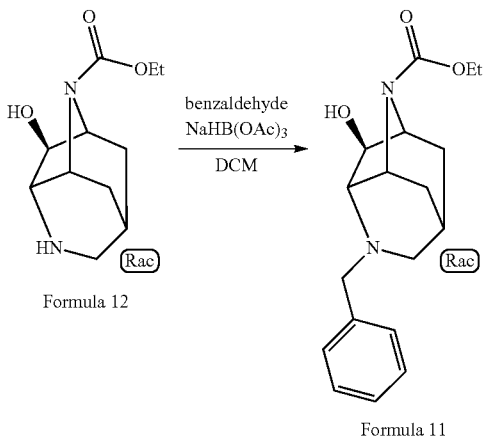

Formula 12

Formula 11

Benzaldehyde (22.74 g, 214 mmol, 21.72 mL) was added to a solution of the compound of Formula 12 (37.3 g, 165 mmol) in 1000 mL of dichloromethane. After 15 minutes STAB (55.9 g, 264 mmol) was added. The suspension was then stirred at room temperature overnight.

Figure 8A:
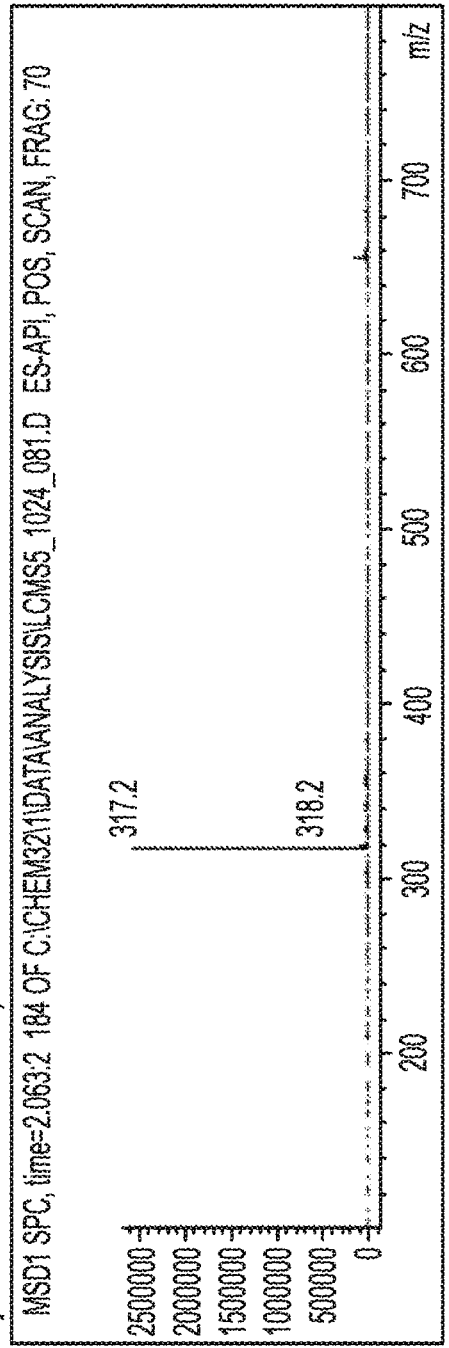
FIGS. 8A and 8B show the results of a structural analysis of the compound of Formula 11.
Figure 8B:
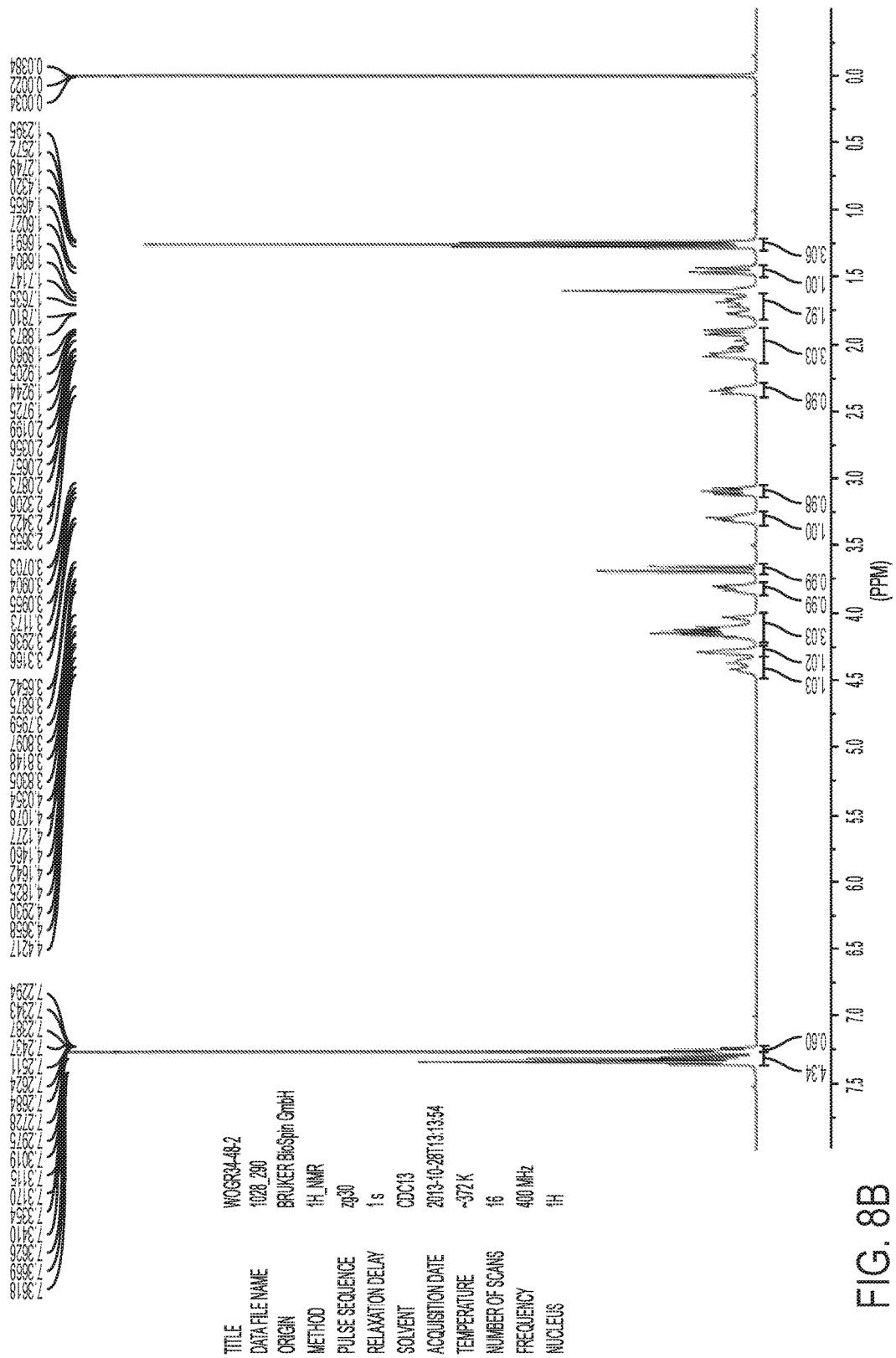

The reaction mixture was washed with 1 L of water and 1 L NaHCO$_3$. The organic layer was dried with Na$_2$SO4$_2$ and concentrated to dryness to afford 55 g of the reacted product, which was next purified by gravity column chromatography (600 g, Hep/5-60% ETOAc) affording: 2.2 g of exo-Bn2N-adduct; and 35.3 g of a compound of Formula 11 (rac-(2R,3S,6S,7aS)-ethyl 3-hydroxyoctahydro-1H-2,6-methanopyrrolo[3,2-b]pyridine-1-carboxylate) as analyzed and confirmed by $^{1H}$ NMR (FIG. 8B) and MS (FIG. 8A). $^{1H}$NMR (400 MHz, Chloroform-d) δ 7.35-7.30 (m, 4H), 7.26-7.22 (m, 2H), 4.41-4.02 (m, 5H), 3.83-3.78 (m, 1H), 3.66 (d, J=13.3 Hz, 1H), 3.30-3.26 (m, 1H), 3.11-3.06 (m, 1H), 2.35-2.31 (m, 1H), 2.07-1.88 (m, 3H), 1.77-1.65 (m, 2H), 1.44 (d, J=13.9 Hz, 1H), 1.25 (t, J=7.1 Hz, 3H).

The next step proceeded as illustrated in Scheme 9.

Scheme 9

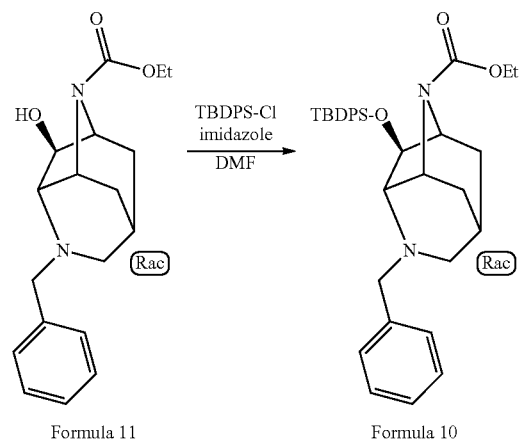

Formula 11

Formula 10

Imidazole (15.19 g, 223 mmol) and tert-butyldiphenylchlorosilane (30.7 g, 112 mmol, 28.7 mL) were added to a solution of the compound of Formula 11 (35.3 g, 112 mmol) in 100 mL of dry N,N-dimethylformamide to form a pale yellow solution which was stirred at room temperature overnight.

After the stirring was complete a sample was taken and analyzed by LCMS which showed the reaction was complete.

The solution was then concentrated under reduced pressure to yield an oily residue which was diluted with 750 mL of DCM and washed with 750 mL of 1:1 saturated aqueous NaHCO$_3$ solution and water. Next the solution was washed with 750 mL of brine. The organic layer was dried over Na$_2$SO$_4$, filtered, and concentrated to afford approximately 65 g of the reacted product as confirmed by TLC.

Figure 9A:
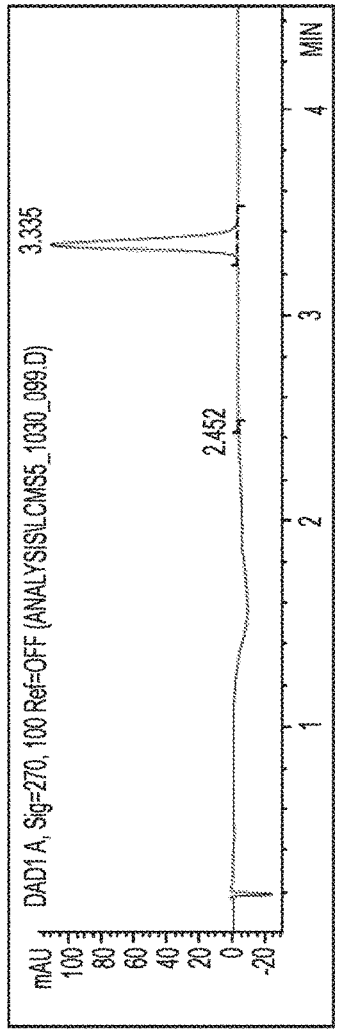
FIGS. 9A and 9B show the results of a structural analysis of the compound of Formula 10.
Figure 9A:
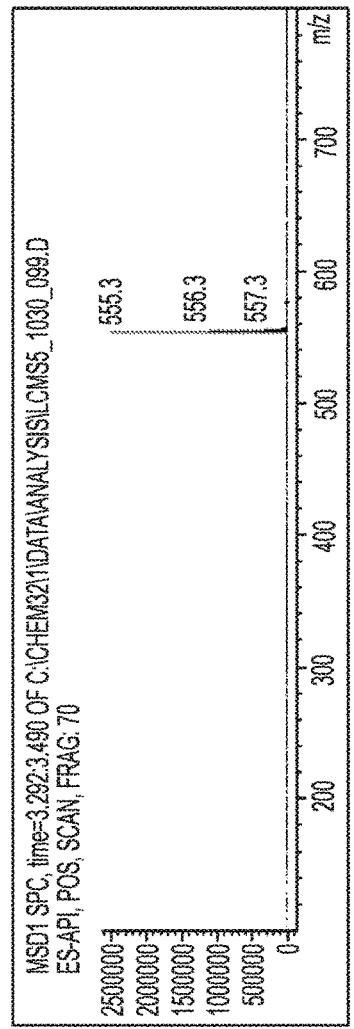
Figure 9B:
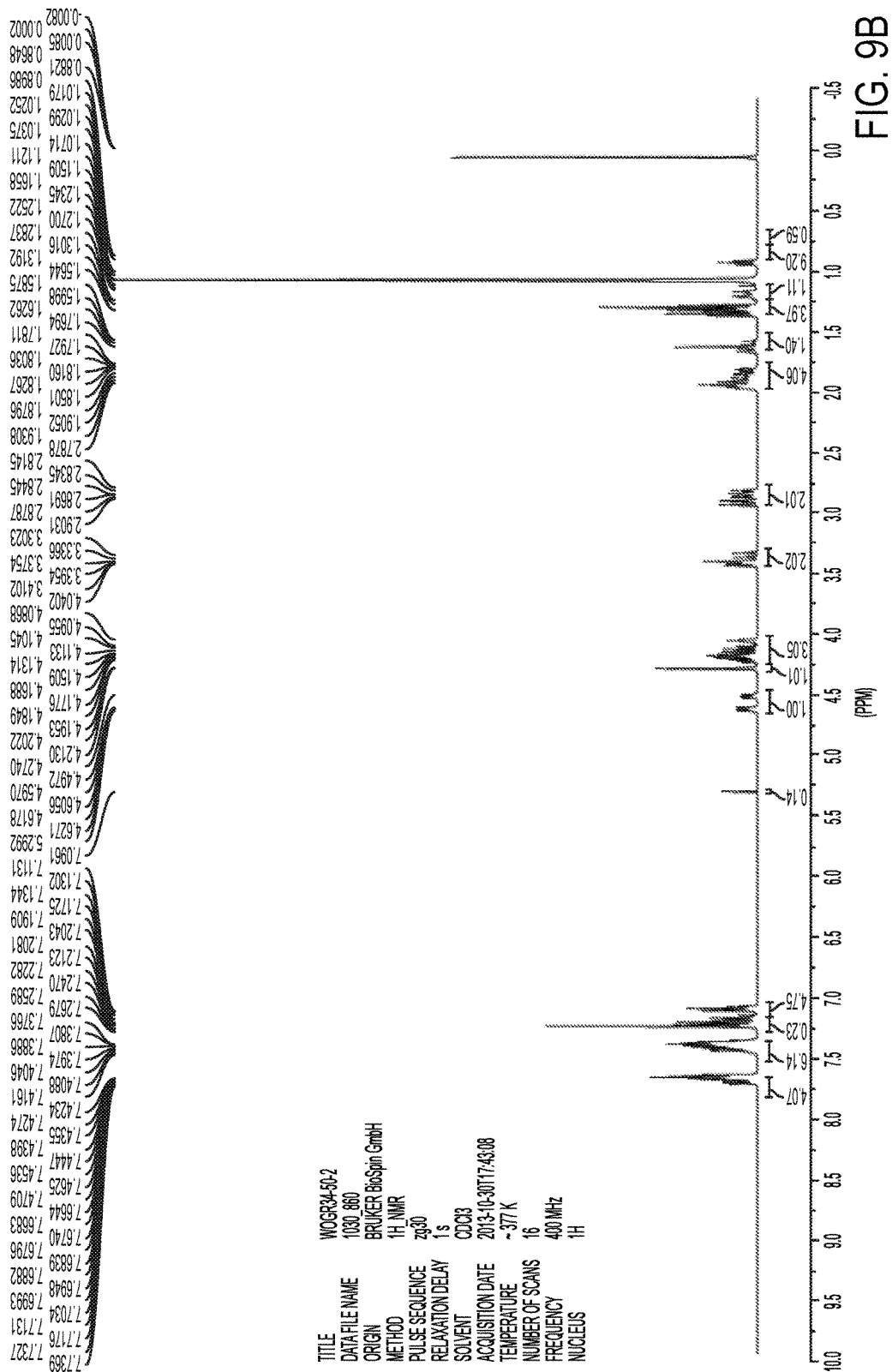

The reacted product was purified by gravity column chromatography (approximately 600 g, Hep/5-15% EtOAc) which afforded 59.5 g, or a 90% yield, of a compound of Formula 10 (rac-(2R,3R,6S,7aS)-ethyl 4-benzyl-3-((tert-butyldiphenylsilyl)oxy)octahydro-1H-2,6-methanopyrrolo[3,2-b]pyridine-1-carboxylate) as a very thick colorless oil. A sample was taken and analyzed by $^{1H}$NMR (FIG. 9B) and LCMS (FIG. 9A), which showed the product was in agreement with the structure of Formula 10 and contained 6 w/w % heptane. $^{1H}$NMR (400 MHz, Chloroform-d) δ 7.72-7.66 (m, 4H), 7.47-7.36 (m, 6H), 7.26-7.16 (m, 3H), 7.12-7.09 (m, 2H), 4.62-4.48 (m, 1H), 4.26 (s, 1H), 4.22-4.03 (m, 3H), 3.40-3.29 (m, 2H), 2.89-2.78 (m, 2H), 1.92-1.76 (m, 4H), 1.62-1.52 (m, 1H), 1.31-1.23 (m, 3H), 1.17-1.11 (m, 1H), 1.02 (s, 9H).

The next step proceeded as illustrated in Scheme 10.

Scheme 10

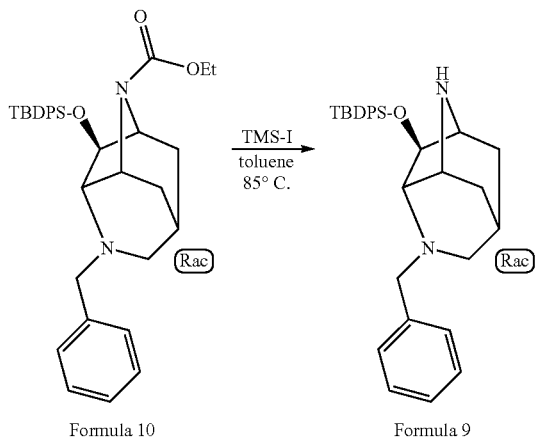

Formula 10 → Formula 9

Iodotrimethylsilane (75.0 g, 375 mmol, 51 ml) was added to a solution of the compound of Formula 10 (73.9 g, 124 mmol, 93%) in 1.2 L of dry toluene to create a yellow reaction mixture which was stirred at 85° C. overnight.

Figure 10:
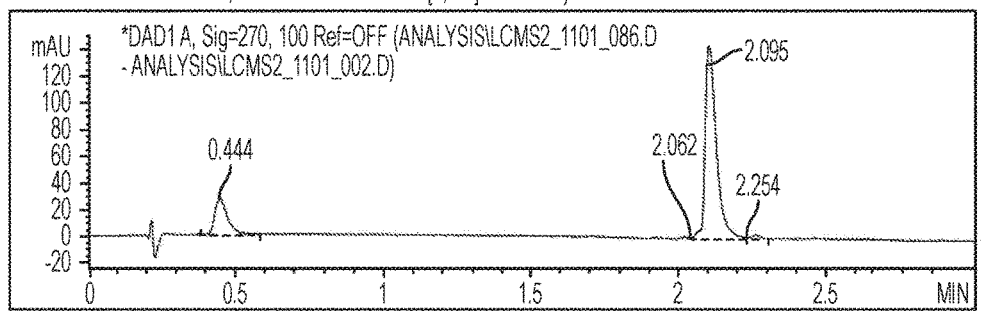
FIG. 10 shows the results of a LCMS analysis of the compound of Formula 9.
Figure 10:
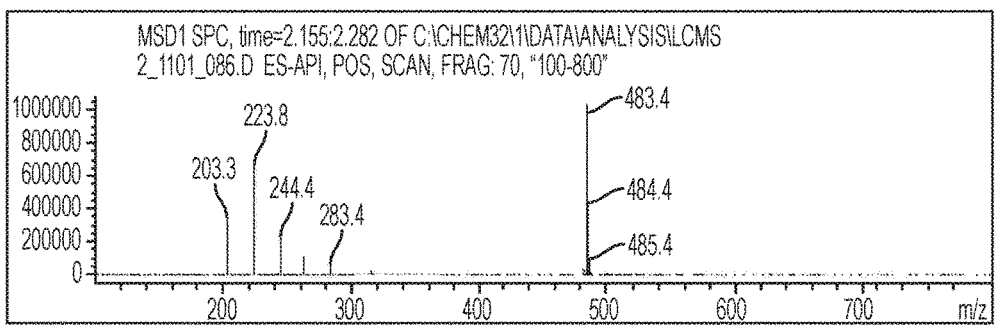
Figure 10:
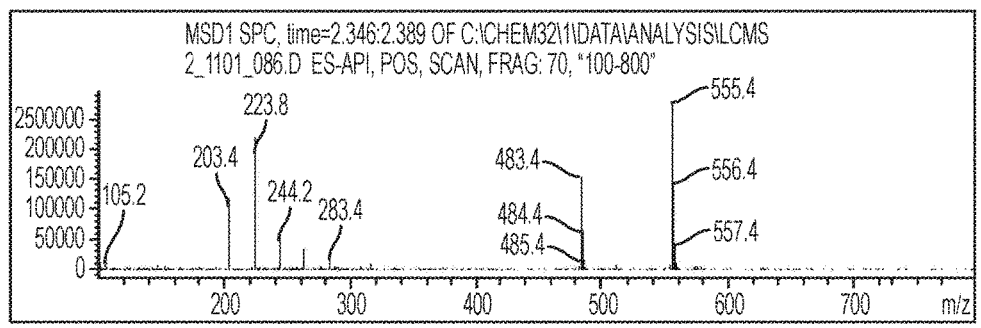

A sample taken then taken and analyzed by TLC, which showed the reaction had gone to completion. The resulting reaction mixture was a dark solution, and was allowed to cool to room temperature (suspension) and quenched with 250 mL of MeOH. The mixture was next concentrated to approximately 250 mL. After which 750 mL of DCM was added and the mixture was washed with 750 mL of 1:1 saturated aqueous $NaHCO_3$ solution/$H_2O$. The organic layer was then washed with 750 mL of brine, dried over $Na_2SO_4$, filtered, and concentrated under reduced pressure to afford approximately 72 g, or a 92% yield, of a compound of Formula 9 (rac-(2R,3R,6S,7aS)-4-benzyl-3-((tert-butyldiphenylsilyl)oxy) octahydro-1H-2,6-methanopyrrolo[3,2-b]pyridine) as a dark yellow/orange oil. A sample was taken and analyzed by LCMS (FIG. 10) which showed the correct mass, and that the product had a purity of about 80%, with the peak at 0.448 being toluene. $^{1H}$NMR (400 MHz, Chloroform-d) δ 7.69-7.63 (m, 4H), 7.47-7.37 (m, 6H), 7.26-7.12 (m, 5H), 4.36 (s, 1H), 3.73-3.70 (m, 1H), 3.39 (d, J=13.7 Hz, 1H), 3.26 (d, J=7.6 Hz, 1H), 3.06 (s, 1H), 2.90 (d, J=13.7 Hz, 1H), 2.79-2.74 (m, 1H), 2.41 (bs, 1H), 1.90-1.80 (m, 4H), 1.67-1.64 (m, 1H), 1.11-0.99 (m, 10H).

The next step proceeded as illustrated in Scheme 11.

Scheme 11

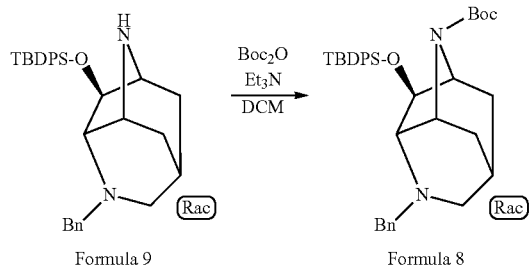

Formula 9 → Formula 8

Et$_3$N (48.3 g, 477 mmol, 0.067 L) and di-tert-butyl dicarbonate (Boc$_2$O) (39.1 g, 179 mmol) was added to a solution of the compound of Formula 9 (72 g, 119 mmol, 80%) in 1 L of dichloromethane to form a light yellow solution which was stirred at room temperature over weekend.

A sample taken and analyzed by TLC which showed the reaction was complete. The solution was diluted with 250 mL of DCM and washed with 1 L of saturated aqueous $NaHCO_3$ solution and 1 L of brine. The organic layer was then dried over $Na_2SO_4$, filtered, and concentrated to afford approximately 80 g of the crude product.

Purification by gravity column chromatography (800 g, heptane/[EtOAc 1->10%]) afforded 68.4 g, or a 94% yield, of a compound of the Formula 8 (rac-(2R,3R,6S,7aS)-tert-butyl 4-benzyl-3-((tert-butyldiphenylsilyl)oxy)octahydro-1H-2, 6-methanopyrrolo[3,2-b]pyridine-1-carboxylate) as a colorless glass.

Figure 11A:
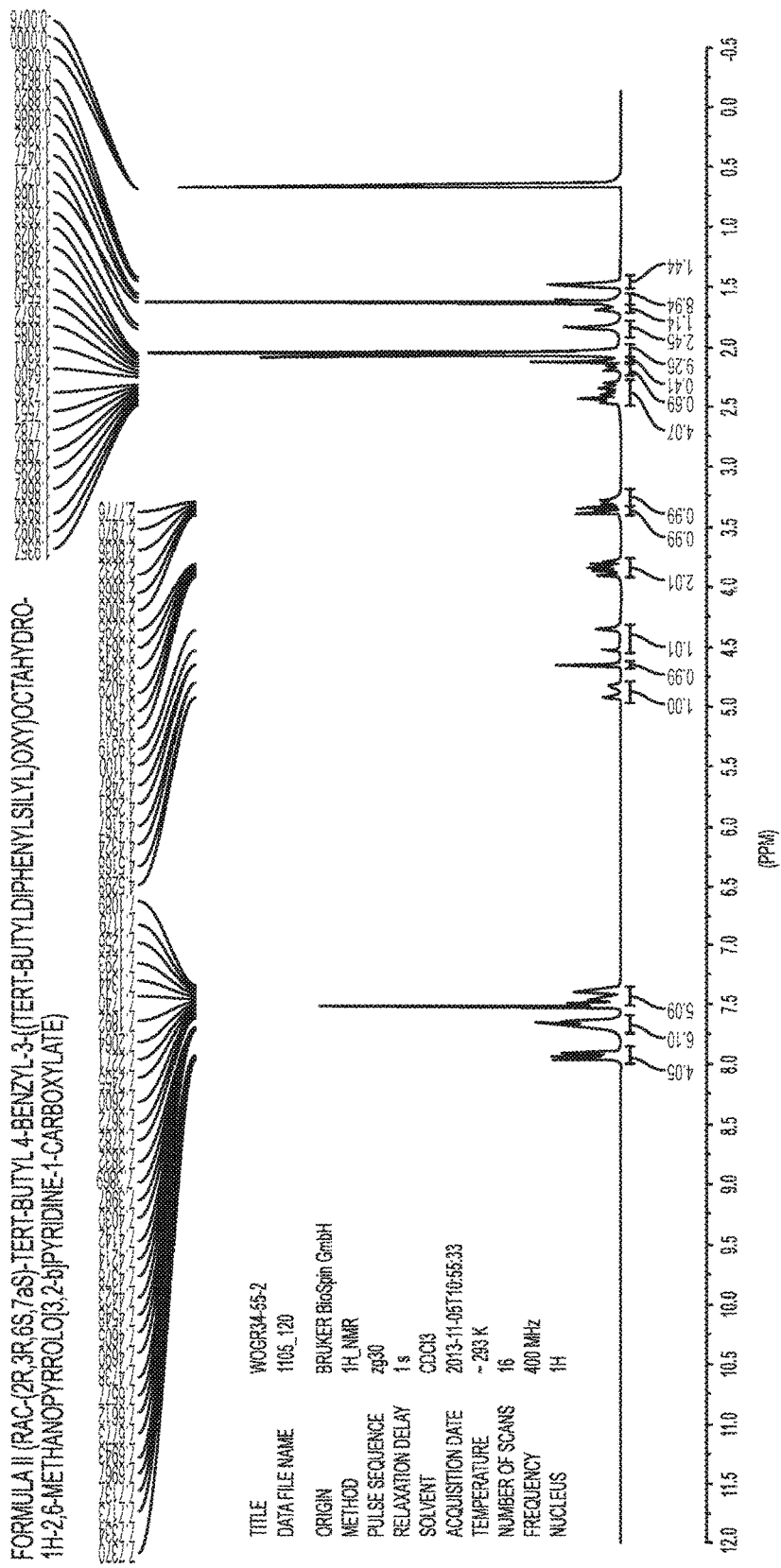
FIGS. 11A and 11B show the results of a structural analysis of the compound of Formula 8.
Figure 11B:
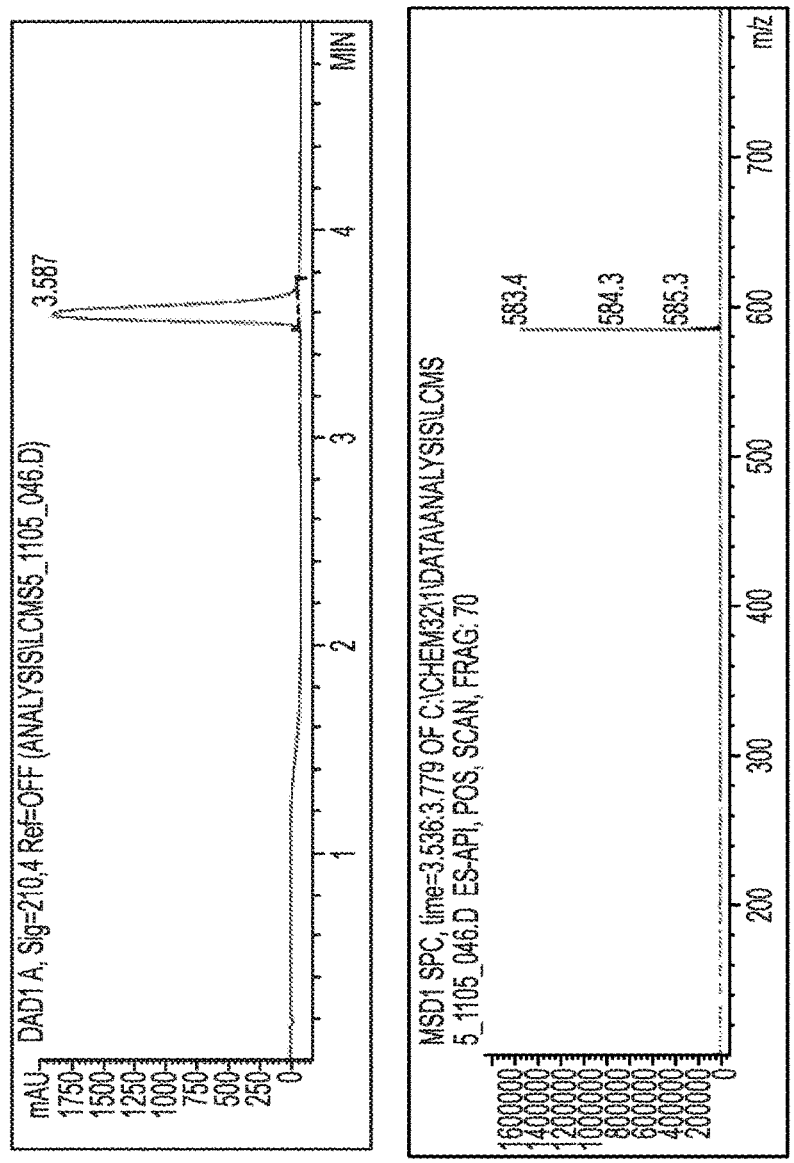

A sample was taken and analyzed by $^{1H}$NMR (FIG. 11A) and LCMS (FIG. 11B) which showed agreement between the product and the structure of Formula 8, and further showing that the product contained 4 w/w % heptane. $^{1H}$NMR (400 MHz, Chloroform-d) δ 7.73-7.65 (m, 4H), 7.47-7.35 (m, 6H), 7.24-7.10 (m, 5H), 4.53-4.40 (m, 1H), 4.24 (d, J=3.8 Hz, 1H), 4.10-3.92 (m, 1H), 3.44-3.32 (m, 2H), 2.87 (d, J=13.6 Hz, 1H), 2.33-2.77 (m, 1H), 1.93-1.72 (m, 4H), 1.65-1.54 (m, 1H), 1.50-1.47 (m, 9H), 1.10-1.02 (m, 10H).

The next step proceeded as illustrated in Scheme 12.

Scheme 12

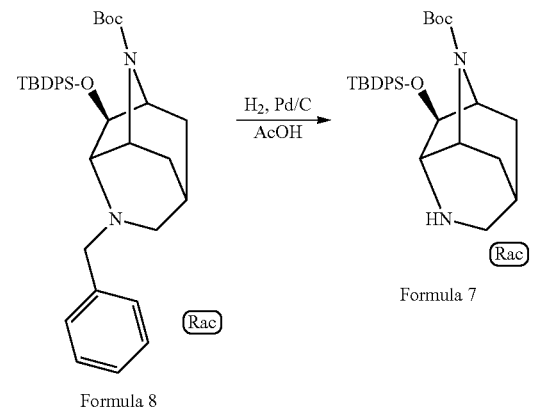

Formula 8 → Formula 7

Under a nitrogen flow, Palladium, 10% on activated carbon (7 g, 125 mmol) was added to a solution of the compound of Formula 8 (72.9 g, 125 mmol) in 600 mL of acetic acid. The vessel was closed and the resulting mixture was stirred at 50° C. for 2 hours under a hydrogen atmosphere created by a balloon.

The mixture was then stirred at 50° C. overnight. The black suspension was filtered over EtOH rinsed celite and the filtrate was concentrated under reduced pressure. The residue was stripped twice with 0.5 L of toluene, after which it was dissolved in 1 L of diethyl ether.

The organic layer was then washed with 1 L of 10% (w/v) aqueous $K_2CO_3$ solution, 1 L of brine, dried over $Na_2SO_4$, filtered, and concentrated under reduced pressure before being stripped again with pentane to afford 58.5 g of a thick tan syrup, a compound of Formula 7 (rac-(2R,3S,6S,7aS)-tert-butyl 3-((tert-butyldiphenylsilyl)oxy)octahydro-1H-2,6-methanopyrrolo[3,2-b]pyridine-1-carboxylate).

Figure 12A:
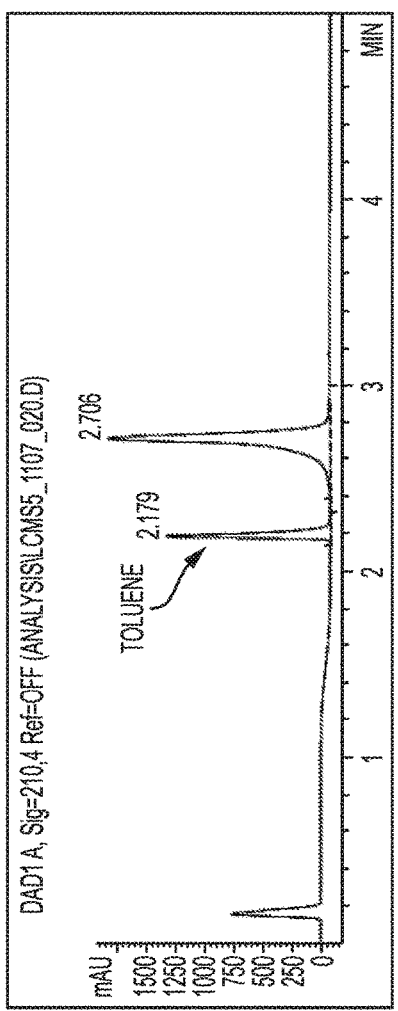
FIGS. 12A and 12B show the results of a structural analysis of the compound of Formula 7.
Figure 12A:
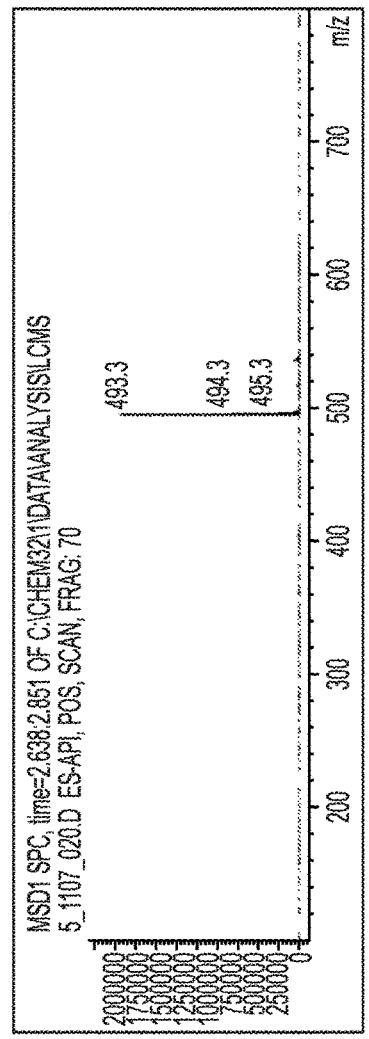
Figure 12B:
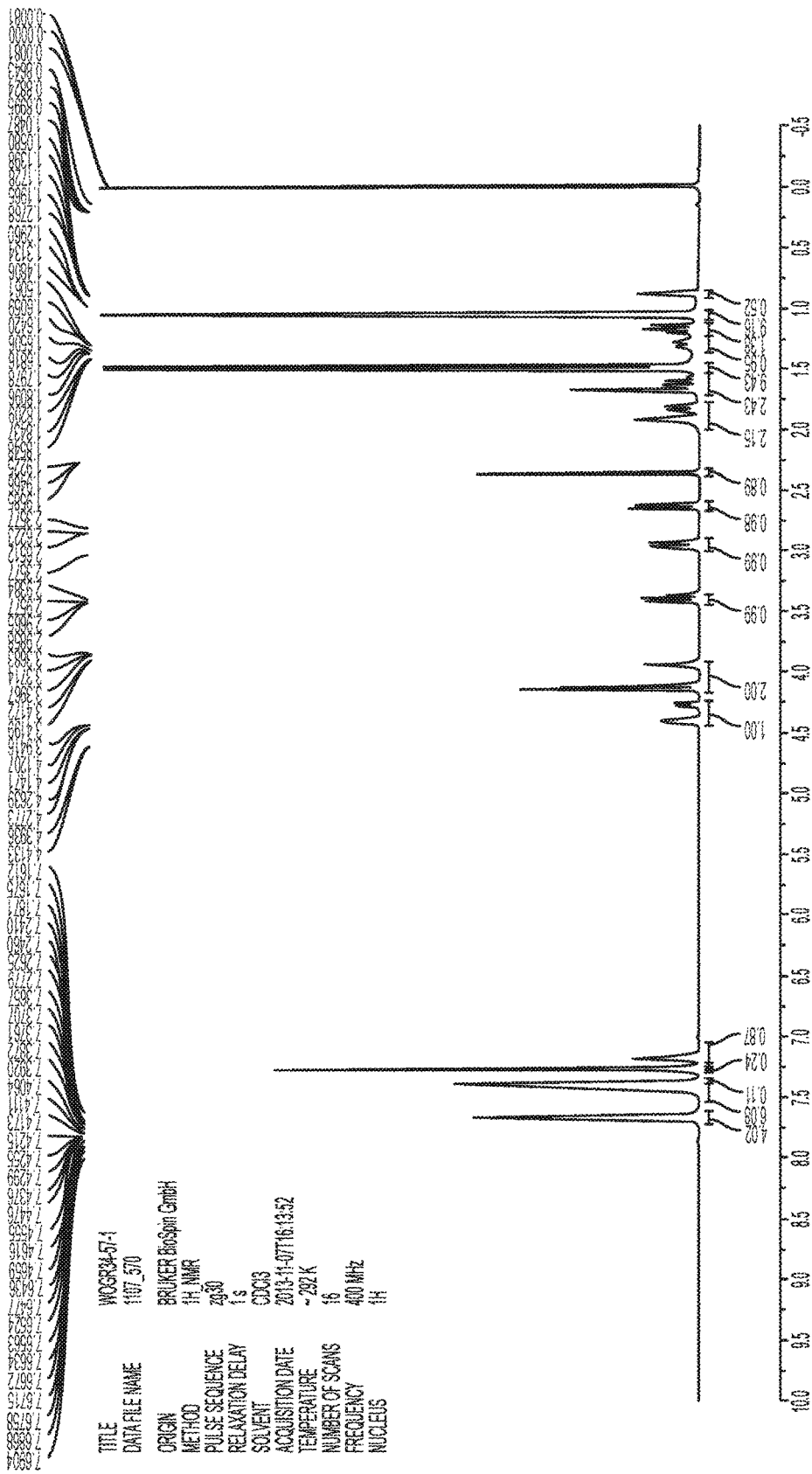

A sample was taken and analyzed by $^{1H}$NMR (FIG. 12B) and LCMS (FIG. 12A) which showed the product was in agreement with structure of Formula 7 and contained 5.1 weight % of toluene and 1.3 weight % of n-pentane. $^{1H}$NMR (400 MHz, Chloroform-d) δ 7.68-7.63 (m, 4H), 7.45-7.35 (m, 6H), 4.40-4.25 (m, 1H), 4.13-3.93 (m, 2H), 3.41-3.36 (m, 1H), 2.97-2.92 (m, 1H), 2.62 (d, J=11.5 Hz, 1H), 1.96-1.78 (m, 2H), 1.67 (s, 1H), 1.64-1.56 (m, 1H), 1.49-1.47 (m, 9H), 1.16-1.13 (m, 1H), 1.05-1.04 (m, 9H).

The compound of Formula 7 was separated into its respective enantiomers via supercritical fluid chromatography (SFC) on a Welkho-1 column with 90/10 scCO$_2$/iPrOH+ 0.2% isopropylamine eluent as as illustrated in Scheme 13.

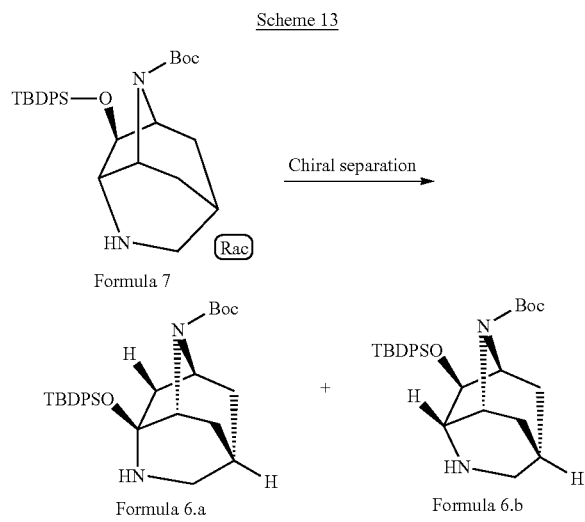

The next step proceeded as illustrated in Scheme 14.

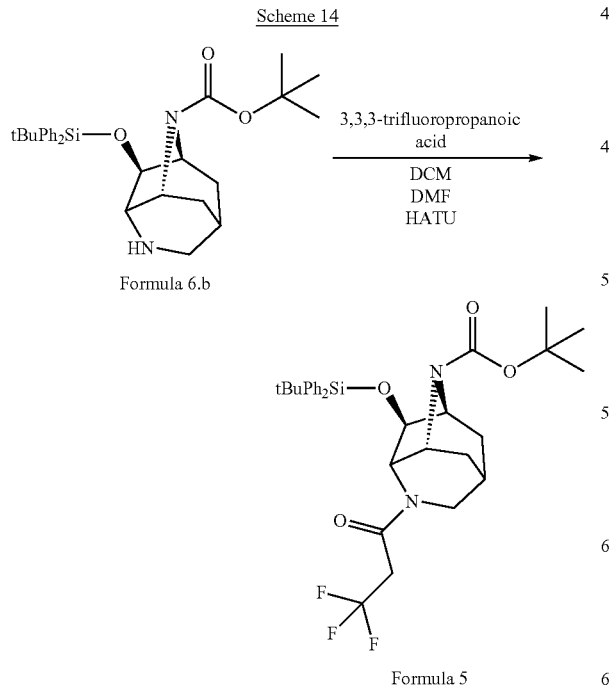

3,3,3-trifluoropropanoic acid (3.629 mL, 41.1 mmol, 1.5 eq) was dissolved in DCM (120 mL) and dry DMF (10 mL). DIPEA (7.16 mL, 41.1 mmol, 1.5 eq) and HATU (1-[bis (dimethylamino)methylene]-1H-1,2,3-triazolo[4,5-b]pyridinium 3-oxidhexafluorophosphate) (15.63 g, 41.1 mmol, 1.5 eq) were added and the mixture was stirred at room temperature for 1.5 hours. This resulted in the formation of a clear red-brown solution.

To that solution, a solution of the compound of Formula 6.b (13.5 g, 27.4 mmol) in DCM (100 mL) was added and the solution was stirred for at room temperature for 4 hours.

The reaction mixture was diluted with DCM (250 mL), washed with aqueous 1 M KHSO$_4$ (400 mL), saturated aqueous NaHCO$_3$ (400 mL), water (400 mL), brine (250 mL), dried over Na$_2$SO$_4$ and concentrated in vacuo to afford 22.74 g (>100%) a compound of Formula 5 ((2S*,3S*,3aS*, 6R*,7aR*)-tert-butyl 3-((tertbutyldiphenylsilyl)oxy)-4-(3,3, 3trifluoropropanoyl)octahydro-1H-2,6-methanopyrrolo[3,2-b]pyridine-1-carboxylate) as a brown oil.

The next step proceeded as illustrated in Scheme 15.

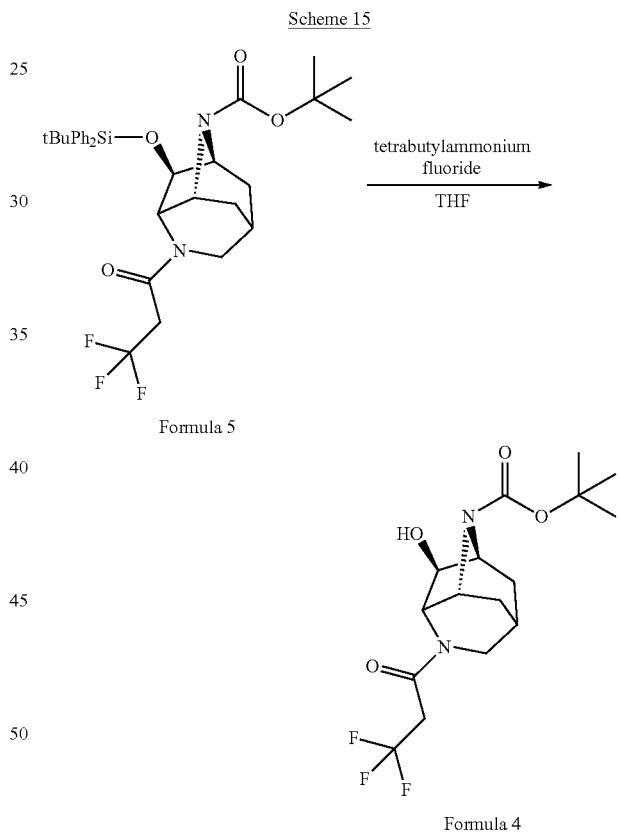

The compound of Formula 5 (max 27.4 mmol) was dissolved in dry THF (115 mL).

A solution of tetrabutylammonium fluoride in THF (1 M, 82 mL, 82 mmol) was added and the reaction mixture was stirred at 50° C. overnight. LCMS analysis revealed complete conversion to desired material.

The solution was concentrated in vacuo and co-evaporated twice with 50% EtOAc/heptane (2×, each 100 mL) to afford 38.66 g of crude material as a brown oil. The material was dissolved in 25% EtOAc/Et$_2$O (800 mL) and washed with water (2×, each 600 mL). The aqueous layers were combined and extracted with 25% EtOAc/Et2O (400 mL).

The organic layers were combined, washed with brine (400 mL), dried over Na₂SO₄ and concentrated in vacuo to afford 15.14 g of material as a brown oil.

Purification by gravitation column chromatography (gradient 50% EtOAc/heptane to 100% EtOAc) yielded 5.85 g of a compound of Formula 4 ((2S*,3S*,3aS*,6R*,7aR*)-tert-butyl 3-hydroxy-4-(3,3,3-trifluoropropanoyl)octahydro-1H-2,6-methanopyrrolo[3,2-b]pyridine-1-carboxylate) (58% over 2 steps) as a white foam.

The next step proceeded as illustrated in Scheme 16, to dryness to yield 6.8 g of crude material. Purification by flash column chromatography (EtOAc/heptane gradient) afforded 5.49 g (76%) of a compound of Formula 3 ((2S*,3S*,3aS*,6R*,7aR*)-tert-butyl 3-(pivaloyloxy)-4-(3,3,3-trifluoropropanoyl)octahydro-1H-2,6-methanopyrrolo[3,2-b]pyridine-1-carboxylate) as a white foam. LCMS analysis: purity>95%, found 449.3 [M+H]+ & 393.2 (M-(C4H8)+H]+).

The next step proceeded as illustrated in Scheme 17.

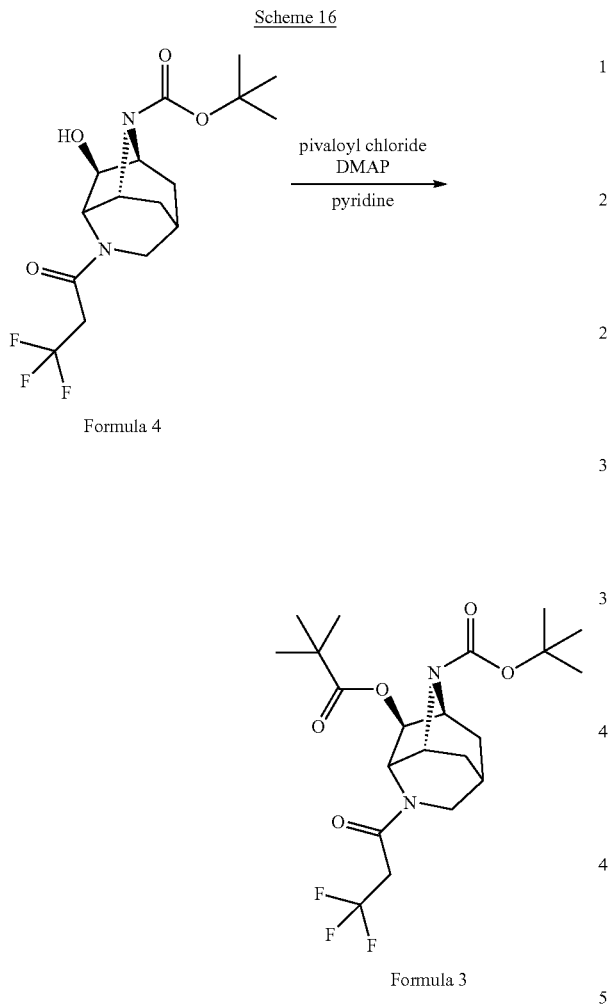

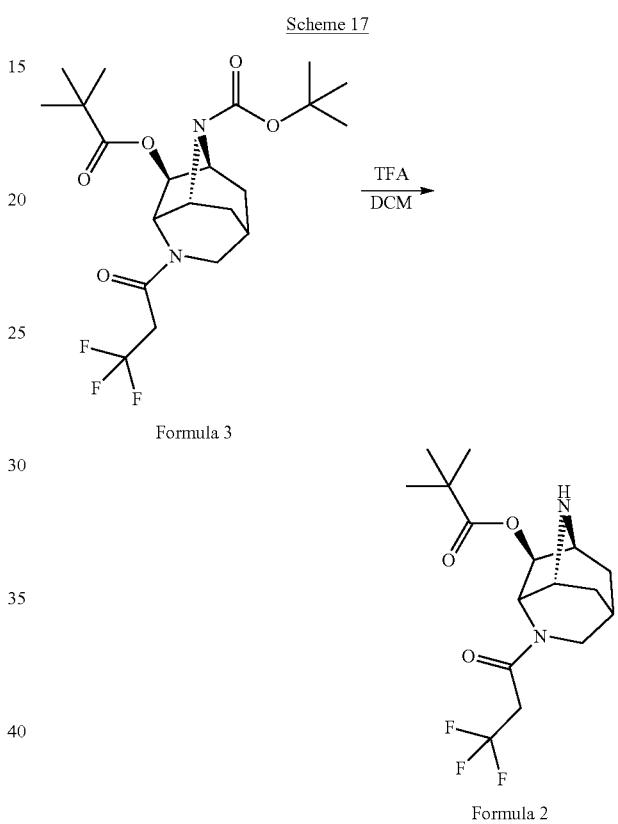

The compound of Formula 4 (5.85 g, 16 mmol) was dissolved in pyridine (50 mL), followed by the addition of DMAP (dimethylaminopyridine) (1.96 g, 16.06 mmol) and pivaloyl chloride (3.95 mL, 32.1 mmol).

The reaction mixture was stirred overnight at 60° C. LCMS analysis revealed complete conversion to desired material. The reaction mixture was allowed to cool to room temperature (a light brown suspension formed) and concentrated in vacuo.

The residue was diluted with EtOAc (250 mL) and washed with aqueous 0.5 M KHSO₄ (200 mL) and saturated aqueous NaHCO₃ (250 mL). Each time the aqueous layer was extracted with additional EtOAc (50 mL).

The combined organic layers were washed with brine (200 mL), dried with sodium sulfate, filtered and evaporated The compound of Formula 3 (1 g, 2.23 mmol) was dissolved in DCM (20 mL).

TFA (trifluoroacetic acid) (8.54 mL, 111 mmol) was added and the mixture was stirred at room temperature for 1 h. LCMS analysis revealed complete conversion to desired material.

The reaction mixture was concentrated in vacuo and co-evaporated with toluene (2×, each 20 mL). The residue was dissolved in chloroform (40 mL) and washed with aqueous saturated Na₂CO₃ solution (40 mL). The aqueous phase was extracted with chloroform (3×, each 20 mL).

Figure 13:
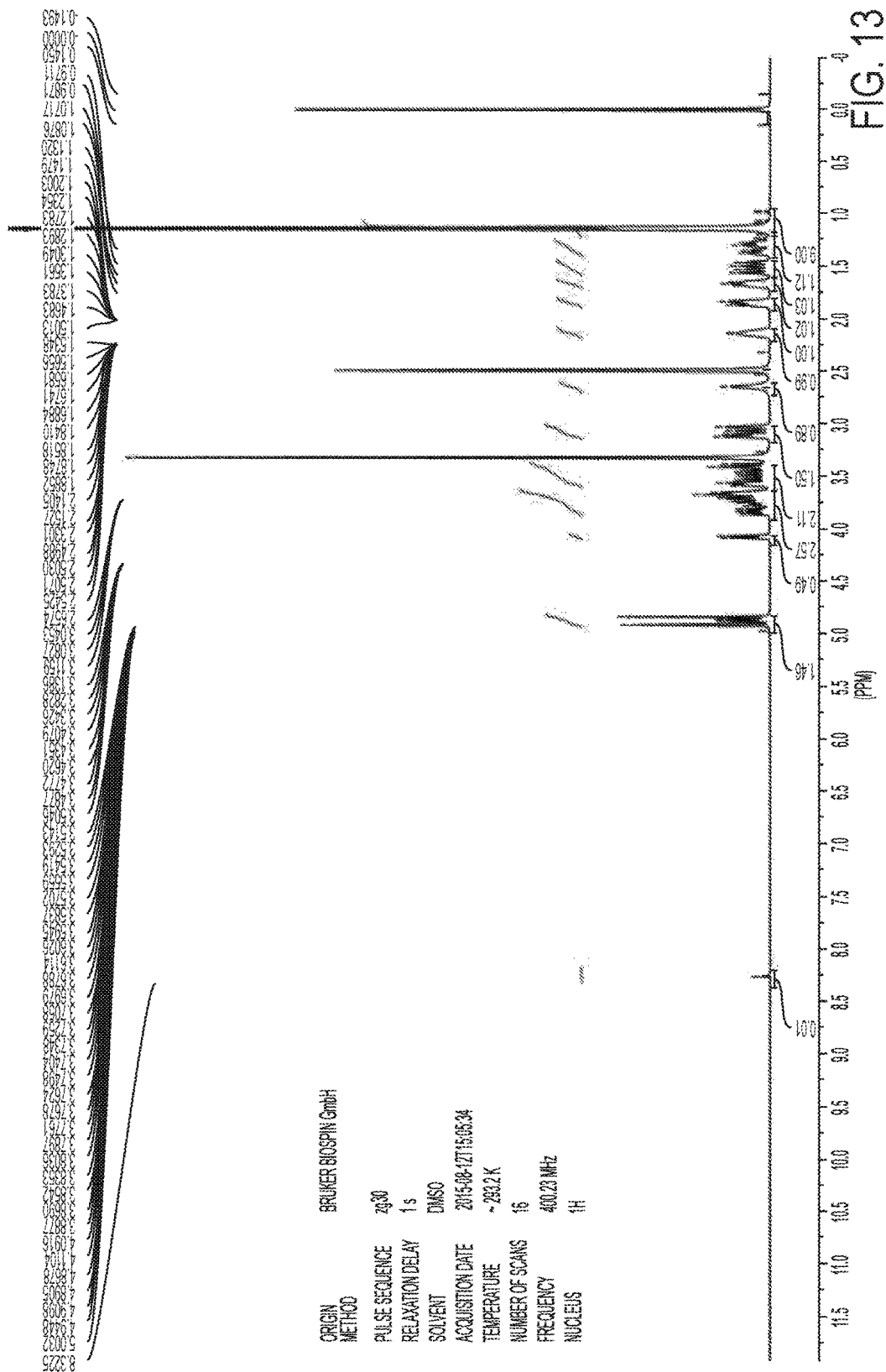
FIG. 13 shows the results of a $^{1H}$NMR analysis of the compound of Formula 2.

The organic layers were combined, washed with brine (70 mL), dried (Na₂SO₄), filtered and evaporated under reduced pressure to afford 769.9 mg (99%) of a compound of Formula 2 ((2S*,3S*,3aS*,6R*,7aR*)-4-(3,3,3-trifluoropropanoyl)octahydro-1H-2,6-methanopyrrolo[3,2-b]pyridin-3-ylpivalate) as an off-white solid. The structure was confirmed by ¹H NMR analysis as shown in FIG. 13.

The next step proceeded as illustrated in Scheme 18,

Scheme 18

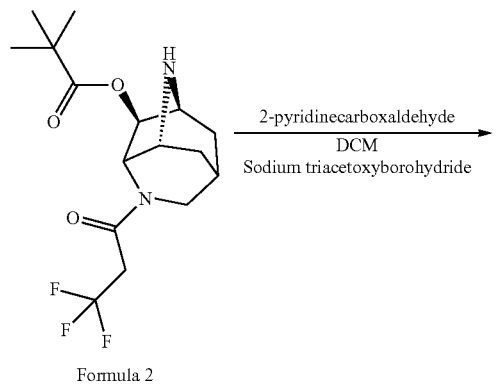

Formula 2

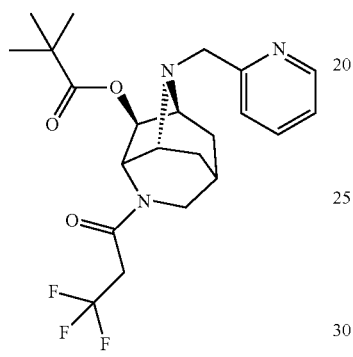

Formula 1

The compound of Formula 2 (693.8 mg, 1.99 mmol) was dissolved in DCM (20 mL).

2-pyridinecarboxaldehyde (284 µL, 2.99 mmol) was added and the mixture was stirred for 2 hours. Sodium triacetoxyborohydride (696 mg, 3.29 mmol) was then added and the mixture was stirred overnight at room temperature.

LCMS analysis revealed complete conversion to desired material. The mixture was concentrated in vacuo. The residue was dissolved in chloroform (40 mL) and washed with aqueous saturated $Na_2CO_3$ solution (40 mL). The aqueous phase was extracted with chloroform (3×, each 20 mL). The organic layers were combined, washed with brine (70 mL), dried (Na2SO4), filtered and evaporated under reduced pressure to afford crude material.

Figure 14:
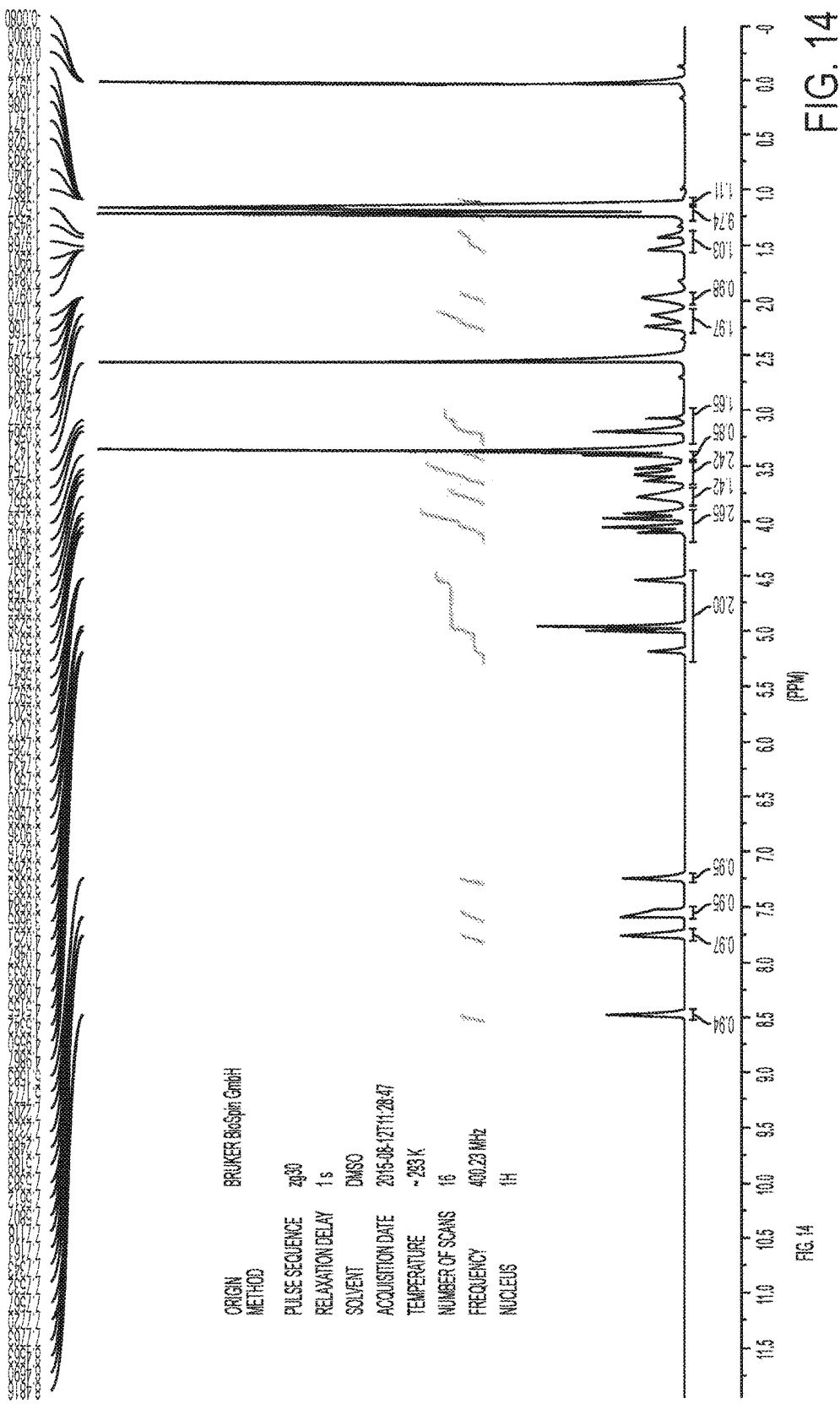
FIG. 14 shows the results of a $^{1H}$NMR analysis of the compound of Formula 1.

Purification by column chromatography (silica, gradient 14% EtOAc/heptane to 100% EtOAc) afforded 718 mg of an oily material. The oil was dissolved in EtOAc (~10 mL) and filtered over a paper filter, concentrated in vacuo again and co-evaporated successively with acetonitrile, pentane and $Et_2O$ to afford 658 mg (75%) of a compound of Formula 1 ((2S*,3S*,3aS*,6R*,7aR*)-1-(pyridin-2-ylmethyl)-4-(3,3,3-trifluoropropanoyl)octahydro-1H-2,6-methanopyrrolo[3,2-b]pyridin-3-ylpivalate) as a foam. The structure was confirmed by $^{1H}$NMR analysis as shown in FIG. 14, and the absolute stereochemistry was confirmed by x-ray analysis.

An overview of these synthetic steps to transform the starting reactant into a compound of Formula 1 is provided in Scheme 19, below.

Scheme 19

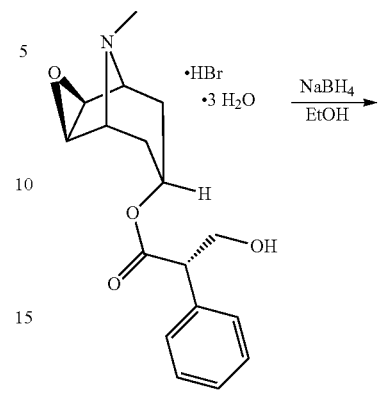

Formula 19 (Scopolamine)

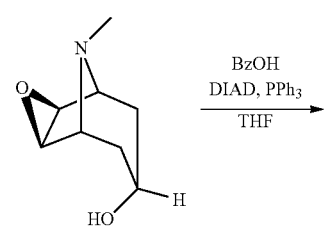

Formula 18

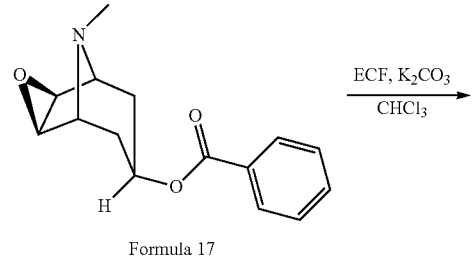

Formula 17

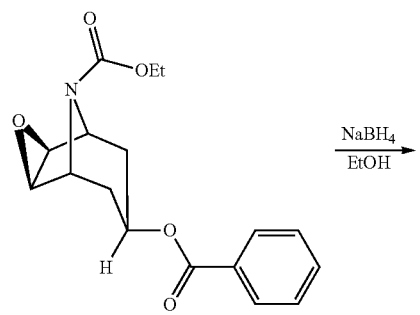

Formula 16

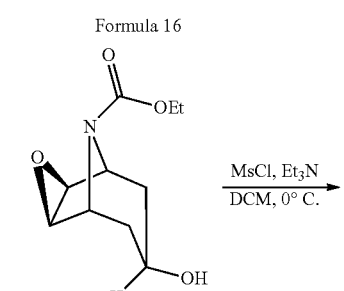

Formula 15

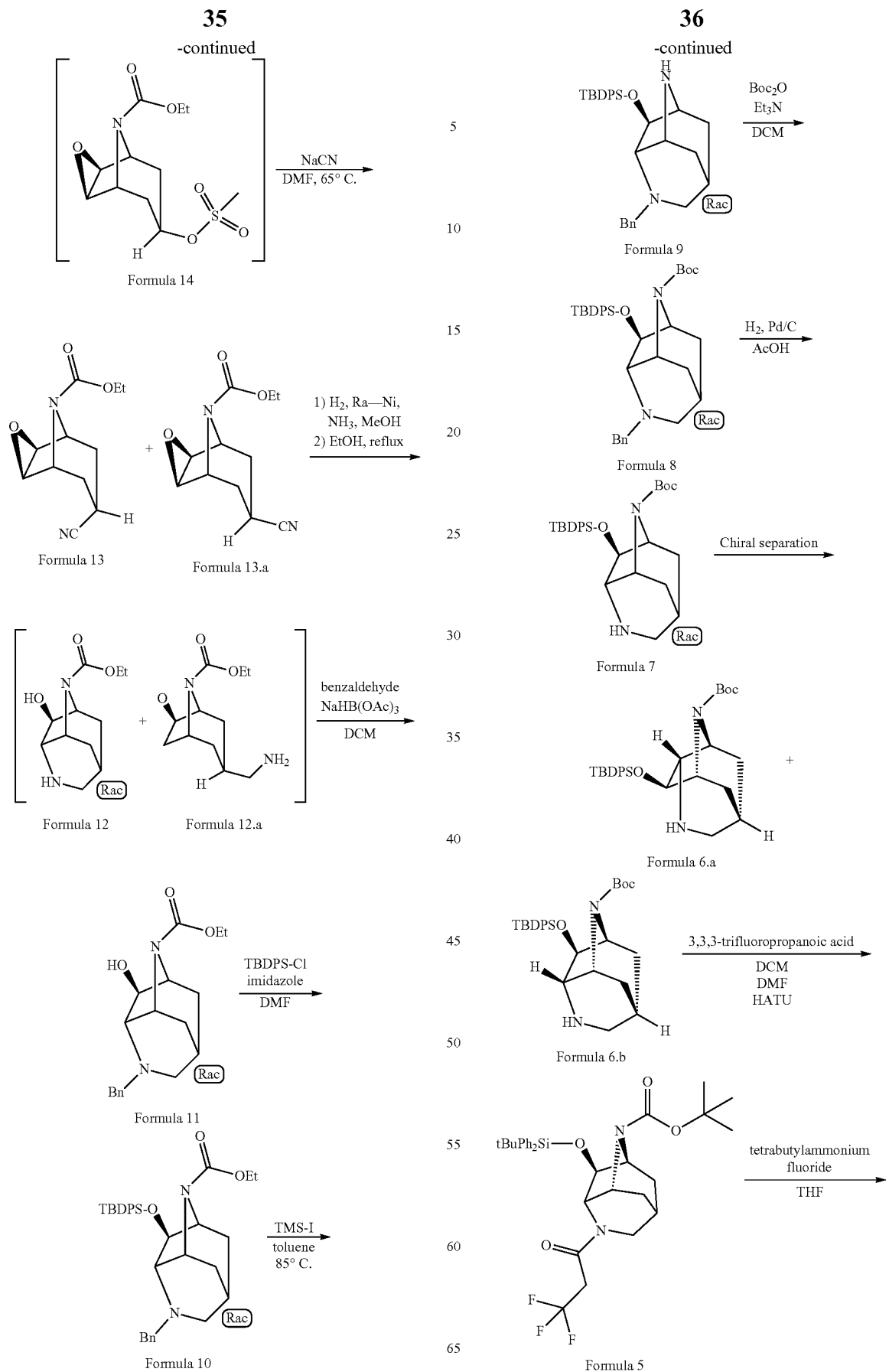

-continued

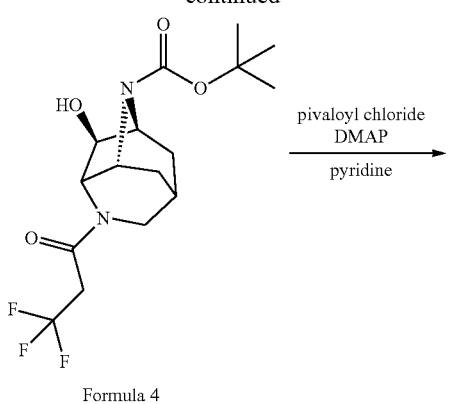

Formula 4

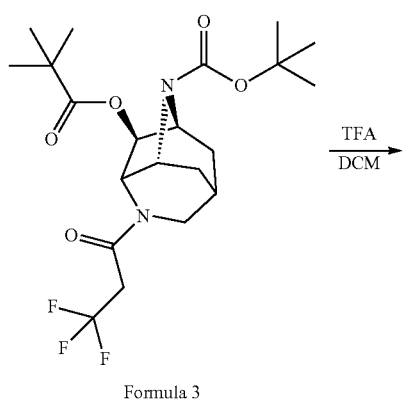

Formula 3

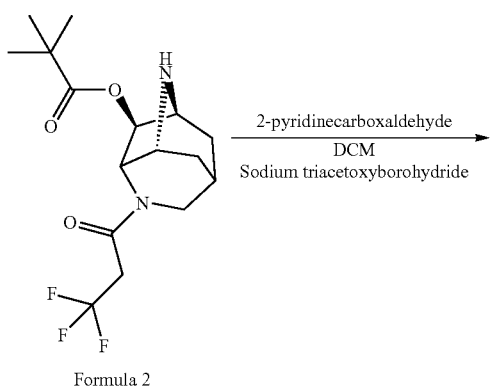

Formula 2

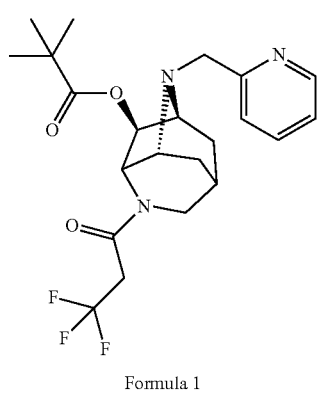 [SMILES: CC(C)(C)C(=O)O[C@@H]1C2[C@H]3CC(C[C@@H]1N3Cc1ccccn1)CN2C(=O)CC(F)(F)F]

Formula 1

EXAMPLE 2

Non-Opiod, Non-NSAID Mode of Action

The Taxol model was used in order to investigate the MoA of Formula 1.

Animals showing chemotherapy-induced pain following repeated doses of taxol were treated with either vehicle gabapentin or Formula 1. Plasma was collected following the first dose of the test items and after 7 days of daily treatment. Skin from hind paws were also collected following 7 days of daily treatment. The tissues were processed and the expression levels on 1310 proteins were assessed (Somascan provided by SomaLogic, Inc., Boulder, Colo.).

Three statistical methods were used to identify protein expression that discriminated between Formula 1, gabapentin and vehicle on day 8, following a single dose, and on study day 14 following multiple dosing.

A comparison between day 8 and day 14 within each group was also performed. All methods were conducted on scaled data. First, a Student's t-test was performed in order to compare proteins between groups. Second, the LASSO (least absolute shrinkage and selection operator) method was applied. This is a regression technique that simultaneously performs variable selection and model coefficient modification. These models used group as the outcome and all 1310 proteins as the starting predictors. LASSO was then tuned to shrink unimportant coefficients to zero, leaving approximately the ten most important predictors of (or discriminators between) the groups.

The final method used was Random Forest. Random Forest is an ensemble method that randomly selects subsets of proteins, creating classification trees based on the subset to discriminate between the two groups. The process was repeated 2000 times. The variable importance of each protein is then ranked based on the proteins' performance in the trees.

The LASSO method automatically gives the top 10 predictors of group discrimination. The T-test and Random Forest results were sorted by p-value and Mean Accuracy Decrease, respectively, and the top 10 from these results were selected. Further barriers were placed on the top 10 predictors selected by the statistical analysis in order to further select meaningful changes: (1) a selected protein should rank between the first 10 important proteins in the plasma and in the skin; (2) the change should be in the same direction in the plasma and in the skin; and (3) the p-value in the Student's t-test should be equal to or smaller than 0.01.

This analysis and selection process revealed a single protein fitting all criteria, 14-3-3σ (STRATIFIN gene). The bio-statistical analysis showed that in the skin, 14-3-3σ ranked second using the LASSO ranking method and 8 using the Random Forest ranking method. Student's t-test vs. vehicle showed a p-value of 0.0110. Exploring the changes in protein obtained in the plasma when comparing day 8 and day 14, 14-3-3σ ranked 7 using the LASSO ranking method, and the Student's t-test p-value was <0.01.

Figure 15:
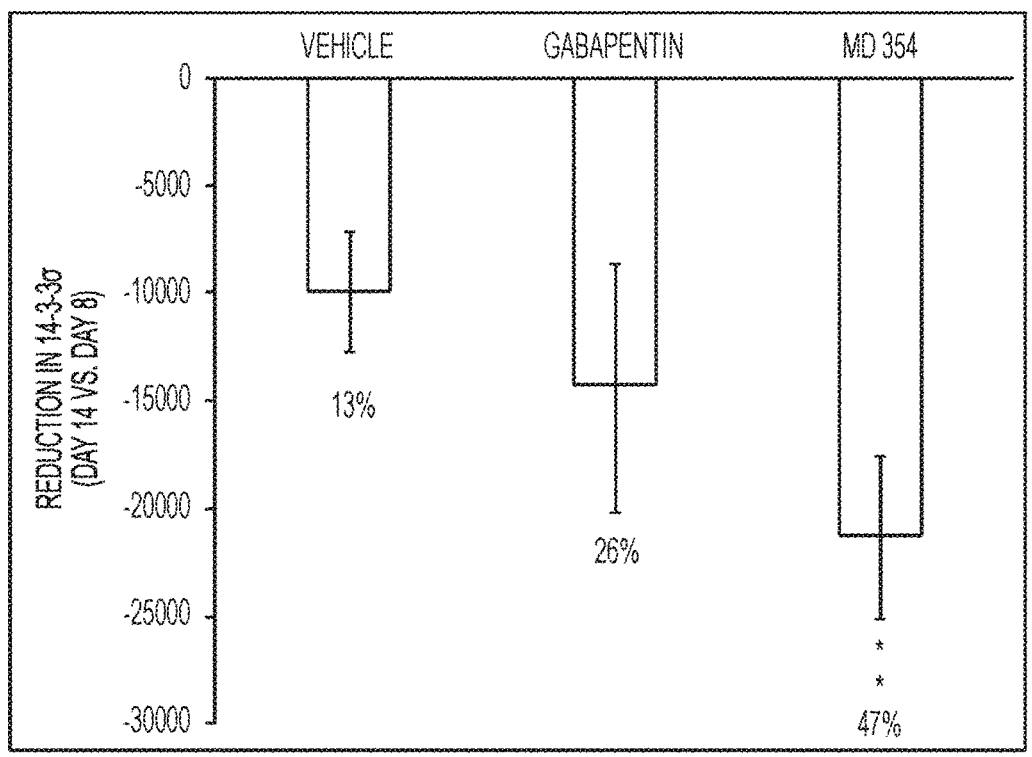
FIG. 15 shows the effect of daily administration of Formula 1 from day 8 to day 14 on the expression of 14-3-3σ in the blood of Taxol dosed mice, according to one embodiment of the invention.
Figure 16:
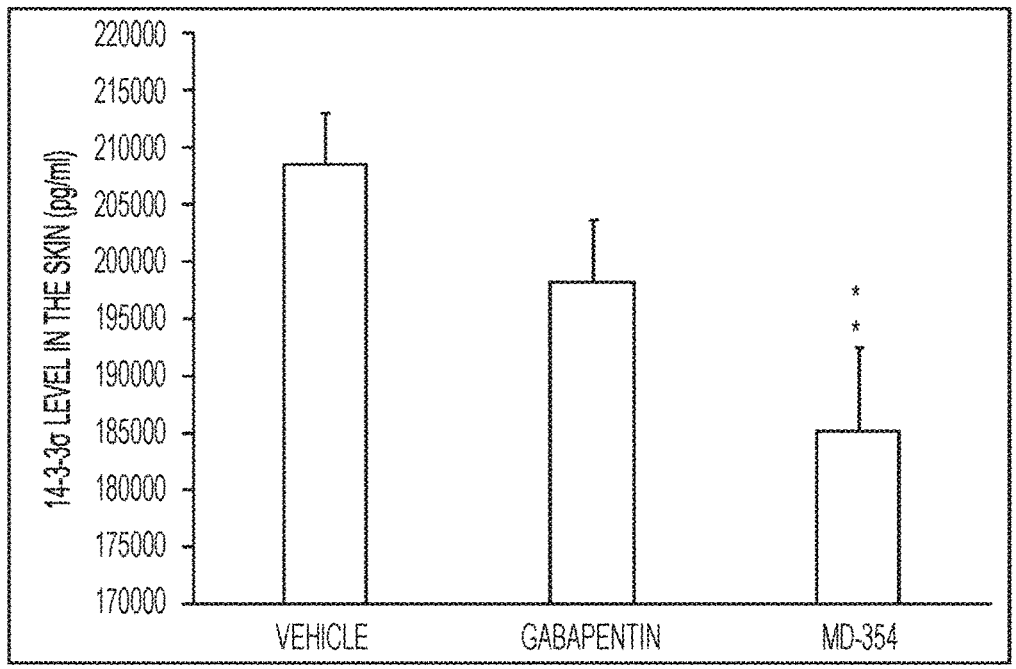
FIG. 16 demonstrates the changes in 14-3-3σ in the hind plantar skin of mice dosed with Taxol and treated with Formula 1. As illustrated, expression of 14-3-3σ was significantly reduced following repeated dosing with Formula 1 vs. vehicle (p<0.01), according to one embodiment of the invention.

FIG. 15 shows the relative decrease in stratifin in percentages from day 8 to day 14 following treatment with vehicle, gabapentin or Formula 1. Treatment with Formula 1 resulted in a decrease of nearly 50% in stratifin vs. naïve animals. These changes were significant vs. the changes observed in the vehicle-treated animals. Treatment with Formula 1 significantly reduced the 14-3-3σ expression in the skin on study day 14 vs. vehicle-treated animals (FIG. 16).

EXAMPLE 3

Putative MoA Through Targeting 14-3-3o: Biological Significance

According to Li et al. discovered that selected 14-3-3 isomers, including the o isomer, interact with the $Ca_v2.2$ ion channel, a subtype of voltage-gated $Ca^{2+}$ channels that is central for neurotransmitter release in the presynaptic nerve terminal. They reported that the 14-3-3 protein (isomers E,t,y,o and ξ) reduced inactivation of $Ca^{2+}$ channels in both the open and the closed state This protein-protein interaction is mediated by the binding of 14-3-3 o the carboxyl tail of the channel pore-forming a1B subunit which contains at least two 14-3-3 potential interaction sites.

Cav2.2 is an N-type calcium channel. This channel mediates the neurotransmission of pain signals in the spinal cord, which makes its suppression a desirable target for the treatment of chronic pain. Prialt® (Jazz Pharmaceuticals, ziconotide), a selective Cav2.2 blocker, has been approved by the FDA for chronic pain treatment. Although proven to be effective in treating some chronic pain patients, the drug has serious limitations including its invasive route of administration (intrathecal) and low therapeutic window.

In contrast to ziconotide Cav2.2 blocker currently available for treatment of pain, Formula 1 may offer some advantages. Formula 1 does not directly target CaV2.2, but modulates indirectly by reducing 14-3-3 leading to a reduction in the 14-3-3/Cav2.2 interaction and ultimately to a reduction in $Ca^{2+}$ influx. In contrast to reported side-effects of ziconotide, no side effects and no tolerance effect were observed following treatment with Formula 1. A cumulative analgesic response was observed in some of the models of neuropathic pain and a longer lasting response was observed in other models. Formula 1 is the only Cav2.2 modulator active via oral administration.

EXAMPLE 4

Senerga® Phenotypic Screen Data

Formula 1 was discovered following a comprehensive Senerga® Phenotypic screening. The compound showed activity in pain-related models, without affecting the withdrawal threshold of naïve animals, suggesting a limited CNS effect. Formula 1 was not effective on swelling, thus excluding NSAID-like mechanism of action.

The compound demonstrated a good pharmacological safety profile, with no immediate alarming phenomena (no effect on blood pressure, no post-mortem finding, no effect on bodyweight or food consumption and no effect on specific CNS-related tests). This initial data suggests that Formula 1 and its chemical analogs may be candidates for the treatment of pain by a potentially novel mechanism of action.

EXAMPLE 5

In Vitro Absorption of Bioavailability

5.1: Permeability Using Caco-2 Cell Monolayers

Formula 1 was evaluated for cellular permeability using Caco-2 cell monolayers. Both the apical-to-basolateral (A-B) and basolateral-to-apical (B-A) bidirectional permeability and efflux ratios were evaluated in the assay. The observed $P_{app}$ A-B was $6.6 \times 10^{-6}$ cm/s, demonstrating moderate passive permeability ($10 \times 10^{-6}$ cm/s ? $P_{app}$ A-B? $1 \times 10^{-6}$ cm/s is considered moderate permeability).

The observed $P_{app}$ B-A was high, at $68.3 \times 10^{-6}$ cm/s, leading to an efflux ratio of 10.4. This high efflux ratio suggested that the compound is a substrate for one or more efflux transporters. When an efflux transporter inhibitor (Pgp inhibitor) was added in the assay, the $P_{app}$ A-B value increased from $6.6 \times 10^{-6}$ cm/s to $45.2 \times 10^{-6}$ cm/s, demonstrating that the compound is a good substrate for this efflux transporter (Pgp).

5.2: Physicochemical Properties

Formula 1 has good physicochemical properties (MW<500 Da, cLogP and cLogD=2.6, and no "Rule of Five" violations). The low polar surface area (PSA<70 Å 2) also suggests that the compound should be a good membrane and brain penetrant (Table 1).

TABLE 1

| Physicochemical properties of Formula 1 | | | | | | | | | | |
|---|---|---|---|---|---|---|---|---|---|---|
| Comp | MW | ALogP | cLogP | cLogD_7_4 | #HD | #HA | #RB | PSA | Frac_SP3C | RoF |
| Formula 1 | 439.5 | 3.2 | 2.6 | 2.6 | 0 | 6 | 7 | 62.74 | 0.68 | 0 |

EXAMPLE 6

Pharmacokinetic Studies

Figure 17:
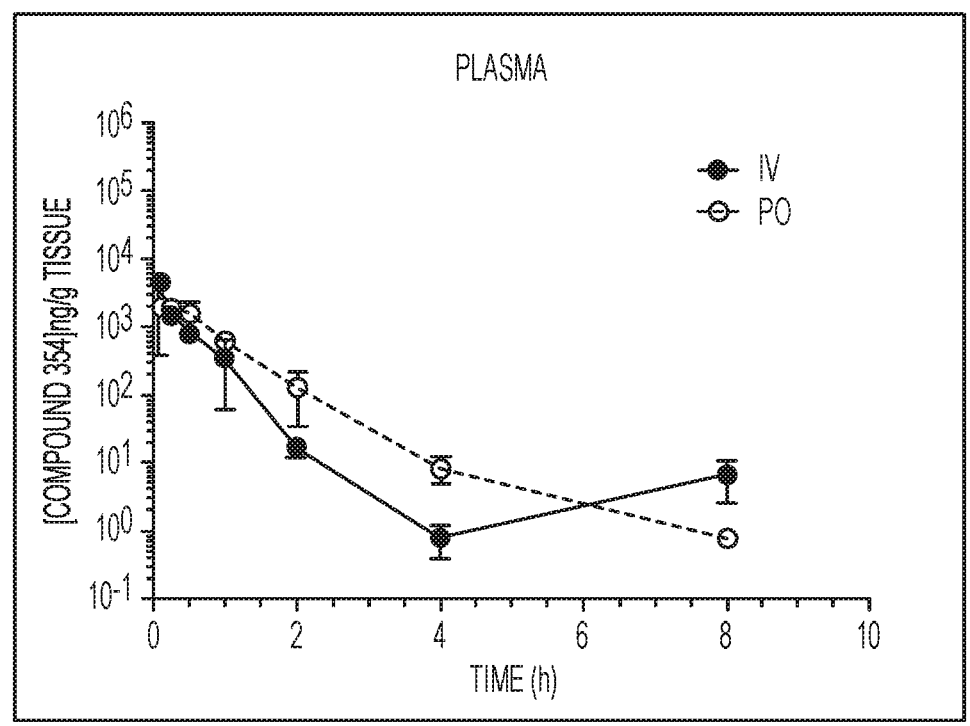
FIG. 17 demonstrates changes in Formula 1 following the IV route of administration at a dose of 5 mg/kg or the PO route of administration at a dose of 50 mg/kg. Plasma collection was carried out over the course of 8 hours, according to one embodiment of the invention.

Pharmacokinetic studies of MD-354 were performed in mice following 50 mg/kg oral and 5 mg/kg intravenous administration (FIG. 17). Following intravenous administration of 5 mg/kg, the initial plasma concentration (C0) reached 7941 ng/mL. The plasma concentration decreased in a multi-phasic manner to 6.74 ng/mL at 8 hours post-dose, with a terminal half-life of 0.35 h (excluding the data at the 8 h time point). The compound demonstrated a moderate systemic plasma clearance (CLp) of 46.1 mL/min/kg (mouse hepatic blood flow rate: 90 mL/min/kg) and a moderate steady-state volume of distribution (Vss) of 1.08 L/kg.

Following oral administration of 50 mg/kg, a high peak plasma concentration (Cmax) was achieved within 5 min, reaching 1933 ng/mL. The plasma concentration decreased in a multi-phasic manner to 0.76 ng/mL at 8 hours post-dose. The terminal half-life was 0.85 h. The absolute oral bioavailability was relatively at 10.5%.

Two additional sets of oral data in mice showed similar pharmacokinetic profiles in all studies. The peak 354 plasma concentrations were high, at 3157 ng/mL and 3001 ng/mL, all reached within 5 min. The plasma concentrations decreased to 8.4 ng/mL and 11.4 ng/mL at 8 hours post-administration, with a terminal half-life of 1.19 h and 1.25 h, respectively. Both sets of data showed oral bioavailability values of 14.1% and 14.7%, respectively.

EXAMPLE 7

Tissue Distribution 7.1 In Vitro Studies: Plasma Protein Binding

The plasma protein binding assay for Formula 1 was conducted in mouse and human plasma at a single concentration of 1 μM using the method of equilibrium dialysis. The compound showed moderate-to-high plasma protein binding with 84% and 92% plasma protein bound in mouse and human plasma, respectively. The plasma protein binding of the compound is acceptable.

7.2 In Vivo Studies 7.2.1 Levels of Formula 1 in Mouse Tissues

Tissue distribution studies were conducted by administration of the compound to mice at a dose of 50 mg/kg orally and intravenously. Plasma and tissue samples were collected at various times from 5 min to 8 h. The tissue-to-plasma concentration ratios measured after oral dosing were: 0.6 (range: 0.3-1.1, brain), 3.2 (range: 1.9-5.0, spinal cord), 6.5 (range: 0.9-10.3, liver), 24.0 (range: 5.1-59.9, lung), 6.6 (range: 1.2-14.9, heart), 16.9 (range: 4.3-26.8, kidney), 77.5 (range: 11.5-341, spleen), 29.2 (range: 6.3-50.2, cecum), 67.4 (range: 11.6-326, colon), 5.2 (range: 2.1-8.0, testes). The concentration-time profiles of the compound in these tissues generally followed those in plasma. The tissue-to-plasma concentration ratios in these selected tissues are generally within the normal ranges of the marketed drugs.

In general, it takes substantial effort to discover brain and spinal cord-penetrating CNS drugs. Brain levels are commonly used as a surrogate for spinal cord levels when the test compound is not mediated by uptake or efflux transporters. Efflux transporter Pgp is highly expressed on the luminal side of the blood-brain barrier and blood-spinal cord barrier. When a drug is a substrate for Pgp, such as Formula 1, the compound should have a higher concentration in the CSF than in the brain, since the compound is pumped out of brain at the BBB but into the CSF at the BCSFB, which makes the compound available for entering the spinal cord tissue.

There are complex equilibria between the compound concentrations in blood, CSF and spinal cord. A high concentration in the CSF would yield a large concentration in the spinal cord. Since Formula 1 is a Pgp substrate and highly tissue-bound, its higher concentrations in the spinal cord tissue compared to the brain tissue are not surprising (Table 2).

EXAMPLE 8

Metabolism Transporter 8.1 In Vitro Metabolism 8.1.1 Blood/Plasma Stability

Formula 1 was stable in both mouse and human plasma, with t90 values greater than 4 h, whereas it was unstable in rat plasma, with a t90 of less than 1 h (t90 should be greater than 4 h in order to be considered stable). Most of the efficacy and safety pharmacology was therefore run in mice.

8.1.2 Metabolic Stability in Liver Microsomes/Hepatocytes Across Species

Metabolic stability studies in mouse, rat and human liver microsomes were performed at a compound concentration of 1 μM. The intrinsic clearance (CLint) values were >346 μL/min/mg in both mouse and rat liver microsomes (t1/2 of <4 min) and 174 μL/min/mg in human liver microsomes (t1/2 of 8 min). This may indicate that the compound undergoes significant pre-systemic metabolism or a first-pass effect in the liver of the tested species, since the compound shows good cellular permeability.

The results from this study showed that N-dealkylation and oxidation appeared to be the major metabolic pathways. A total of five metabolites were detected in all three species. There were no significant differences in metabolic profiles between mouse and rat liver microsomes, suggesting that either mouse or rat can be used as a rodent species for GLP toxicology studies. Due to the similarity in the plasma stability of the compound in the mouse and the human plasma, and toxicology studies would preferably be performed in the mouse. No unique human metabolites were detected in this study.

8.2 Enzyme Inhibition and Induction 8.2.1 Inhibition of CYP450 Enzymes

Preliminary in vitro studies on reversible inhibition of major CYP450 enzymes were conducted in a cocktail format for this compound. The IC50 values were 4 μM for CYP2C9, 5 μM for CYP2C19, and greater than 10 μM for CYP3A4, 2C8, 2D6, and 1A2. If total plasma concentrations in humans are less than 0.4 μM, then in vivo drug interaction studies in clinical trials may not be required for this compound.

EXAMPLE 9

Excretion 9.1 In Vivo Studies

Fecal excretion of the parent compound was evaluated following oral administration of Formula 1 in mice at a dose

Figure 18:
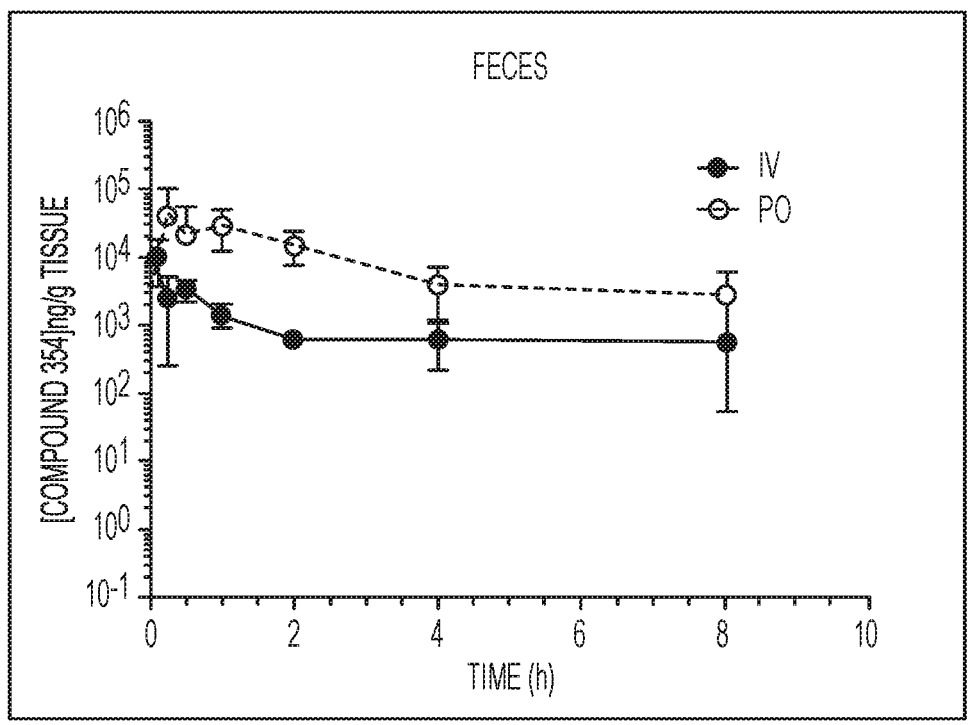
FIG. 18 shows the level of Formula 1 in the feces of the mice following IV (5 mg/kg) and PO (50 mg/kg) dosing, according to one embodiment of the invention.

| Organ | Route | | HL_Lambda_z (h) | Cmax (ng/mL) | Tmax (h) | AUClast (h * ng/mL) | AUCINF_obs (h * ng/mL) | Cl_F_obs (ml/h/kg) | Vz_F_obs (ml/kg) |
|---|---|---|---|---|---|---|---|---|---|
| Plasma | SC | Mean | 0.37 | 1896.50 | 0.25 | 1377.67 | 1390.00 | 7217.50 | 3847.83 |
|  |  | SD | 0.03 | 143.22 | 0.00 | 99.59 | 83.66 | 440.01 | 414.54 |
| Brain |  | Mean | 0.39 | 1375.33 | 0.25 | 789.67 |  |  |  |
|  |  | SD | 0.04 | 363.34 | 0.00 | 118.73 |  |  |  |
| Spinal Cord |  | Mean | 0.53 | 11932.33 | 0.25 | 6214.00 |  |  |  |
|  |  | SD | 0.06 | 2279.38 | 0.00 | 481.07 |  |  |  |
| Plasma |  | Mean | 1.20 | 3079.17 | 0.08 | 2593.50 | 2611.33 | 40333.00 | 72161.50 |
|  |  | SD | 0.20 | 410.73 | 0.00 | 619.75 | 613.48 | 10506.83 | 31248.75 |
| Brain |  | Mean | 0.74 | 6749.00 | 0.08 | 2766.67 |  |  |  |
|  |  | SD | 0.21 | 1682.19 | 0.00 | 347.82 |  |  |  |
| Spinal Cord |  | Mean | 1.56 | 29979.33 | 0.08 | 15450.67 |  |  |  |
|  |  | SD | 0.65 | 5397.53 | 0.00 | 3160.44 |  |  |  | of 50 mg/kg and intravenous administration at a dose of 5 mg/kg. Peak concentrations in feces were 150 µg/g and 33 µg/g from oral and intravenous dosing, respectively. These peak concentrations were generally achieved within 1 h post-oral dosing and within 5 min post-intravenous doing. The concentrations remained high (greater than 1 µg/g) even after 8 h post-dosing by both administration routes (FIG. 18).

EXAMPLE 10

Non-Clinical Safety Pharmacology 10.1 In Vitro Safety Pharmacology Profiling The IC50 for hERG was greater than 10 µM. A generally accepted safety margin against hERG and other important cardiac targets is ≥30 (a safety margin is calculated as: IC50/Cmax, free or EC50/Cmax, free). This suggests that a total plasma concentration of at least 4 µM can be reached in humans with a safety margin of 30.

A Cerep activity screen was conducted and was negative against the selected targets at 10 µM (including some important cardiovascular safety-related targets) for Formula 1.

10.2 In Vivo Safety Pharmacology Profiling 10.2.1. General Safety Observations

The tolerability of Formula 1 was evaluated in mice and rats. The compound was well tolerated in mice after 5 days of intraperitoneal dosing at 30 mg/kg, subcutaneous dosing at 60 mg/kg, and oral dosing at 50 mg/kg orally. The compound was also tolerated following a single dose of 100 mg/kg in the mouse. Rats dosed orally, once daily with Formula 1 at 50 mg/kg for a period of 5 days did not show any adverse effects (Table 3).

TABLE 3

Safety pharmacology data following repeated dosing of Formula 1 using different routes of administration.

| Route | Maximum dosage tested | Duration of dosing (days) | Species | Findings |
|---|---|---|---|---|
| IP | 10 mg/kg | 31 | Mice | NPF |
| IP | 30 mg/kg | 5 | Mice | NPF |
| SC | 60 mg/kg | 5 | Mice | NPF |
| PO | 50 mg/kg | 5 | Mice | NPF |
| PO | 100 mg/kg | 1 | Rat | NPF |
| PO | 50 mg/kg | 5 | Rat | NPF |

NPF—No pathological findings.

10.3. CNS Safety Pharmacology a. Open Field Test

Mice received a 10 mg/kg IP dose of Formula 1. The animals were placed in the open field apparatus after 30 minutes (box of 0.5×0.5×0.5 m length, width and height) for a period of 5 min. The animals' walking distance and speed were evaluated and compared to the vehicle-treated group. No difference was found between the vehicle-treated animals and the Formula 1-treated animals (Table 4).

TABLE 4

| | Distance (m) | Time spent in the center of the field (sec) |
|---|---|---|
| Vehicle | 1.81 ± 0.75 | 22.94 ± 10.65 |
| Formula 1 | 1.94 ± 0.89 | 34.82 ± 23.53 |
| p-value | 0.93 | 0.19 | b. Food Consumption

Animals were tested for food consumption over a period of 3 consecutive days during which they received a daily Formula 1 dose of 10 mg/kg IP. No changes were detected in the food consumption of the animals treated with Formula 1 vs. vehicle treated animals. Vehicle-treated animals consumed an average of 4.39±0.61 g per night compared with 4.00±0.20 g per night for Formula 1 treated animals.

c. Body Weight

Dosing of Formula 1 to naïve mice and naïve rats for a period of 31 days and 7 days, respectively, did not affect body weight gain. At 4 days, vehicle-treated animals gained approximately 1% body weight, going from 25.24±0.74 g to 25.50±0.64 g. Formula 1 treated animals went from 25.28±1.04 g to 25.82±1.25 g.

Animals treated with Formula 1 at a dose of 10 mg/kg IP for a period of 31 days gained 15.64% body weight (changing from 21.44±0.18 g to 25.49±0.46 g). Vehicle treated animals gained 18.9% body weight (changing from 21.45±0.19 g to 23.97±0.62 g; p=0.07), therefore no significant changes were found.

d. Response of Naïve Animals to Heat and Cold Stimuli

Changes in responses of normal withdrawal threshold to heat and cold stimuli in naïve animals following drug treatment may reflect a CNS effect, as in the case of cannabinoids or opioids. Therefore, the response of the naïve mice post-Formula 1 administration at a dose of 10 mg/kg IP was assessed (Table 5). Formula 1 was not effective in altering the basal response of animals stimulated with cold (2±1° C.) or heat (50±1° C.) indicating no CNS effect. This may also suggest that Formula 1 is acting on a target that is elevated or exposed in pain state and is less relevant in naive state.

TABLE 5

Naïve animals' response latency to heat and cold stimuli

| | Response to heat stimuli (50 ± 1° C.) in seconds | Response to cold stimuli (2 ± 1° C.) in seconds |
|---|---|---|
| Vehicle | 15.40 ± 3.10 | 27.60 ± 14.58 |
| Formula 1 | 12.87 ± 2.59 | 20.6 ± 11.39 |
| p-value | 0.13 | 0.37 |

EXAMPLE 11

In Vivo Activity of Formula 1 in Neuropathic Pain Models

IP route of administration was used for initial proof of principle studies with Formula 1. However, the chosen route of administration in most of the studies conducted with Formula 1 was either SC or PO. A brief protocol outline is provided in each section, for the purpose of understanding the results without elaborating on all the detailed procedures.

The data is presented as Mean±SD; the number of animals per group is presented in the study outline box; p<0.05 was considered a significant change. The efficacy summary table also includes the activity of the analogs.

11.1. Activity of Formula 1 Administered SC in Taxol-Induced Neuropathic Pain in Mice Study outline in brief: Animals were dosed daily with Taxol for a period of 8 consecutive days (Day 0 to Day 7). On study day 8, prior to drug dosing, the decrease in withdrawal force (tactile allodynia) was verified by applying the von Frey test. After assigning the animals to their treatment groups, the animals were treated daily for a period of 5 days with either vehicle or Formula 1 at different doses. Gabapentin at a dose of 150 mg/kg was dosed only on days of testing (day 8 and day 14).

Figure 19:
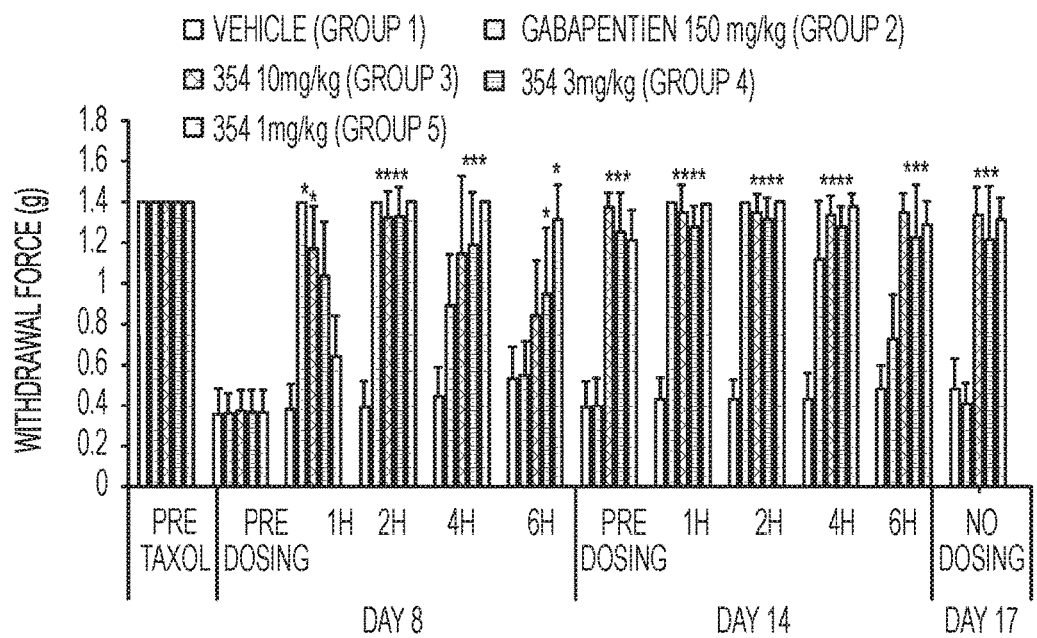
FIG. 19 shows the activity of Formula 1 in Taxol-induced neuropathic pain, according to one embodiment of the invention.

The data presented in FIG. 19 shows that 8 days following Taxol dosing, animals treated with the vehicle experienced a significant low withdrawal force. This low withdrawal force was maintained throughout the entire study period. Treatment with gabapentin resulted in an increase in withdrawal force for a period of 4 hours, indicating analgesia activity. Treatment with Formula 1 at a dose as low as 1 mg/kg resulted in profound analgesic activity for a period of 24 h to 3 days.

Response to heat stimuli was assessed using the hotplate apparatus set at 50YC. Daily Taxol treatment resulted in a decrease in latency response time. At baseline prior to Taxol dosing, the animals' response time to heat was 28.10±1.60 sec (vehicle-treated group). Eight days following Taxol treatment, the response time was reduced significantly (9.90±2.18 sec, $p<0.01$). On study days 13 and 17, the response time was still significantly lower than baseline (11.70±2.11 and 11.10±1.79 sec, respectively). Treatment with Formula 1 at doses of 10 mg/kg, 3 mg/kg and 1 mg/kg were active in increasing the response time. However, it is interesting to note that the beneficial activity of Formula 1 on heat hyperalgesia was more noticeable on study day 14, following repeated daily dosing of the compound, than on study day 8 following a single dose (Table 6). It is suggested that the activity of Formula 1 increases with time, rather than decreasing as would be expected due to tolerance with currently used drugs.

11.2 Activity of Formula 1 in a Chronic Constriction Injury (CCI) Model in Mice Using the SC Route of Administration Study outline in brief: The sciatic nerve of mice was exposed under anesthesia, and 3 loose ligations were placed around the nerve. Animals were allowed to recover for 3 days. Tactile allodynia (von Frey testing) and thermal (hot at 50±1° C. and cold at 2±1° C.) hyperalgesia were then assessed. Animals that experienced tactile allodynia were assigned to their treatment groups (vehicle, gabapentin and Formula 1 at different doses). Animals were subsequently treated daily for a period of 5 days with either vehicle or Formula 1 at different doses. Gabapentin at a dose of 150 mg/kg was dosed only on days of testing (day 3 and day 7).

Figure 20:
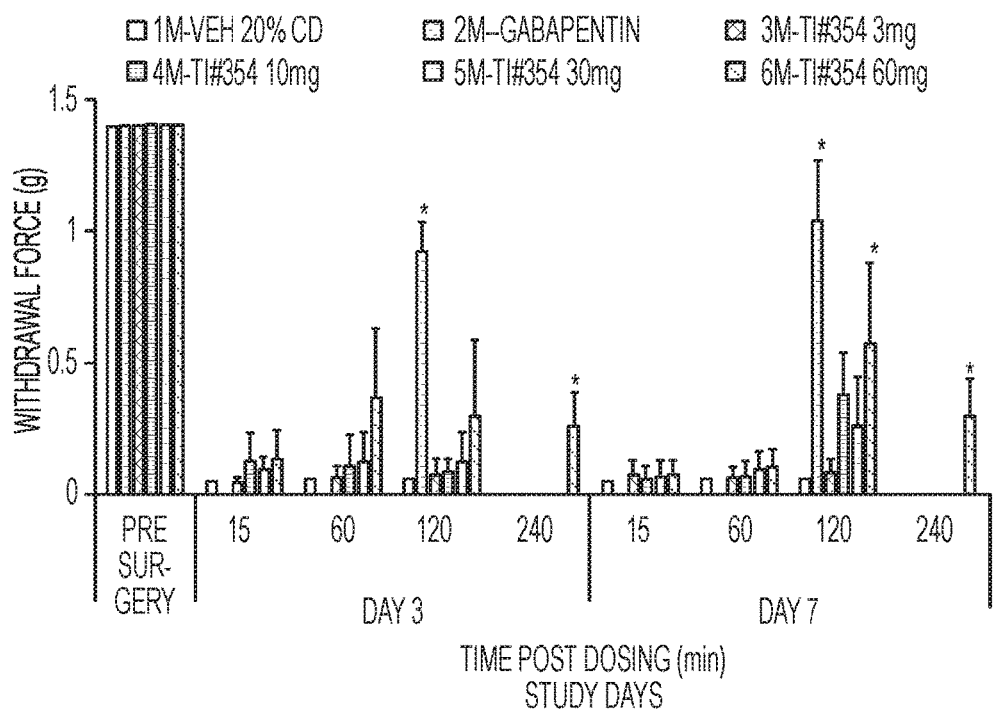
FIG. 20 illustrates the activity of Formula 1 in CCI-induced neuropathic pain, according to one embodiment of the invention.

Three days post CCI, vehicle treated animals experienced reduction in withdrawal force following von Frey testing. The low withdrawal force was also exhibited on study day 7 (FIG. 20). Treatment with gabapentin at a dose of 150 mg/kg resulted in a significant, but not complete, reversal in the withdrawal force. Treatment with Formula 1 at a dose of 60 mg/kg resulted in a significant increase in the withdrawal force following daily repeated treatment.

Figure 21:
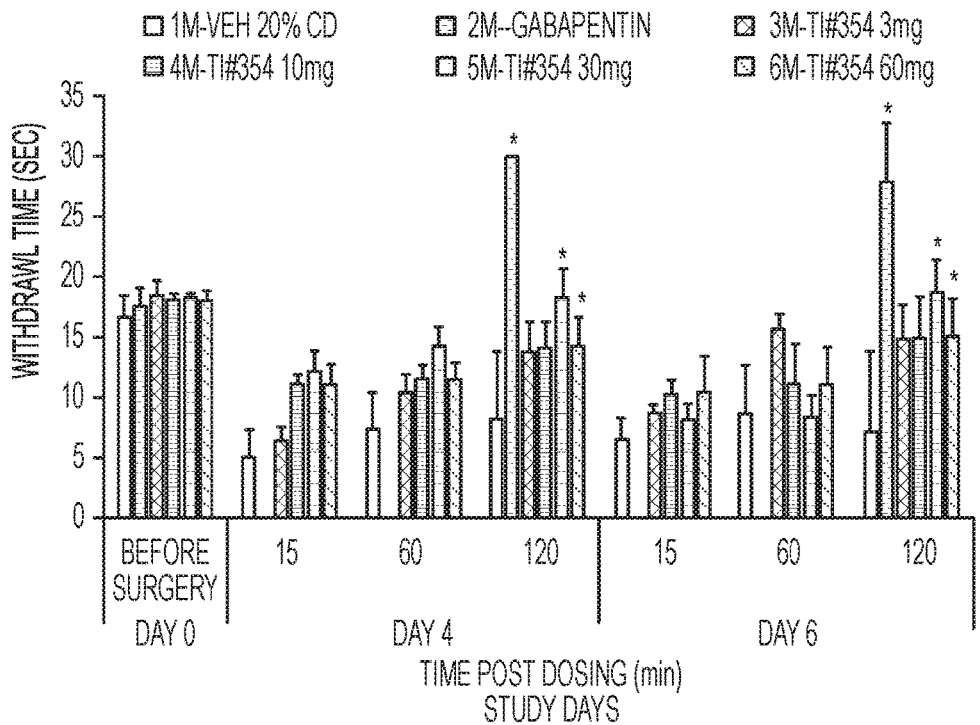
FIG. 21 illustrates the activity of Formula 1 on cold allodynia following CCI-induced neuropathic pain, according to one embodiment of the invention.

In addition to the decrease in the withdrawal force, the vehicle-treated animals exhibited increased sensitivity to cold, as was noticed from the reduction in the animals' response time to a cold plate (2YC) (FIG. 21). Treatment with gabapentin at a dose of 150 mg/kg increased the response time of the animals to values that were higher than the baseline value before the operation, suggesting an adverse CNS effect. Treatment with Formula 1 at 30 mg/kg and 60 mg/kg resulted in increased response time to cold stimuli. The activity peaked at 2 h following a single dose (study day 4) and at 2 h post-dosing on study day 7 following repeated daily dosing (study day 6; FIG. 21).

No tolerance effect was observed for Formula 1 following repeated dosing; on the contrary, repeated dosing led to an increase in the compound's activity. The effect of Formula 1 on the response time in the hotplate test was not significant.

TABLE 6

The effect of Formula 1 on thermal (heat, 50° C.) hyperalgesia

| | Day 0 | Day 8 | | | | | Day 14 | | | | | Day 17 |
|---|---|---|---|---|---|---|---|---|---|---|---|---|
| | | Time (h) vs. treatment dosing | | | | | | | | | | |
| Treatment | Pre-Taxol | Pre-dosing | 1 | 2 | 4 | 6 | Pre-dosing | 1 | 2 | 4 | 6 | No |
| | Mean | | | | | | | | | | | |
| Vehicle | 28.1 | 9.9 | 11.9 | 13.1 | 12.8 | 12.3 | 11.7 | 10.7 | 12.8 | 12.4 | 12.7 | 11.1 |
| Gabapentin 150 mg/kg | 28.5 | 11.1 | 18.9* | 22.5* | 16.7 | 13.8 | 11.2 | 25.1* | 25.0 | 25.1* | 18.7* | 11.5 |
| Formula 1 10 mg/kg | 28.5 | 11.2 | 15.7 | 17.8* | 15.8 | 14.3 | 14.5 | 18.5* | 18.7* | 19.3* | 15.5* | 10.4 |
| Formula 1 3 mg/kg | 28.6 | 12.2 | 15.7 | 19.4 | 14.8 | 14.1 | 19.7 | 18.4* | 24.8* | 23.6* | 20.6* | 12.2 |
| Formula 1 1 mg/kg | 28.8 | 11.4 | 11.9 | 22.8* | 18.9* | 18.5* | 15.8* | 14.9* | 24.6* | 24.2* | 22.0* | 12.4 |
| | SEM | | | | | | | | | | | |
| Vehicle | 1.6 | 2.2 | 2.9 | 3.6 | 3.8 | 2.7 | 2.1 | 1.8 | 1.5 | 1.9 | 3.1 | 1.8 |
| Gabapentin | 1.7 | 2.4 | 3.5 | 5.0 | 4.8 | 4.2 | 1.9 | 5.9 | 5.1 | 5.0 | 4.1 | 2.5 |
| Formula 1 10 mg/kg | 1.5 | 2.6 | 6.6 | 6.5 | 4.6 | 4.0 | 5.1 | 5.7 | 5.1 | 5.9 | 4.6 | 1.6 |
| Formula 1 3 mg/kg | 1.7 | 2.3 | 4.8 | 4.9 | 3.0 | 2.8 | 4.5 | 3.3 | 4.7 | 6.5 | 5.8 | 2.6 |
| Formula 1 1 mg/kg | 1.5 | 2.6 | 2.2 | 3.3 | 3.6 | 3.4 | 3.7 | 3.7 | 4.4 | 4.6 | 5.8 | 2.1 |

11.3 Formula 1 is Active Using the Oral Route of Administration

Figure 22:
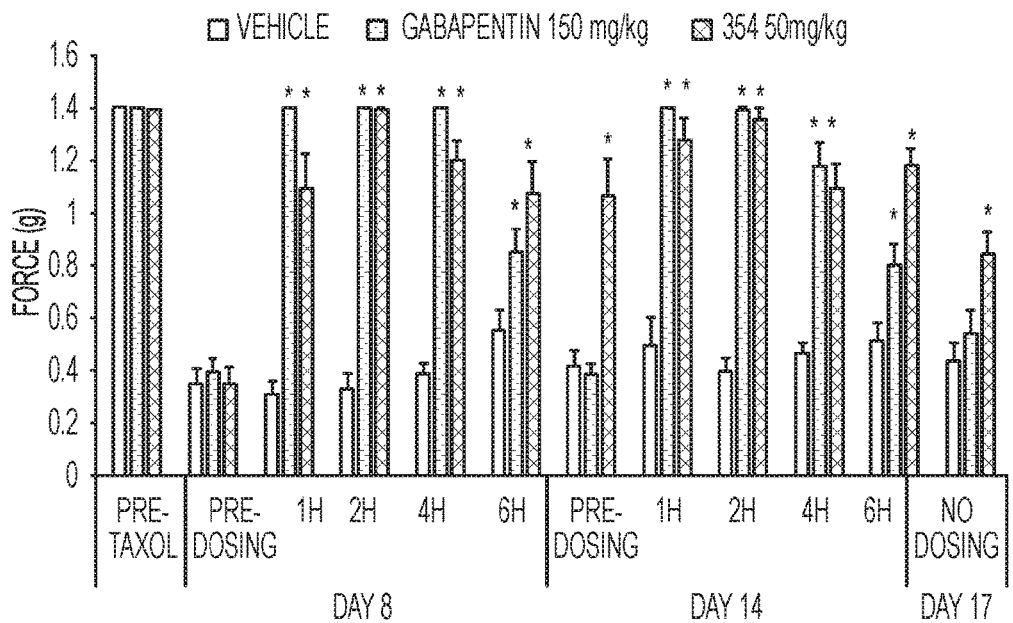
FIG. 22 illustrates the activity of Formula 1, dosed orally, in Taxol-induced neuropathic pain in mice, according to one embodiment of the invention.

The activity of Formula 1 following oral administration was assessed using the Taxol model (see Study Outline in section 7.1). Formula 1 at a dose of 50 mg/kg was active in fully reversing the withdrawal force at 2 h post-single administration on study day 8. This activity was maintained on study day 14 following repeated daily dosing from day 8 to day 14. Interestingly, Formula 1 was significantly active at 24 h post-dosing with increasing withdrawal force (study day 14 pre-dosing, FIG. 22). No tolerance effect was noted. Gabapentin dosed at 150 mg/kg was active for a period of 4 h post-dosing. No activity was found when animals were introduced to the hotplate test.

In this study, the effect of Formula 1 on heat hyperalgesia was not statistically different from the vehicle-treated group.

11.4 Summary of Activity in Mice

Table 7 summarizes the activity of Formula 1 in mice models of neuropathic pain following repeated daily administration using different routes of administration. The following is observed: (1) Treatment with Formula 1 at relatively low doses was as good as gabapentin at 150 mg/kg, and in some cases even better than gabapentin; (2) The duration of activity of Formula 1 is ty is longer than gabapentin; (3) Gabapentin treatment at a dose of 150 mg/kg resulted in an increase in response time to cold beyond the baseline response time, suggesting a clear CNS effect. Treatment with Formula 1 show activity without CNS effect.

Figure 25:
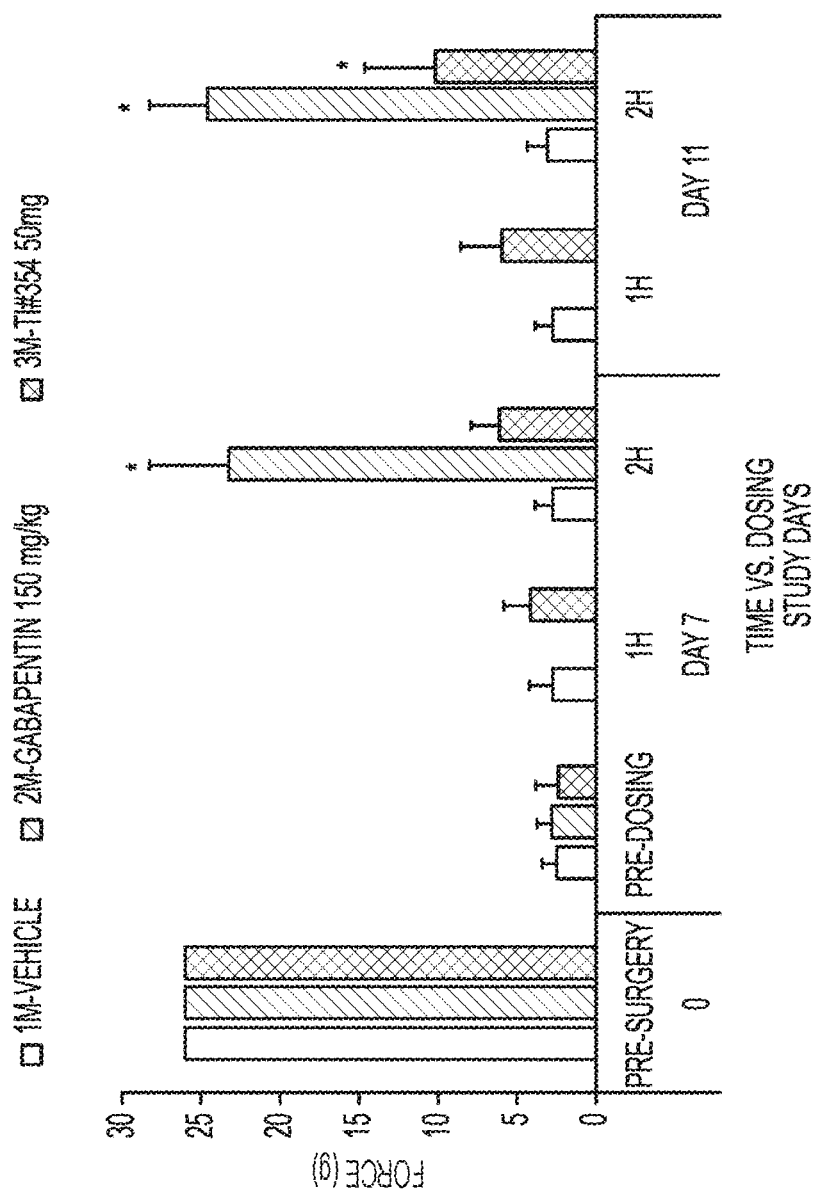
FIG. 25 illustrates the effect of Formula 1 in a CCI model in rats, according to one embodiment of the invention. Continuous dosing of formula 1 resulted in an increase in compound activity.

11.6. Orally Administered Formula 1 is Active in CCI-Induced Neuropathic Pain in the Rat Study plan in brief: SD male rats were operated as described by Bennet and Xie7. On study day 7, the sensitivity of the animals to von Frey was assessed. Only animals that showed significant reduction in withdrawal force were assigned to the treatment groups. The animals were then dosed with either vehicle, gabapentin or Formula 1. Treatment with Formula 1 was not effective 2 h post-single dose. However, following daily treatment with Formula 1 at a dose of 50 mg/kg, the activity of the compound increased and on study day 11 there was a significant increase in the withdrawal threshold at 2 h post-treatment, suggesting pain relief (FIG. 25).

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

It should be understood that although the compounds of Formulas 1-18 may be drawn with specific chirality for the

TABLE 7

Summary of the activity of 354 in animal models for neuropathic pain in mice.

| TI | Model | Route | Doses Tested (mg/kg) | Level of activity (% of maximum effect-baseline) | Duration of activity at maximum effect | Peak of activity (T) | Dose of maximum activity (mg/kg) |
|---|---|---|---|---|---|---|---|
| Gabapentin | CCl | IP | 150 | 66% | 4-6 H | 2-3 H | 150 |
|  |  | SC | 150 | 64% | 4-6 H | 2-3 H | 150 |
|  |  | SC | 150 | >100% | 4-6 H | 2-3 H | 150 |
| 354 | CCl | IP | 3, 10, 30 | 33% | >4 H | 2 H | 30 |
|  |  | SC | 3, 10, 30, 60 | 43% | >4 H | 2 H | 60 |
|  |  | SC | 3, 10, 30, 60 | 100% | >4 H | 2 H | 30 |
| Gabapentin | Taxol | SC | 150 | 100% | 4 H | 2-4 H | 150 |
| 354 | Taxol | SC | 1, 3, 10 | 100% | 3 day | 1 H-3 days | 1 |
| Gabapentin | Taxol | PO | 150 | 100% | 4 H | 2-4 H | 150 |
| 354 | Taxol | PO | 50 | 100% | 24 H | 2-6 H | <50 |

11.5. Formula 1 is Active Per Oral in Taxol-Induced Neuropathic Pain in the Rat

Figure 23:
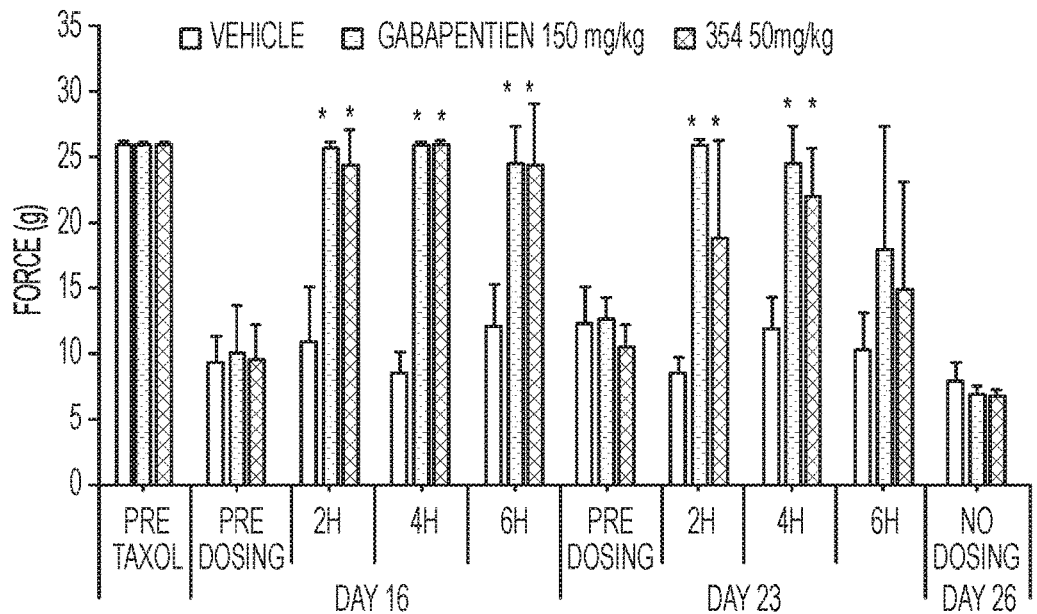
FIG. 23 illustrates the activity of Formula 1, using the oral route of administration in Taxol-induced neuropathic pain in rats, according to one embodiment of the invention.

Study outline in brief: Taxol was administered daily for a period of 17 days (day 0 to day 16). On day 16, the withdrawal force was evaluated using the von Fey test. The animals experienced a reduction of more than 60% in the withdrawal force following repeated Taxol dosing. After a single treatment with Formula 1 at a dose of 50 mg/kg, a full reversal was recorded, i.e. the withdrawal force was similar to the values recorded prior to Taxol dosing commencement. The duration of the analgesic activity was at least 6 h. There was no significant difference between the vehicle and the Formula 1-treated groups 24 h post-dosing (day 23 pre-dosing). The activity of Formula 1 was similar to the activity observed following treatment with gabapentin at a dose of 150 mg/kg (FIG. 23).

Figure 24:
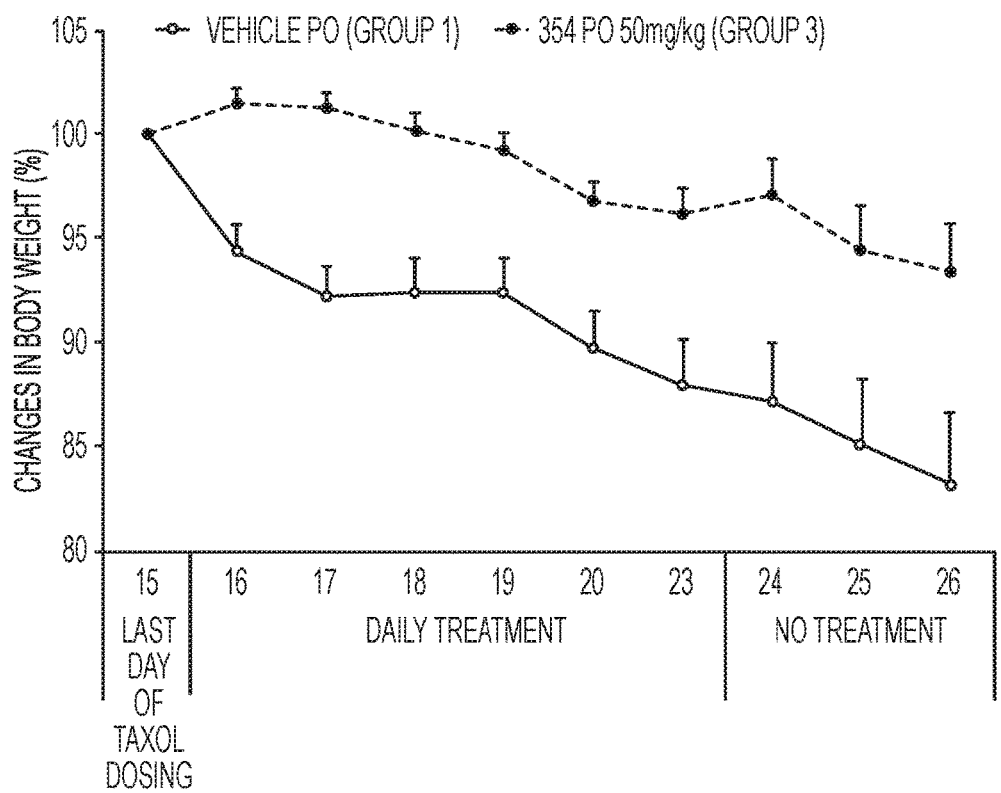
FIG. 24 illustrates the effect of treatment with Formula 1 on body weight loss following Taxol dosing.

Multiple Taxol doses resulted in body weight reduction that continued throughout the entire study period and did not cease even after Taxol dosing was stopped on day 15. In treatment with Formula 1, the rate of weight loss was reduced (FIG. 24), suggesting that Formula 1 improved the general well-being of the animals.

sake of simplicity, one skilled in the art would recognize how to create and separate these various isomers. Accordingly, all isomers of the compounds of Formulas 1-18 may be understood to be within the scope of the present application.

What is claimed is:

1. A method of making a compound of Formula 1,

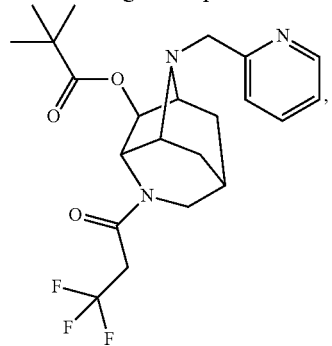

or stereoisomers thereof, wherein the method comprises reacting scopolamine with a reducing agent.

2. The method of claim 1, wherein the method further comprises reacting a compound of Formula 2,

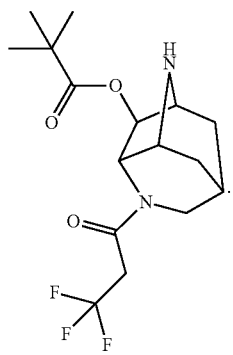 [SMILES: CC(C)(C)C(=O)OC1C2CC3CC(N2)C1N(C(=O)CC(F)(F)F)C3]

3. The method of claim 1, wherein the method further comprises reacting a compound of Formula 3,

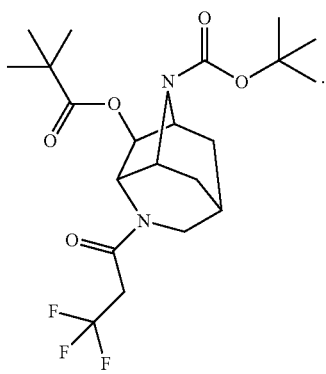 [SMILES: CC(C)(C)OC(=O)N1C2CC3CC1C(C2OC(=O)C(C)(C)C)N(C(=O)CC(F)(F)F)C3]

4. The method of claim 1, wherein the method further comprises reacting a compound of Formula 4,

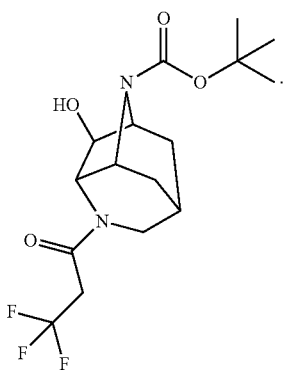 [SMILES: CC(C)(C)OC(=O)N1C2CC3CC1C(C2O)N(C(=O)CC(F)(F)F)C3]

5. The method of claim 1, wherein the method further comprises reacting a compound of Formula 5,

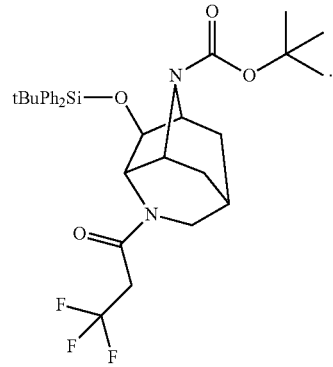

6. The method of claim 1, wherein the method further comprises reacting a compound of Formula 6.b,

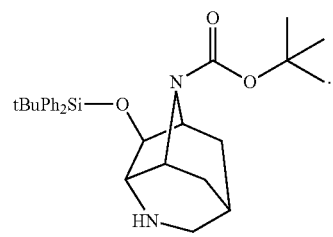

7. The method of claim 1, wherein the method further comprises reacting a compound of Formula 7,

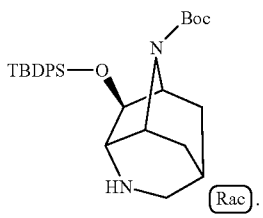

8. The method of claim 1, wherein the method further comprises reacting a compound of Formula 8,

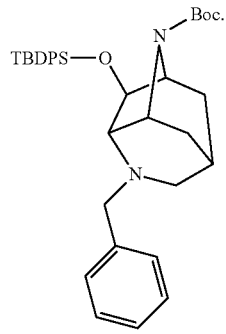

9. The method of claim 1, wherein the method further comprises reacting a compound of Formula 9,

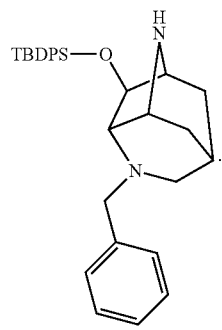

10. The method of claim 1, wherein the method further comprises reacting a compound of Formula 10,

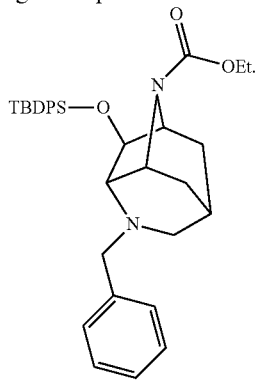

11. The method of claim 1, wherein the method further comprises reacting a compound of Formula 11,

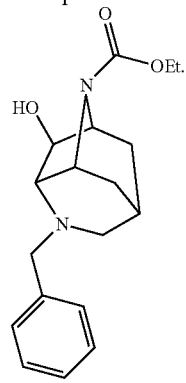

12. The method of claim 1, wherein the method further comprises reacting a compound of Formula 12,

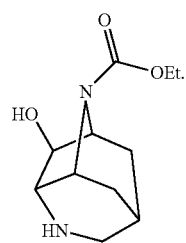

13. The method of claim 1, wherein the method further comprises reacting a compound of Formula 12.a,

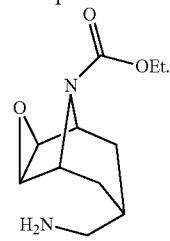

14. The method of claim 1, wherein the method further comprises reacting a compound of Formula 13,

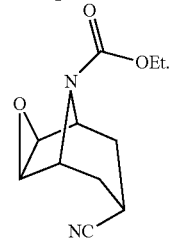

15. The method of claim 1, wherein the method further comprises reacting a compound of Formula 14,

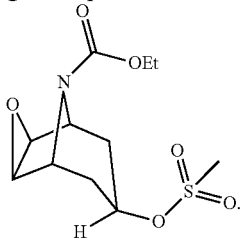

16. The method of claim 1, wherein the method further comprises reacting a compound of Formula 15,

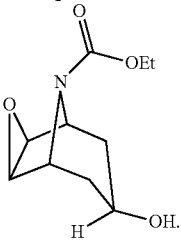

17. The method of claim 1, wherein the method further comprises reacting a compound of Formula 16,

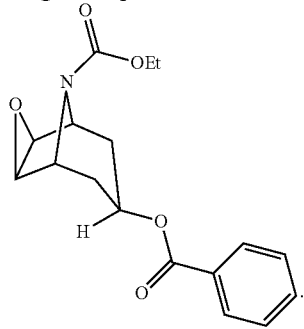 [SMILES: CCOC(=O)N1C2CC(OC(=O)c3ccccc3)CC1C1OC12]

18. The method of claim 1, wherein the method further comprises reacting a compound of Formula 17,

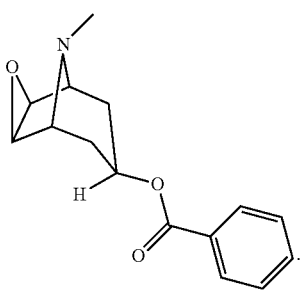 [SMILES: CN1C2CC(OC(=O)c3ccccc3)CC1C1OC12]

19. The method of claim 1, wherein the method further comprises reacting a compound of Formula 18,

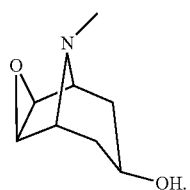

20. A method of making a compound of Formula 1,

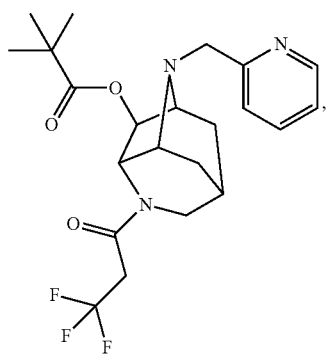 [SMILES: CC(C)(C)C(=O)OC1C2C3CC(CC1N3Cc1ccccn1)CN2C(=O)CC(F)(F)F]

or stereoisomers thereof, comprising reacting scopolamine with sodium borohydrate to form the compound of Formula 1.

21. The method of claim 1, wherein the method comprises reacting scopolamine with a reducing agent and HCL in isopropyl alcohol.

22. The method of claim 20, wherein the method comprises reacting scopolamine with sodium borohydrate and HCL in isopropyl alcohol.

* * * * *